United States Patent [19]
Cowan et al.

[11] 3,978,712
[45] Sept. 7, 1976

[54] METHOD AND APPARATUS FOR TESTING WEAR, SIZE AND RESIDUAL STRESS CONDITIONS

[75] Inventors: John Vincent Cowan, Danbury; Gerald De G. Cowan, New Preston; John Gerald Cowan, Southbury, all of Conn.

[73] Assignee: Scanning Systems, Inc., Brookfield, Conn.

[22] Filed: May 24, 1974

[21] Appl. No.: 473,308

Related U.S. Application Data
[63] Continuation-in-part of Ser. No. 199,487, Nov. 17, 1971, Pat. No. 3,812,708.

[52] U.S. Cl............................. 73/67.5 R; 73/67.8 R; 73/67.8 S; 73/67.9; 73/71.5 US
[51] Int. Cl.².......................................... G01N 29/04
[58] Field of Search...................... 73/67.5 R, 67.6

[56] References Cited
UNITED STATES PATENTS

| | | | |
|---|---|---|---|
| 2,612,772 | 10/1952 | McConnell...................... | 73/67.5 R |
| 3,229,508 | 1/1966 | Sharpe et al..................... | 73/67.5 R |
| 3,780,570 | 12/1973 | Collins............................. | 73/67.5 R |

FOREIGN PATENTS OR APPLICATIONS

| | | | |
|---|---|---|---|
| 468,009 | 3/1969 | Switzerland...................... | 73/67.5 R |
| 1,181,608 | 2/1970 | United Kingdom.............. | 73/67.8 R |
| 155,317 | 10/1963 | U.S.S.R............................ | 73/67.5 R |
| 290,216 | 10/1971 | U.S.S.R............................ | 73/67.6 |

*Primary Examiner*—Richard C. Queisser
*Assistant Examiner*—John P. Beauchamp
*Attorney, Agent, or Firm*—Mattern, Ware, Davis & Stoltz

[57] ABSTRACT

Wheel testing apparatus according to the invention comprises at least one search unit positioned "in-track" replacing a portion of a rail so that the gauged wheels of a passing railroad train roll thereover. Each search unit has a thin vertical rail aligned with the gauge edge of the track for supporting each passing wheel adjacent to its flange, and thereby exposing the running surface of the wheel for testing in a zone which does not interfere with the wheel's path.

Each search unit has two ultrasonic transducers enclosed in a flexible fluid-filled boot and are positioned adjacent to the thin vertical rail in the test zone under the running surfaces of passing wheels, the fluid-filled boot providing good ultrasonic coupling therewith.

The transducers are angled and opposed to send ultrasonic pulses around the wheel in opposite directions. Echoes indicate defects and through transmission times indicate wheel size and wear. Failure of the wheel to accept any significant amount of energy indicates high residual stress.

21 Claims, 43 Drawing Figures

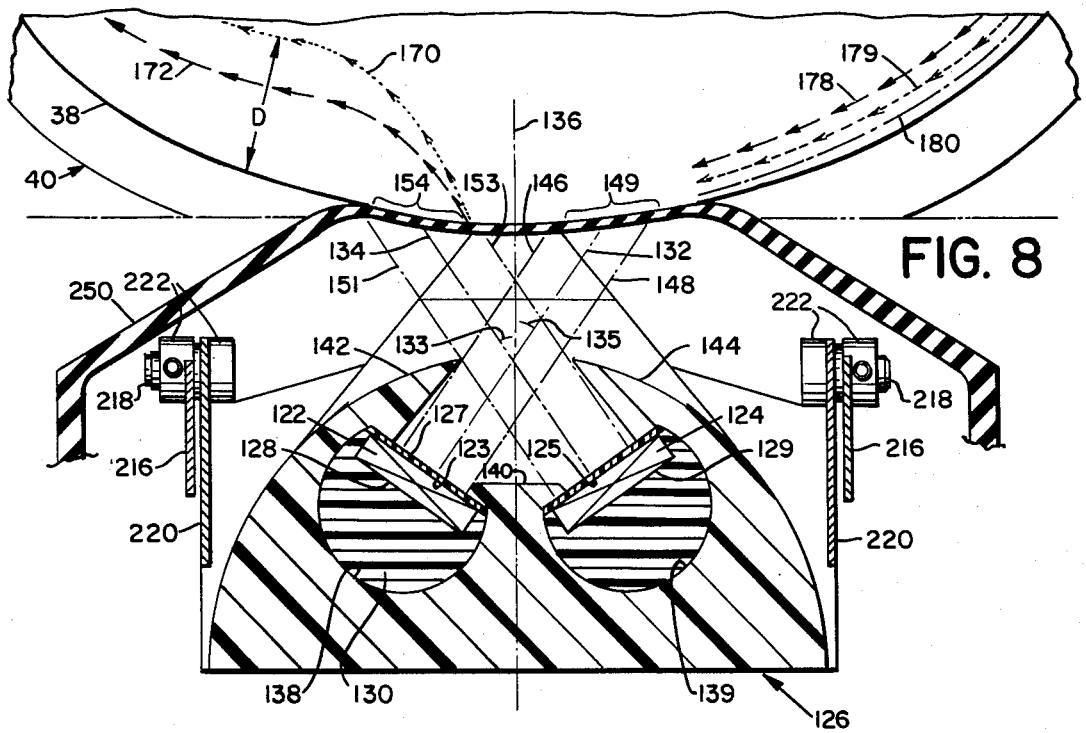
FIG. 8
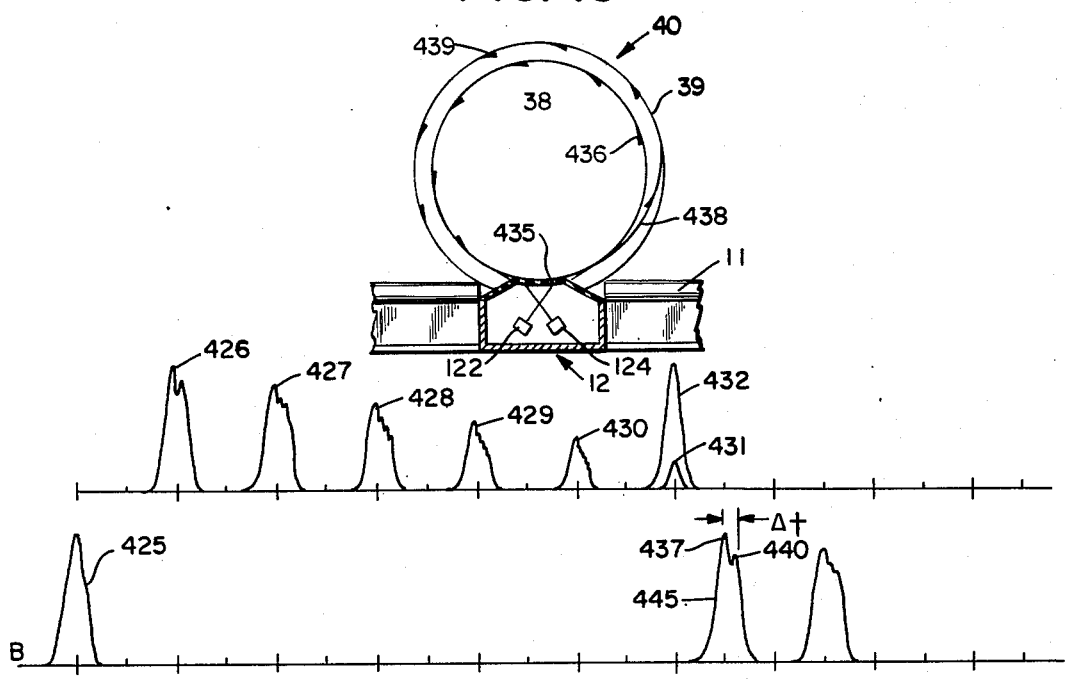
FIG. 15
FIG. 16

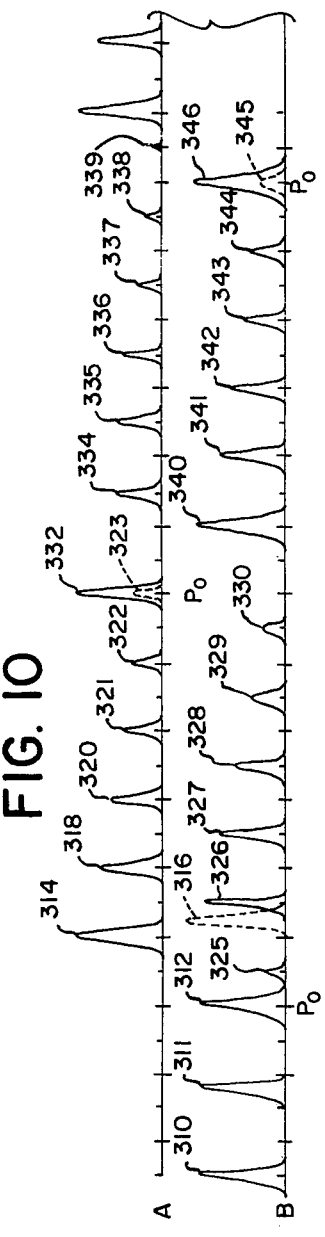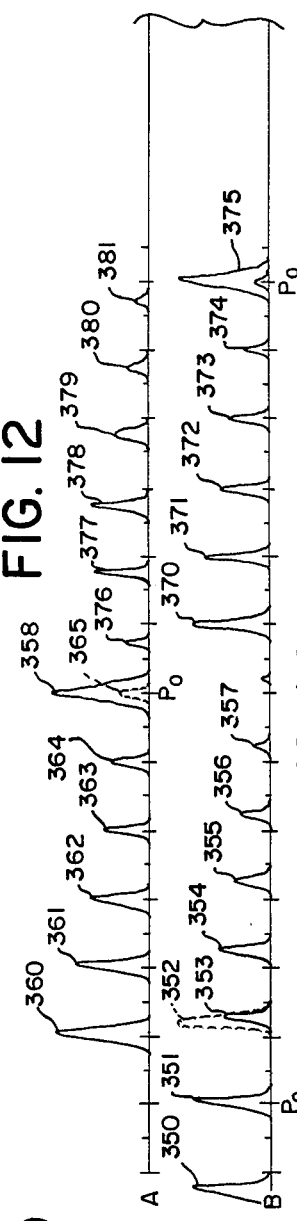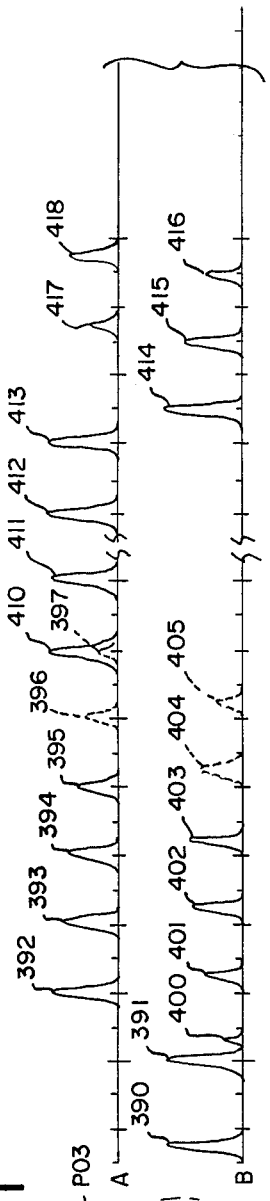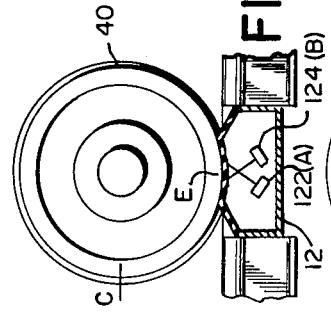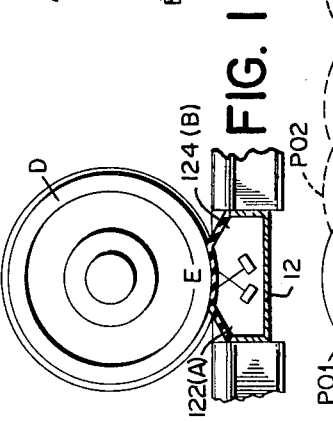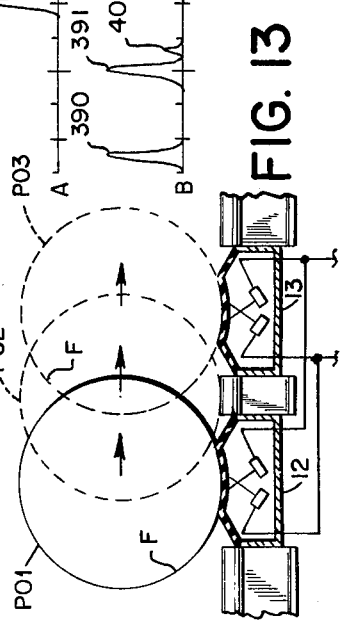

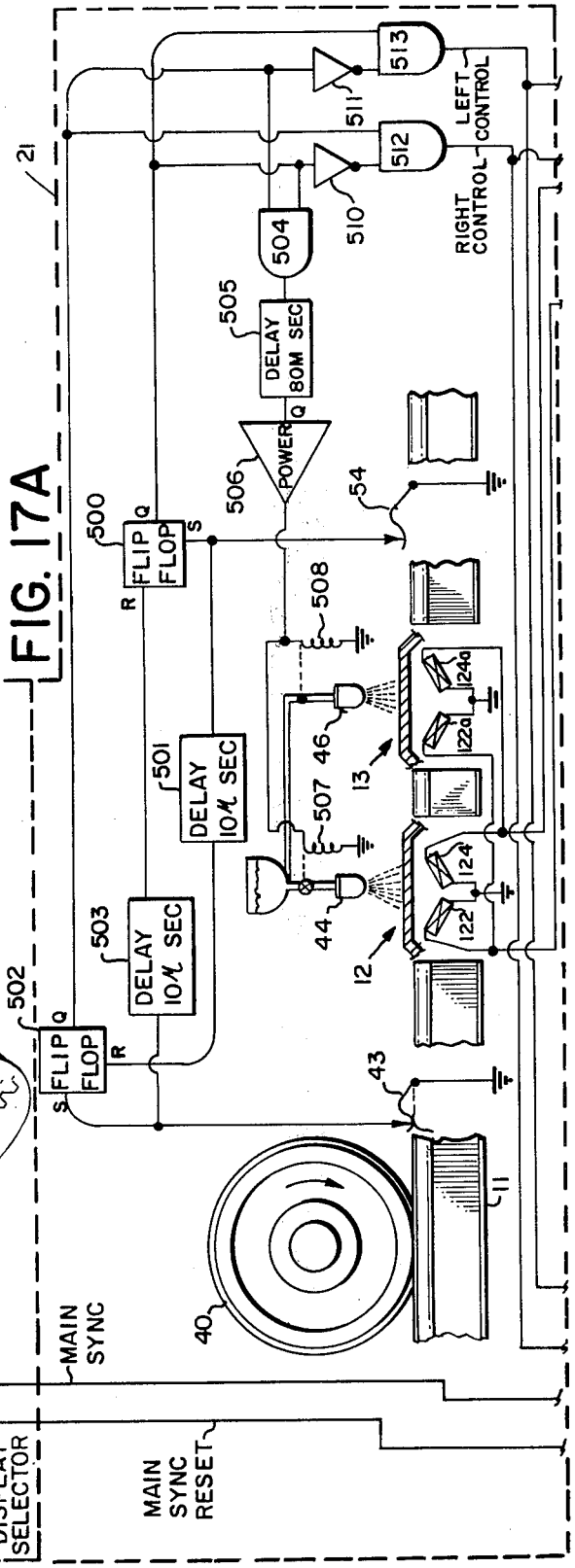
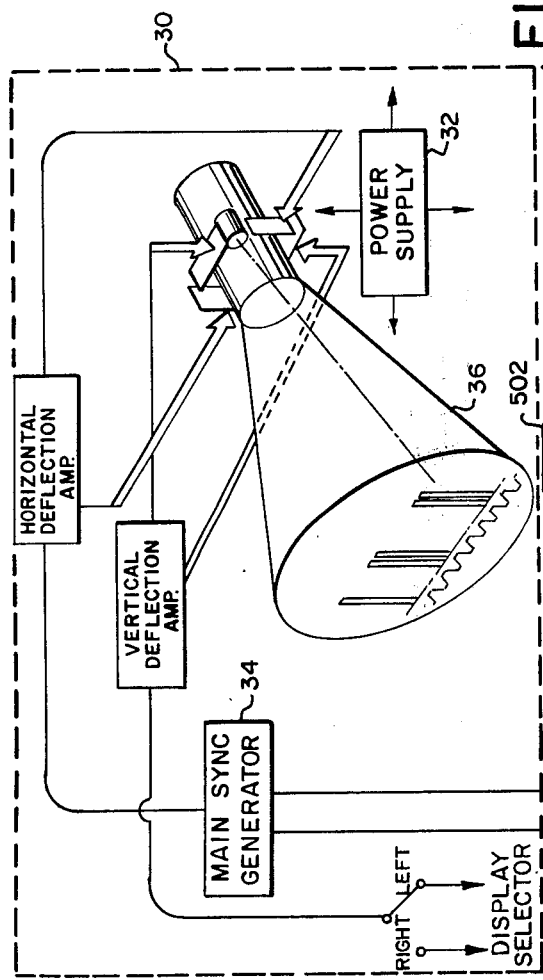
FIG. 17A
| FIG. 17A | FIG. 17C | FIG. 17E |
|----------|----------|----------|
| FIG. 17B | FIG. 17D |          |
FIG. 17

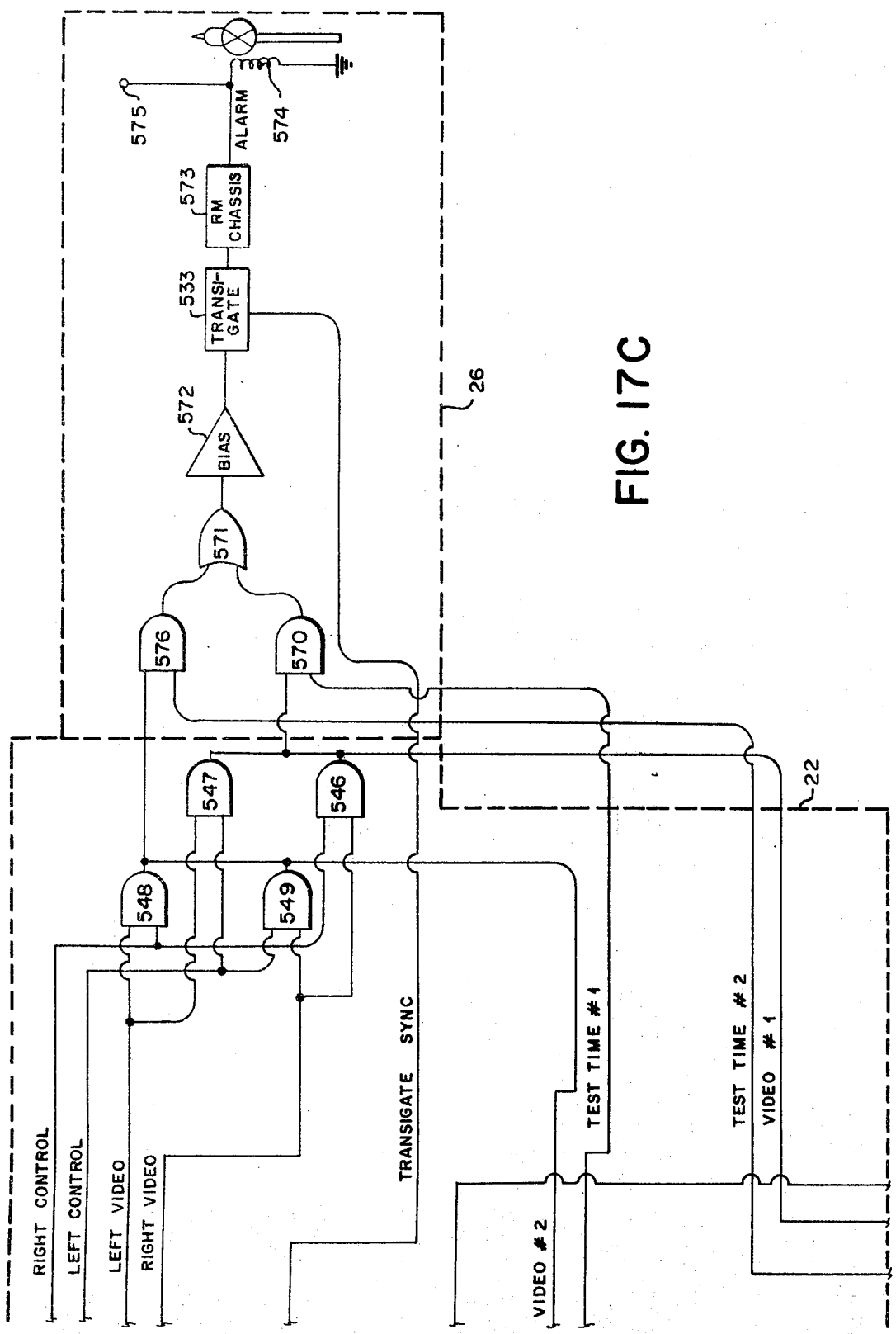

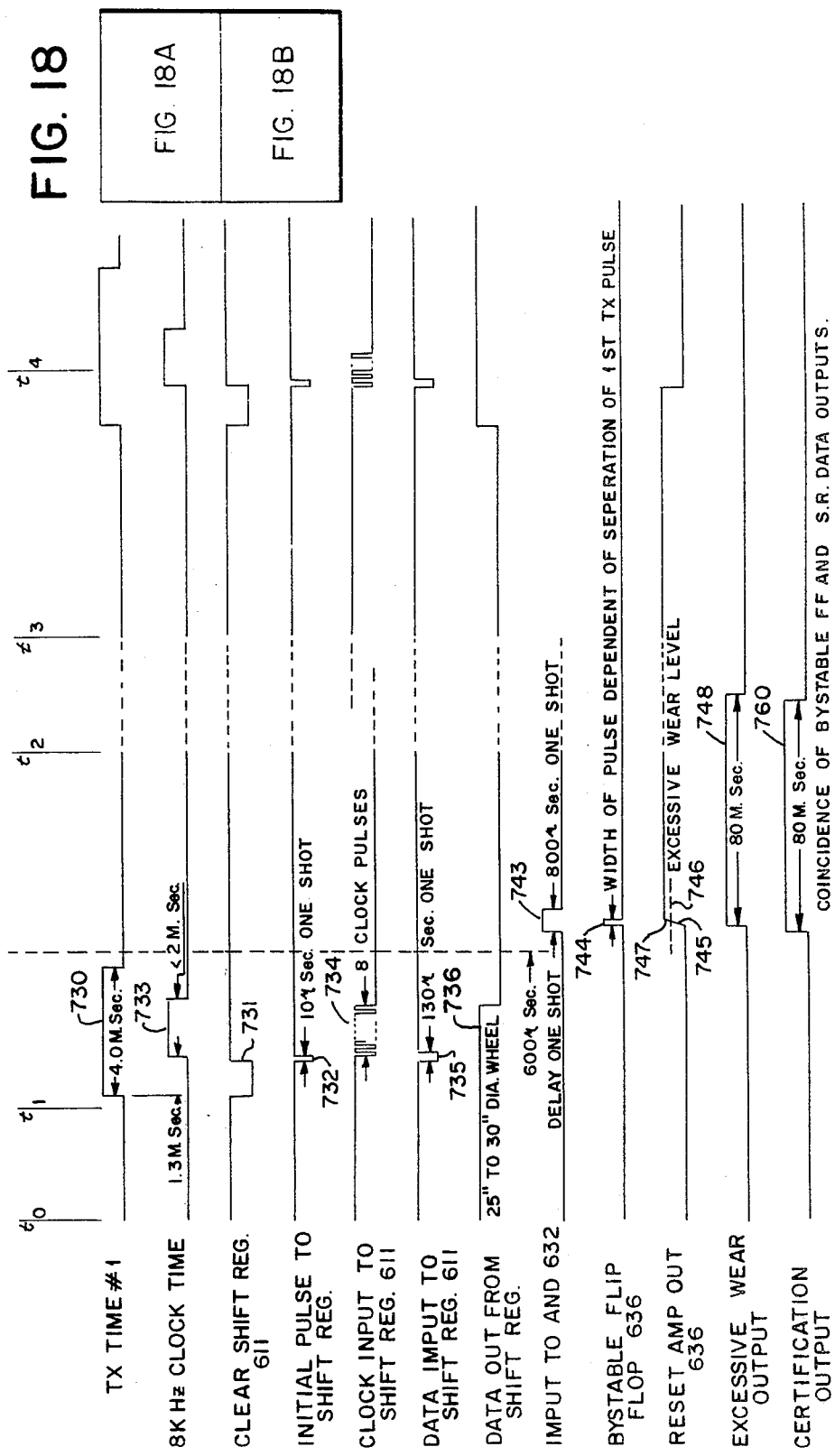

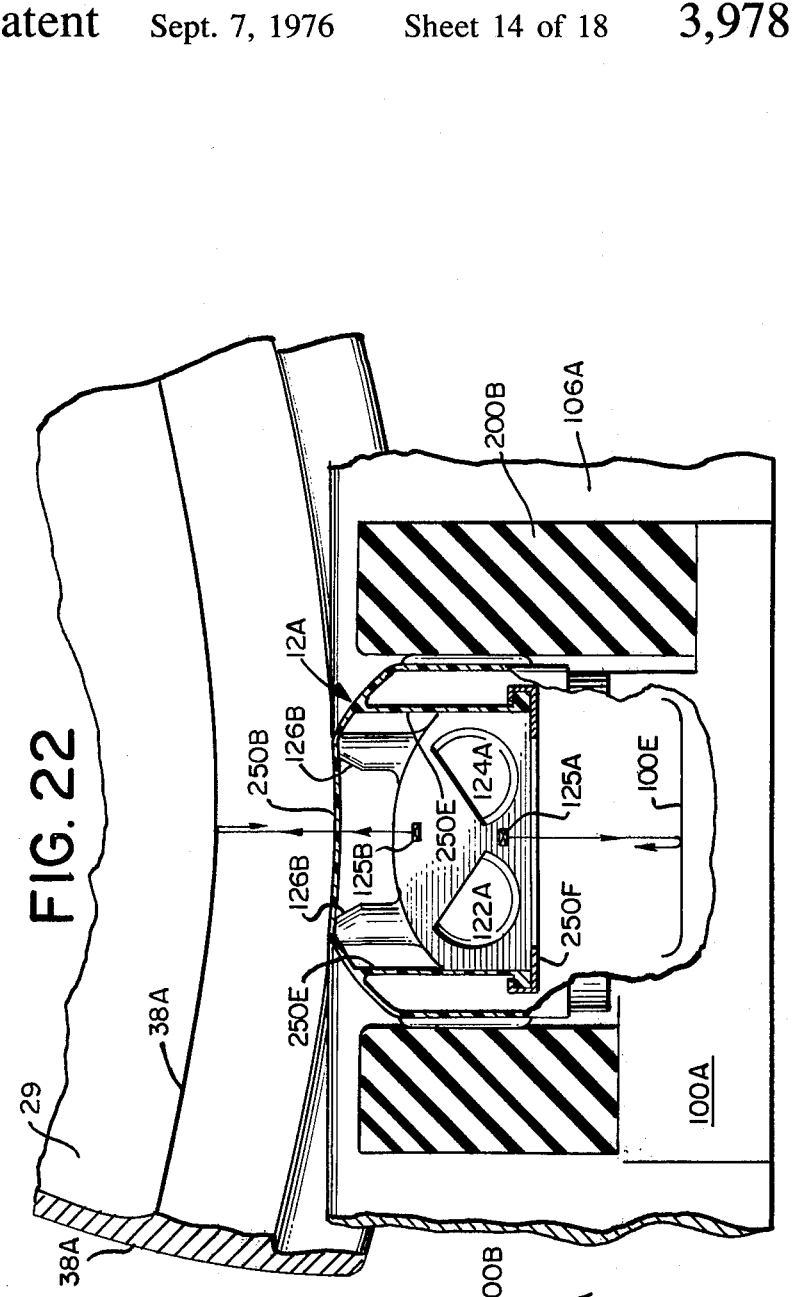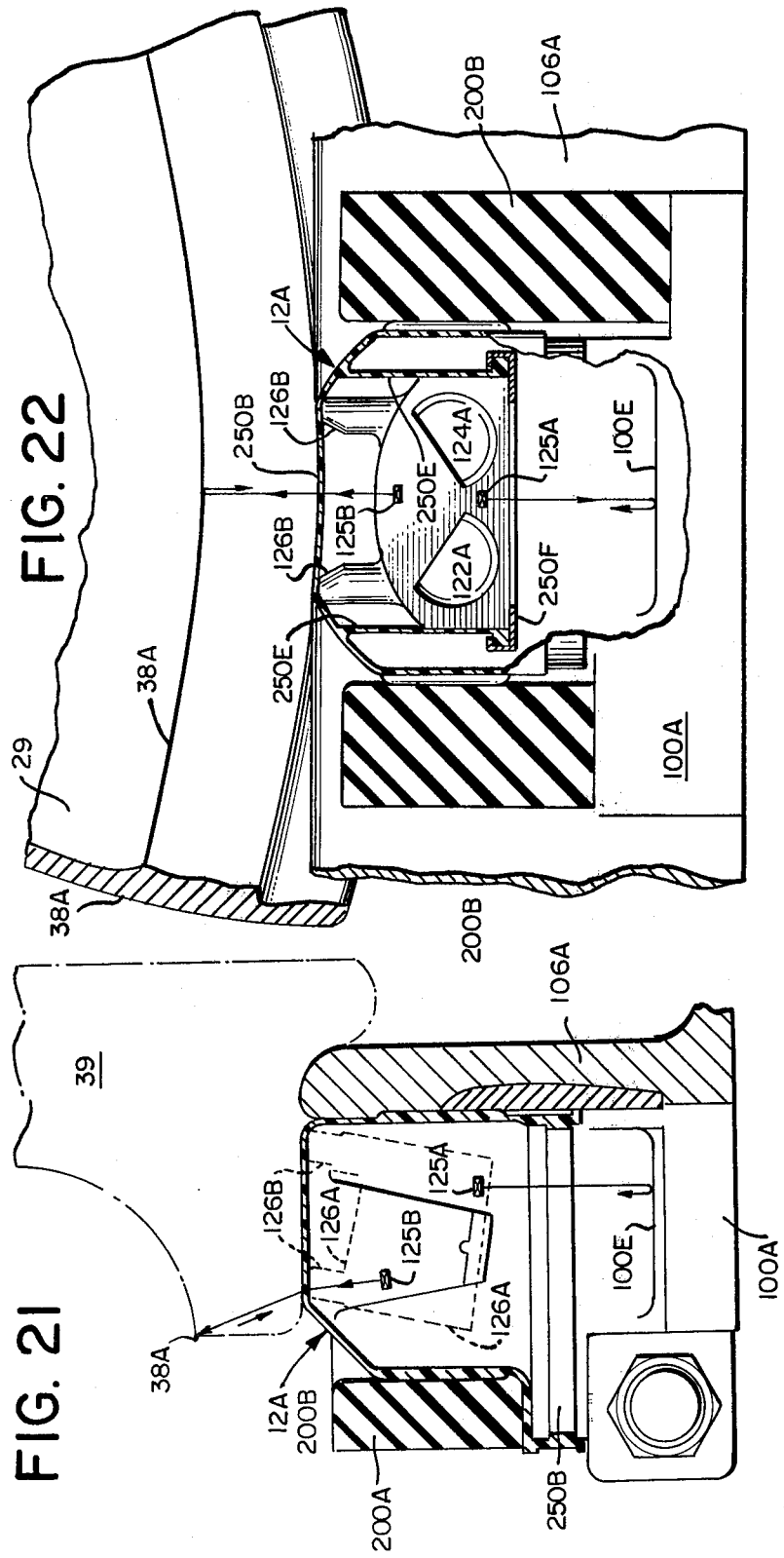

METHOD AND APPARATUS FOR TESTING WEAR, SIZE AND RESIDUAL STRESS CONDITIONS

CROSS-REFERENCE

This application is a continuation-in-part application of the previous inventors' patent application relating to Method and Apparatus for Testing Wheels and Defect Detection in Wheels filed Nov. 17, 1971 and bearing Ser. No. 199.487 now U.S. Pat. No. 3,812,708.

BACKGROUND OF THE INVENTION

1. Field of the Invention

This invention relates to wear measurement and defect detection in wheels. More particularly, this invention relates to ultrasonic testing of metallic railroad wheels or defects and excessive wear. The testing is accomplished in-track on moving wheels.

It is well known that wheel failures due to either exteme wear or defects, such as thermal cracks, are a major cause of train derailments. Therefore, it is highly desirable to sidetrack rolling stock having defective or excessively worn wheels, and to repair or replace such wheels before the tragedy of a derailment occurs.

It is also well known that tire failures in vehicles such as trucks, busses, automobiles and aircraft are a cause of serious accidents, resulting in great personal injury and property damage. Effective methods and apparatus for regularly and accurately testing tires are, therefore, also very desirable.

Prior Art

No satisfactory automated means capable of testing railroad wheels on rolling stock for wear or defects presently exists. Defective railway wheels are currently located by trained inspectors who visually check for cracks in the running surface, flange and plate sections of each wheel when it is stationary in a railway yard. Though many defective wheels are found in this manner, many more escape detection due to other equipment, such as brake shoes, journal boxes, etc., obscuring the inspector's field of view. Also small or subsurface defects are difficult for an inspector to find. Measurement of wheel wear is also performed at such times by physical placement of a gauge which measures the height of the flange above the running surface of wheel, an altogether inefficient process.

Magnetic testing of locomotive wheels has also been performed by mounting small detector coils on the locomotive in close proximity to the wheels. Small cracks, such as thermal cracks, which may develop when the locomotive is in motion disrupt the magnetic field, thereby triggering an alarm signal. This method of testing wheels is impractical because of the expense and difficulty of installing and maintaining magnetic testing apparatus at each wheel on each railway car. Furthermore, no provision for measurement of wheel wear is made in such devices.

Other currently known means of inspecting wheels more extensively all require that wheels and axle sets be removed from the railroad car for testing. These means include inspection of wheels by ultrasonic contact or by magnetic particle inspections. Although these inspection methods are quite effective, it is not feasible to regularly remove every wheel from a railroad company's entire rolling stock. Furthermore, freight trains are usually assembled at marshalling yards or division points, from cars owned by different railroad companies. It is desirable for an individual railroad company to quickly and accurately examine the wheels of such cars before including them in a train. Yet, it would be totally impractical to thoroughly check the wheels of each car by presently known methods when assembling a freight train, and visual inspection alone is too time consuming and inaccurate to suffice.

Railway cars or locomotives whose wheels are found to be defective or excessively worn are removed from service. Depending on the nature of the defect or wear, wheels or axle sets of wheels are replaced, or in some cases the vehicle is sent to a wheel truing machine to re-establish a correct wheel profile.

Similarly, no automated means for testing tires of trucks, busses, automobiles, and aircraft is currently available. Detection of defective tires is limited to visual inspection, and such inspection often does not disclose damage to the tire casing, including breaks in the reinforcing tire cord,

SUMMARY OF THE INVENTION

An object of the invention is to provide economical and highly effective methods and apparatus for the detection of defects in wheels.

Another object of the invention is to provide methods and apparatus to detect excessive wear of wheels.

A further object of the invention is to provide methods and apparatus for testing wheels for defects and wear, and to certify that testing has been performed.

An additional object of the invention is to provide methods and apparatus for testing for defects and wear in railroad wheels mounted on moving cars and locomotives.

A still further object of the invention is to provide methods and apparatus for testing wheels for defects and wear without disrupting the usual and normal marshalling of railroad cars and patterns of train movement.

Another object of the invention is to provide methods and apparatus for identifying potentially explosive wheels suffering from "residual stress" conditions.

A further object is to provide improved shielded transducers and transducer supporting assemblies within flexible couplant boots providing maximum test times for moving wheels, actuated by wheel sensors responding to wheels approaching from either direction.

Wheel testing apparatus according to the invention comprises at least one search unit positioned in-track replacing a cut away portion of a rail. The search unit has a thin vertical rail positioned in the removed portion of rail and aligned with the gauge edge of the remaining rail, thereby providing support for passing railroad wheels. The thin vertical rail supports a wheel rolling thereover adjacent to its flange, and thereby exposes most of the running surface of the passing wheel to a test zone in the cutaway portion of the rail adjacent to the thin vertical rail positioned therein. Test equipment positioned in this zone does not alter or intrude into the normal path of the wheel.

Each search unit has two tungsten-filled, urethane-casing-backed transducers mounted in a lightweight micro-balloon-filled shielding mask supported in an upwardly springed-biased parallel-axis gimbal suspension system. The transducers, mask, and gimbal suspension system are enclosed in a flexible fluid-filled boot and are positioned adjacent to the thin vertical rail in the test zone, the fluid-filled boot provides a good acoustic path from the transducer to the running surfaces of passing wheels. Two positioning arms upstanding from the gimbal suspension system engage the running surface of each passing wheel and align the longitudinal axes of the transducers with the running surface, maximizing delivery of ultrasonic energy thereto.

One of the transducers is held in the mask with its sonic axis inclined with respect to a plane tangent to the running surface of the wheel positioned on the search unit. The angle of inclination is determined by Snell's Law. Ultrasonic energy pulses delivered along the sonic axis into the wheel are refracted substantially tangent to the wheel and thereafter travel about its peripheraly in a first direction. The second transducer, also held in the mask, is opposed to the first transducer, i.e. with its sonic axis also inclined with respect to the running surface wherein pulses produced by the second transducer are delivered into the wheel and refracted substantially tangent thereto, and travel about the wheel's periphery in the opposite direction.

The ultrasonic energy pulses used for testing herein have a relatively low frequency below 1,000 KHz, and preferably 400 KHz. These pulses achieve a deep penetration of ultrasonic energy into the wheel. the ultrasonic energy pulse tends to migrate toward the surface of the wheel as it travels there about concentrating a surface wave component immediately adjacent to the running surface. A portion of the wave also migrates to the larger diameter flange of the wheel and travels thereabout.

Positioning of the transducer in the mask as described above causes a portion of the pulse circling the wheel and passing the boot-wheel interface to be refracted through the coupling fluid in the boot to impinge upon the transducer to the sending transducer. A defect in the running surface of the wheel causes a portion of the pulse to be reflected back along the periphery of the wheel as to defect echo pulse. A portion of that defect echo pulse is refracted out of the wheel at the boot-wheel interface to impinge upon the sending transducer, indicating the presence of a defect.

As a wheel approaches the search unit, the transducer facing the direction of approach is repetitively pulsed at an interval greater than the time necessary for the pulse to travel about the largest diameter wheel to be tested. When the wheel contacts the search unit, an ultrasonic energy pulse is introduced into the running surface thereof, and travels about the wheel to return to the boot-wheel interface, whereat a portion of the pulse is returned from the wheel to the second transducer. This confirms the presence of the pulse in the wheel and halts further pulsing of the first transducer. The returned pulse is also used to adjust the amplified gain of the output of the first transducer, which is being monitored for defect echo pulses, wherein the signal caused by the defect echo pulses is amplified to a usable strength. The travel time of the pulses about the periphery of the wheel is measured to indicate the wheel size.

After substantial attenuation of the first pulse in the wheel, the functions of the two transducers are reversed, and the wheel is further tested by pulsing the second transducer to produce an ultrasonic energy pulse traveling about the periphery of the wheel in the opposite direction. The second transducer is preferably pulsed in synchronism with the attenuating through-transmission pulses remaining in the wheel. The sending transducer is monitored for defect echo pulses. A wear measurement is made by measuring the time interval between the time for the pulse to travel about the periphery of the running surface and the time for the pulse to travel about the larger diameter flange.

For testing wheels moving at high speeds wherein the wheel passes the search unit prior to delivery of the second pulse, a second, closely spaced parallel operating search unit is provided. Testing in the second direction is accomplished as the wheel passes thereover.

The wheel testing apparatus further comprises gauging means for gauging approaching wheels, switch means sensing the direction of approach of wheels, coupling fluid spray means for wetting the surface of the flexible boot for better ultrasonic coupling at the boot-wheel interface, and an electronic test circuit for operating the transducers in the above-described manner. A unique feature of the test circuit comprises getting all through-transmission pulses into one channel and all defect echo pulses into a second channel so that the amount of circuitry is minimized. Outputs from the electronic test circuit include a defect alarm signal, an excessive wear alarm signal, a wheel size indication, and a test certification signal. These outputs trigger pressurized color-coded paint sprays for marking the wheels if they are passing at low speed, or terminals for connection with automatic car identification systems for recording information relating to wheels passing at either low or high speed.

A second wheel testing apparatus is preferably installed in the opposite rail of the track for testing remaining wheels on the otherside of the train.

The absence of a certification signal, signifying a failure of a tested wheel to accept any significant amount of vibratory energy, is employed to identify potentially explosive wheels suffering from high residual stress conditions, permitting such wheels to be removed before explosive cracking causes a serious accident.

THE DRAWINGS

FIG. 8 is a vertical side cross-sectional view of a portion of the gimbaled suspension means and the transducer carrying mask having two transducers mounted therein, with a wheel positioned for testing.

FIG. 9 is a schematic side elevation view of a wheel positioned over a search unit for defect testing.

FIG. 10 is a timing diagram indicating the operation of the two transducers of FIG. 9.

FIG. 11 is a similar schematic view of a wheel positioned on a search unit for testing.

FIG. 12 is a timing diagram indicating the operation of the transducers of FIG. 11.

FIG. 13 is a similar schematic view of a wheel moving across two search units for high speed testing.

FIG. 14 is a timing diagram indicating the operation of the transducers of FIG. 13.

FIG. 15 is a similar schematic view of a wheel positioned on a search unit for wear testing.

FIG. 16 is a timing diagram indicating the operation of the two transducers of FIG. 15.

Figure 17B:
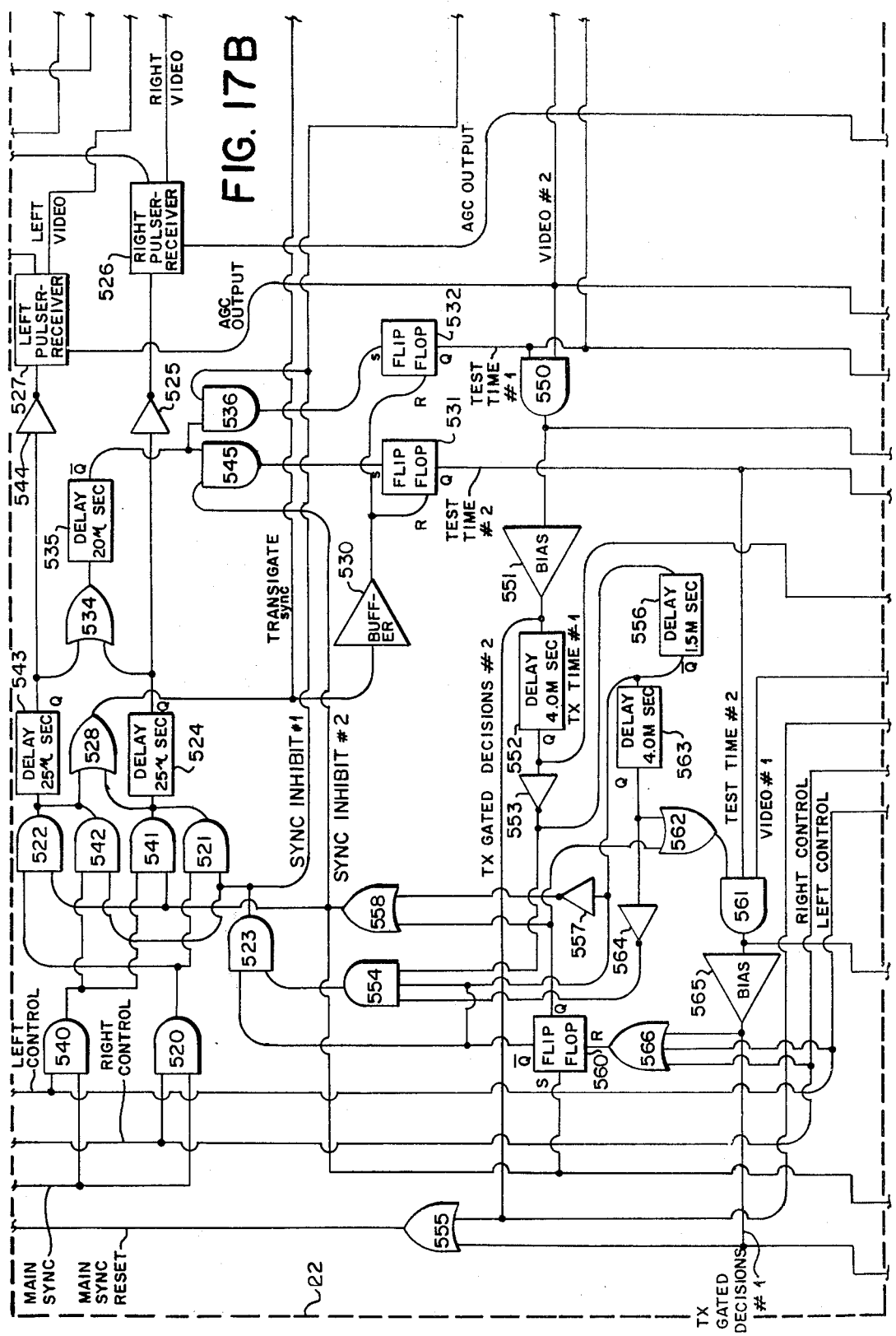
FIG. 17 illustrates the placement of FIGS. 17A–E to comprise an electrical circuit diagram.
Figure 17D:
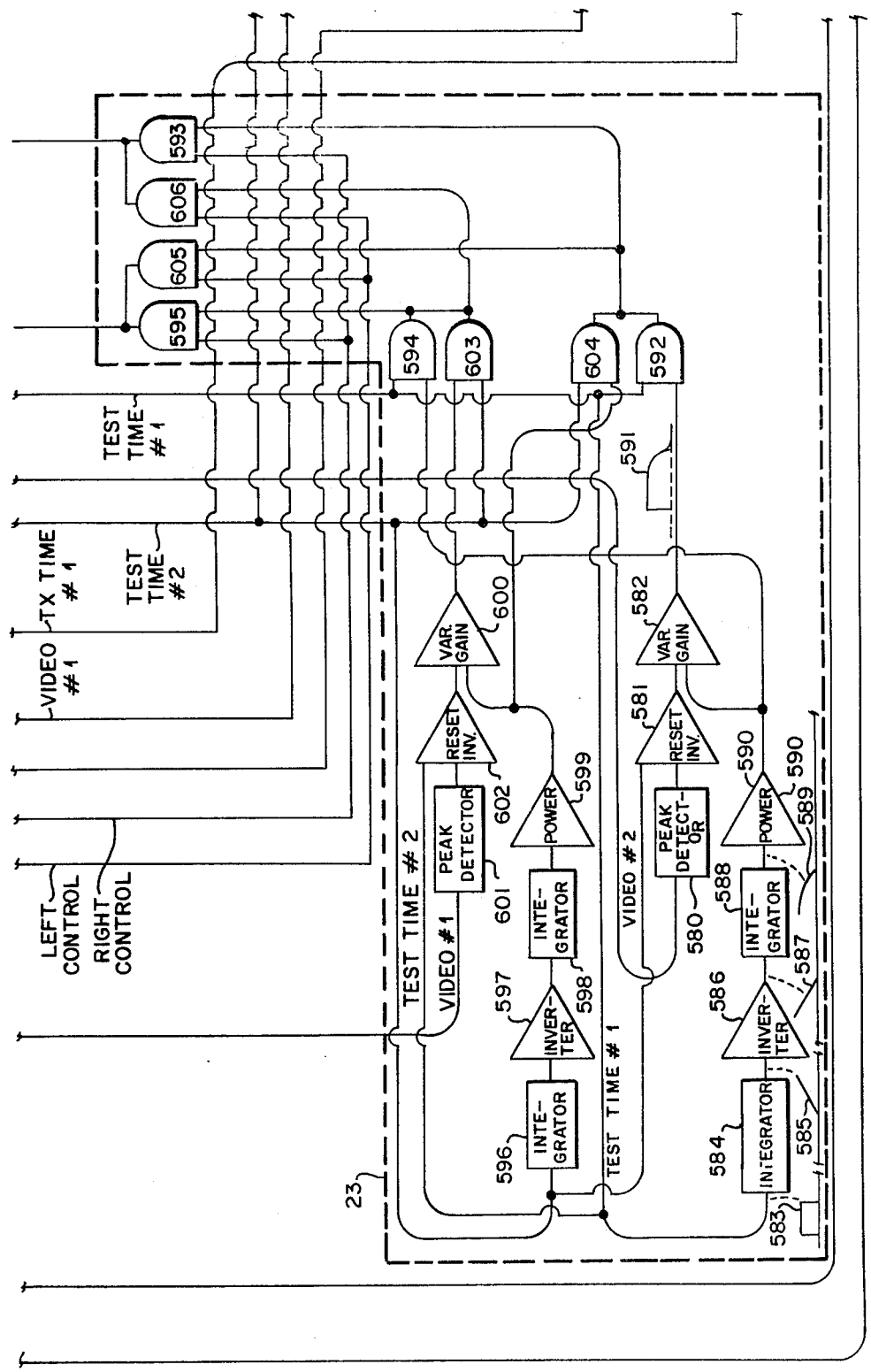
Figure 17E:
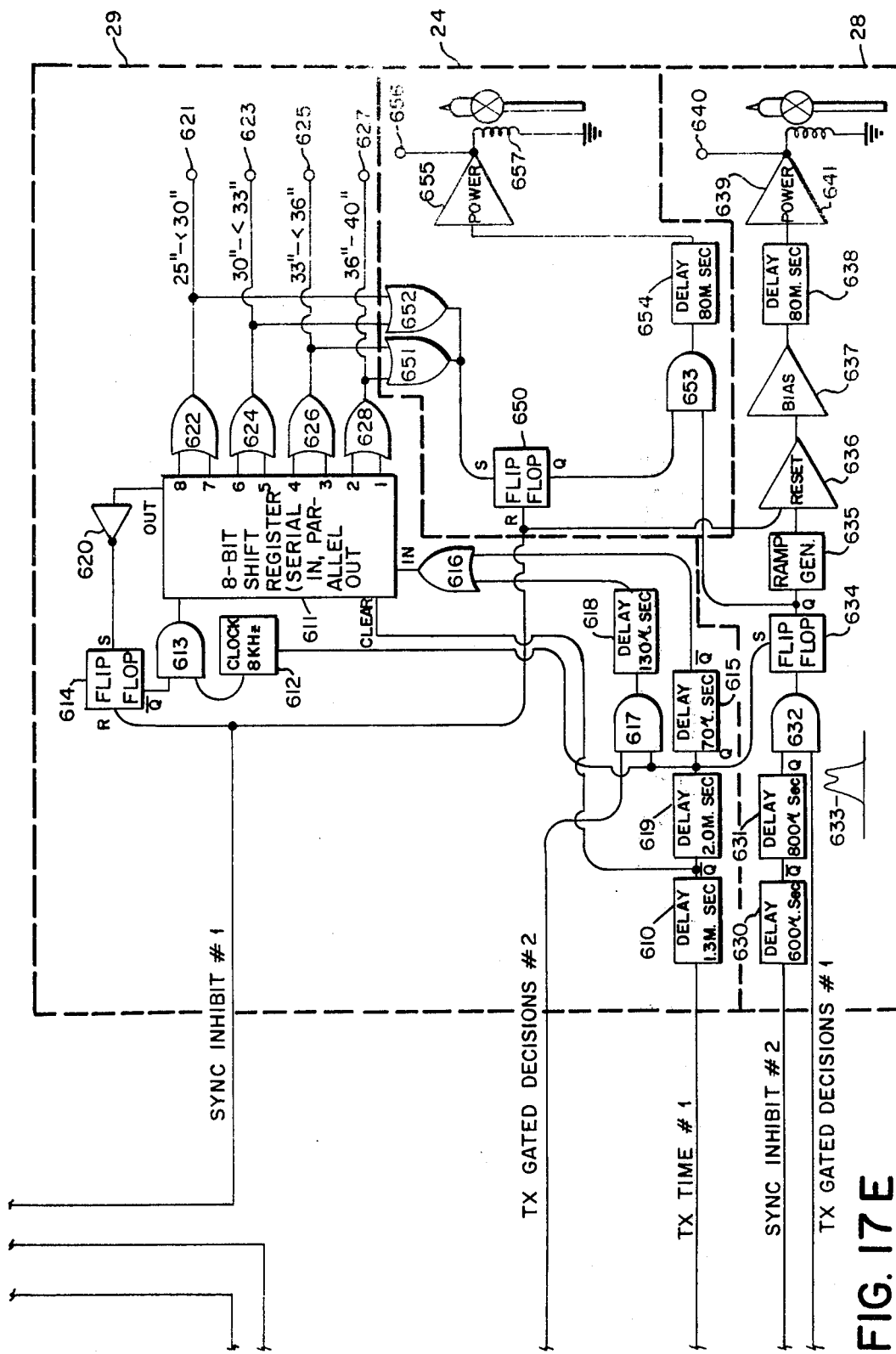

FIGS. 17A–E are portions of an electrical circuit diagram comprising FIG. 17.

Figure 18A:
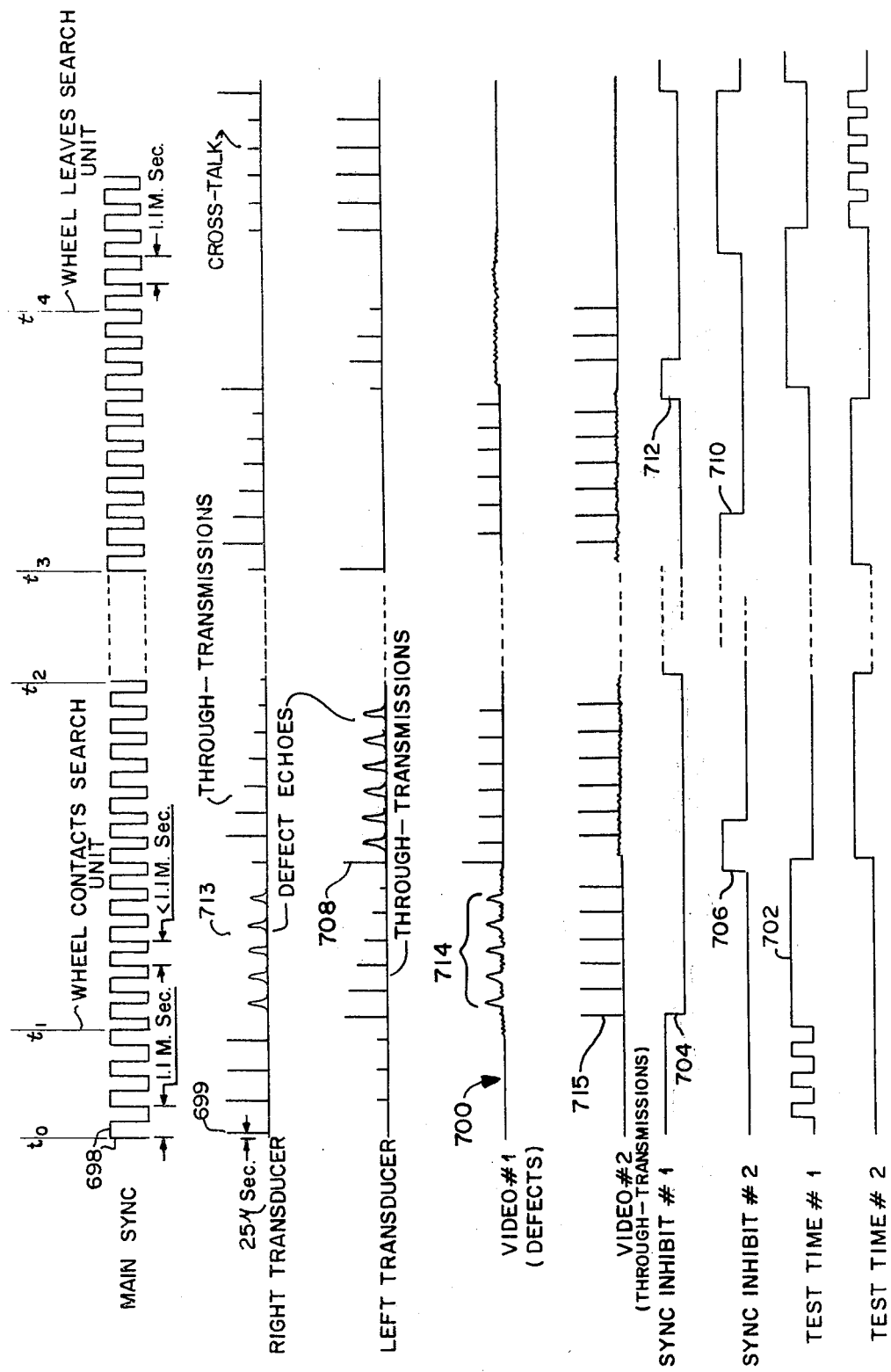

FIG. 18 illustrates the placement of FIGS. 18A–B to comprise a timing diagram of the operation of the electrical circuit shown in FIG. 17.

FIGS. 18A–B are portions of the timing diagram of FIG. 18.

Figure 19:
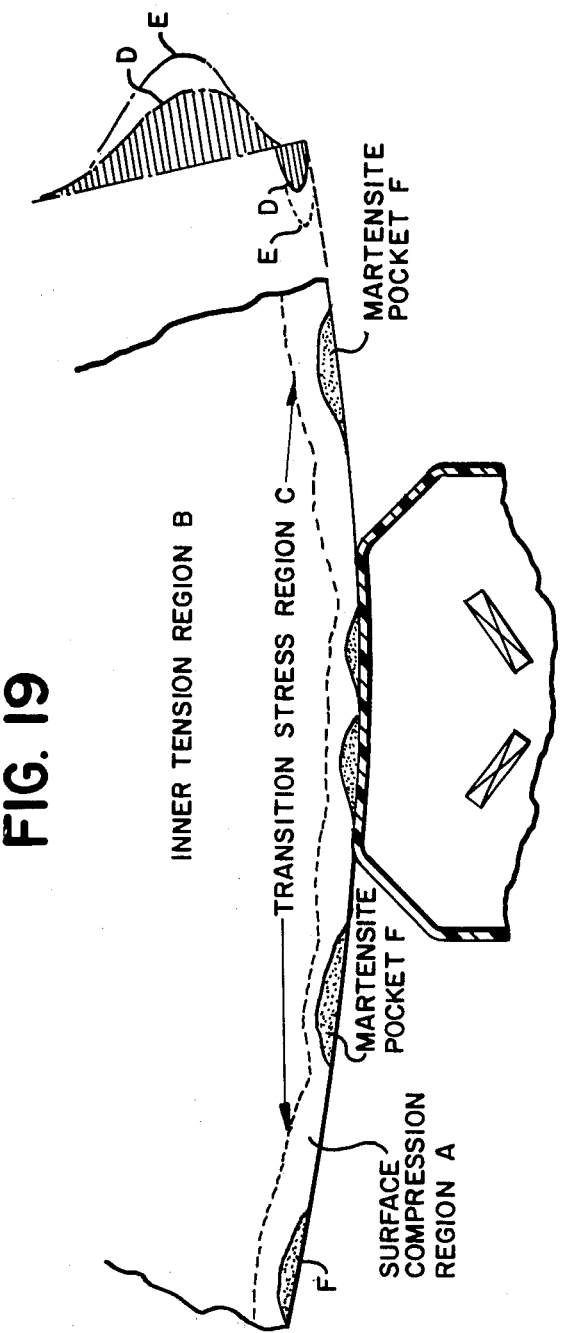

FIG. 19 is a schematic fragmentary cross-sectional side elevation view of a potentially explosive wheel suffering from a residual stress condition, easily identified by the invention.

The same numbers refer to the same elements throughout the various FIGURES.

Figure 20:
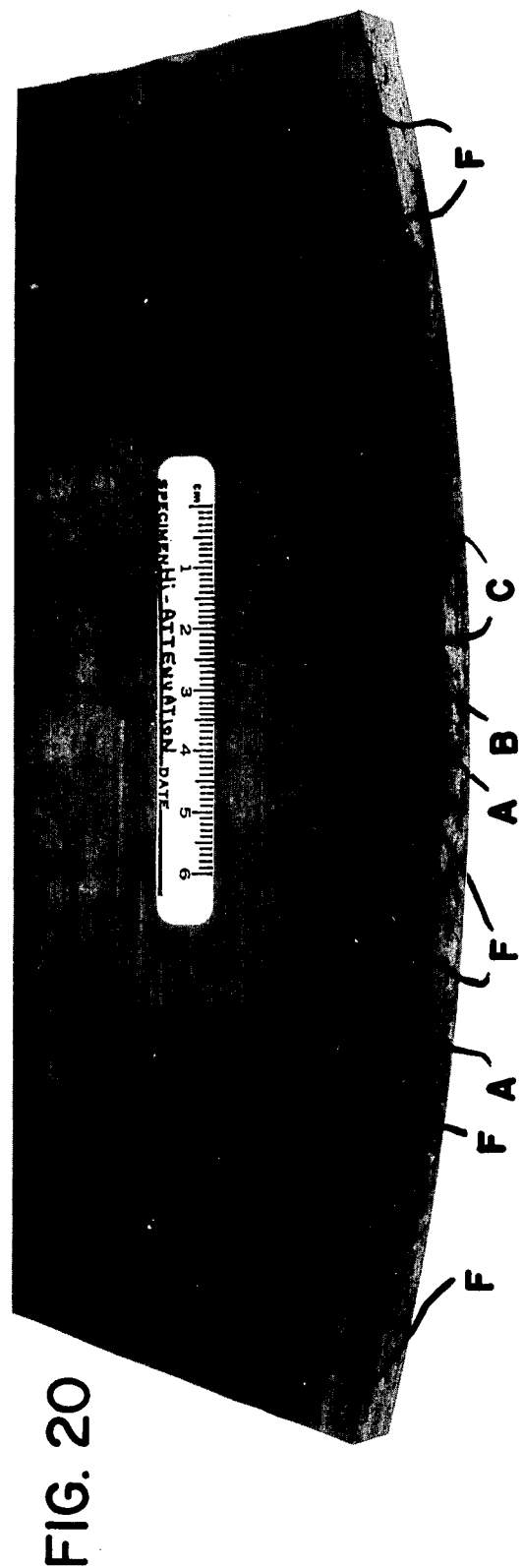

FIG. 20 is a corresponding cut out segment of a residual stress wheel identified by the "calamity alarm" system of the present invention, etched to show the grain structure and characteristic transition stress line typifying a residual stress wheel.

FIG. 21 is a fragmentary cross-sectional elevation view taken on a transverse plane through the test unit of the present invention showing the position and operation of a tilted upwardly directed transducer employed to monitor wheel rim thickness to identify excessively worn wheels, and a downwardly directed "depth sounder" transducer employed to confirm physical wheel contact with the test unit.

FIG. 22 is a corresponding fragmentary cross-sectional side elevation view of the test unit in contact with a passing wheel rolling along the support rail and depressing the flexible couplant boot, also showing the upwardly directed worn wheel alarm transducer and the downwardly directed wheel contact transducer.

Figure 23:
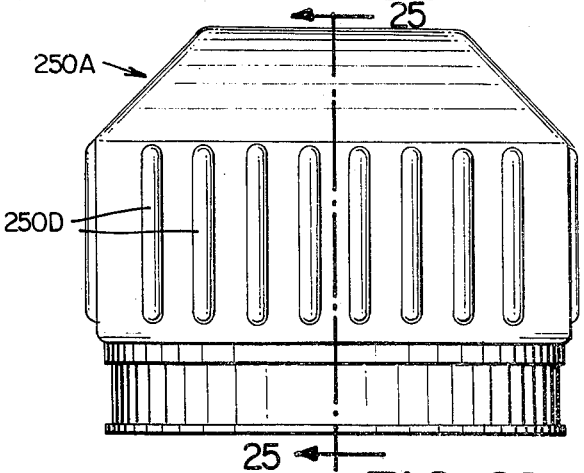

FIG. 23 is a corresponding side elevation view of the flexible couplant boot.

Figure 24:
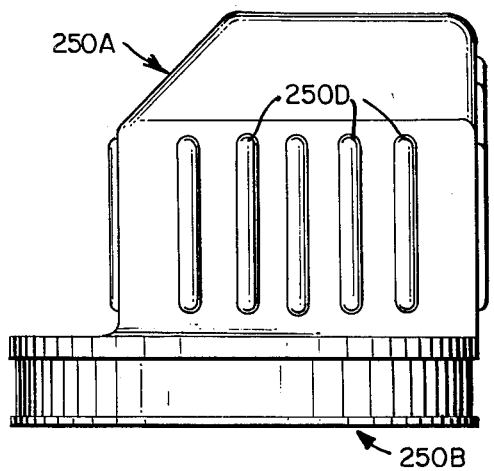
Figure 25:
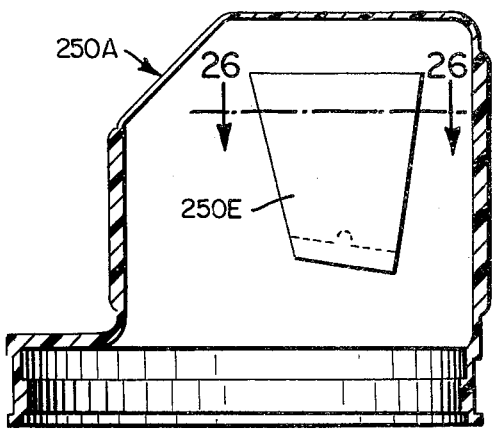

FIG. 24 is an end elevation view of the flexible couplant boot;

FIG. 25 is a cross-sectional end elevation view taken along the plane 25—25 shown in FIG. 23, showing the hollow concave cavity within the flexible boot as well as an integral depending flange supporting the transducer mask assembly.

Figure 26:
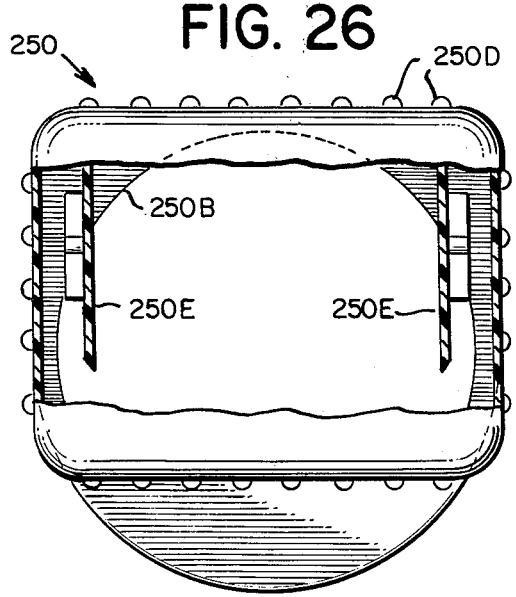

FIG. 26 is a cut-away top plan view partially in section taken along the line 26-26 shown in FIG. 25, showing the integral depending flanges inside the couplant boot.

Figure 27:
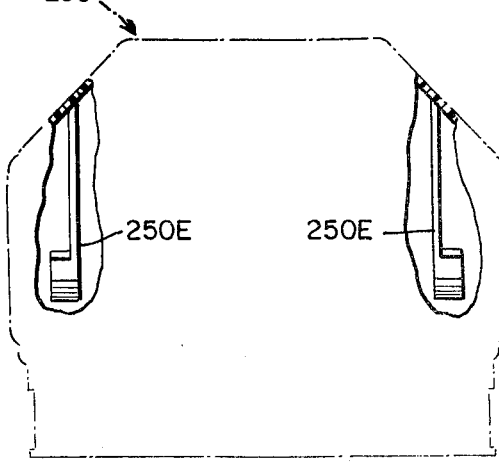

FIG. 27 is a fragmentary cut-away side elevation view showing the couplant boot in outline with the integral depending transducer mask supporting flanges being exposed to view.

Figure 28:
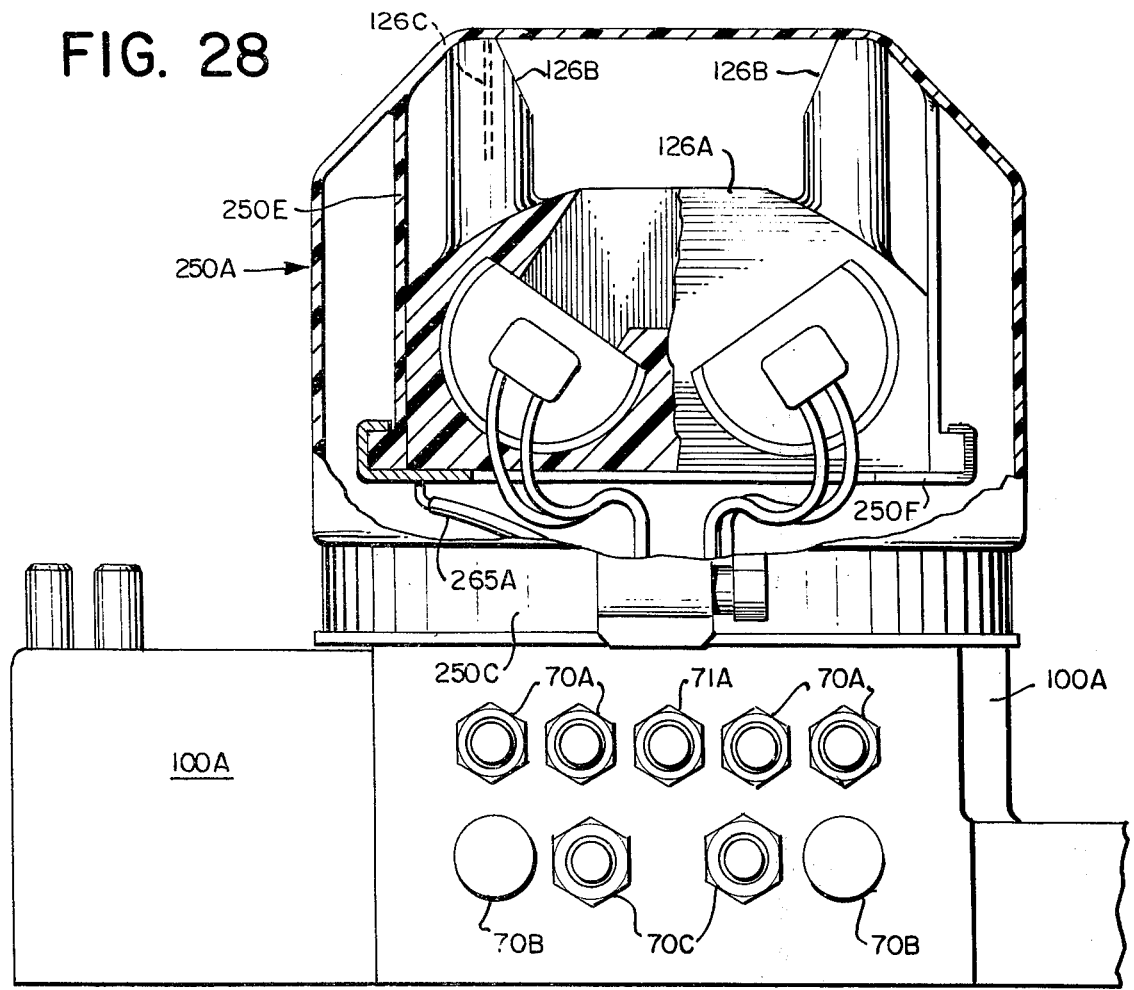

FIG. 28 is an enlarged fragmentary side elevation view of the test unit couplant boot and supporting base, showing the positioning of the transducer mask suspended by the integral depending flanges as well as transducer connector leads, heaters, and thermostats.

Figure 29:
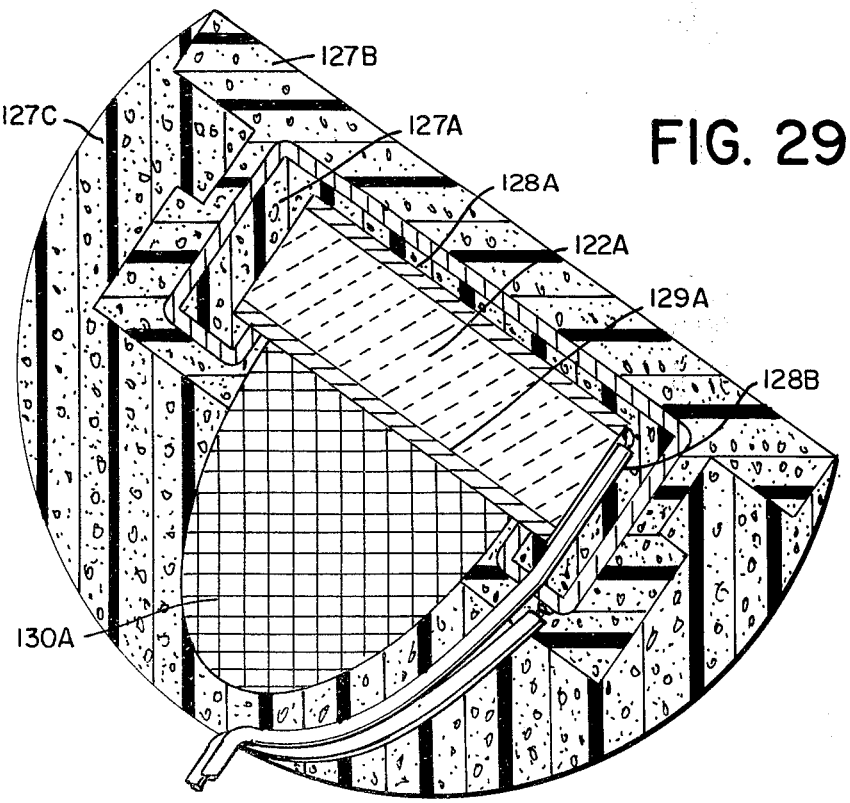

FIG. 29 is a greatly enlarged cross-sectional view of one of the wheel testing transducer units shown in FIG. 28, illustrating the construction thereof with a radiation-shielding conductive layer substantially completely enclosing the transducer crystal.

Figure 30:
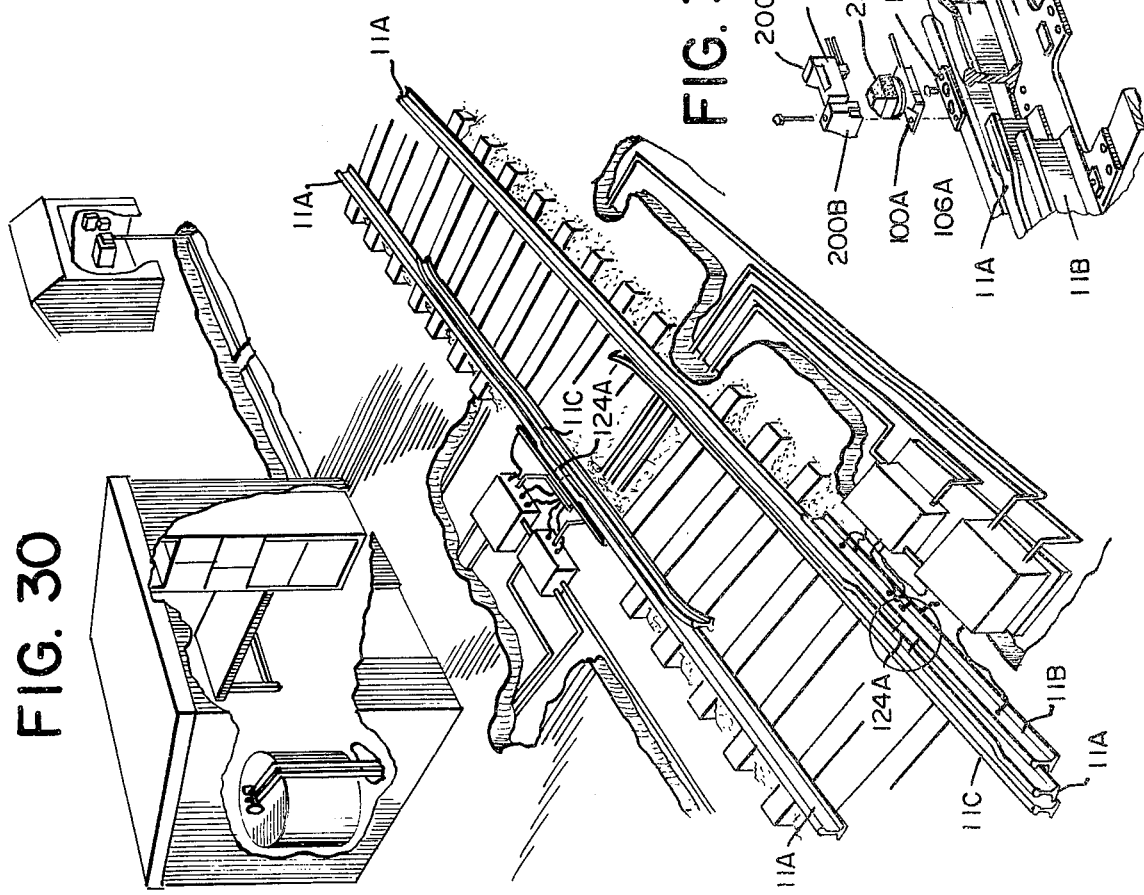

FIG. 30 is a diagrammatic perspective view of a wheel test system incorporating two in track search units positioned at longitudinally spaced apart locations in the two traffic carrying rails of a railroad track, showing the associated guard rails and support system.

Figure 30A:
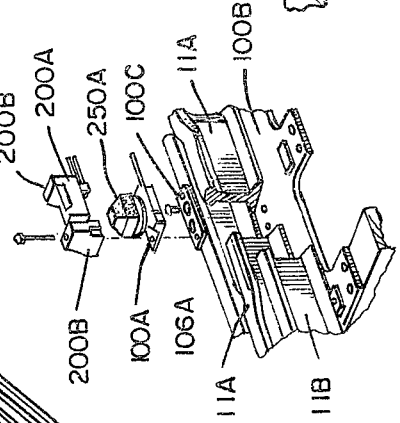

FIG. 30A is a fragmentary, enlarged, exploded view of the search unit assembly encircled in the lower portion of FIG. 30.

Figure 31A:
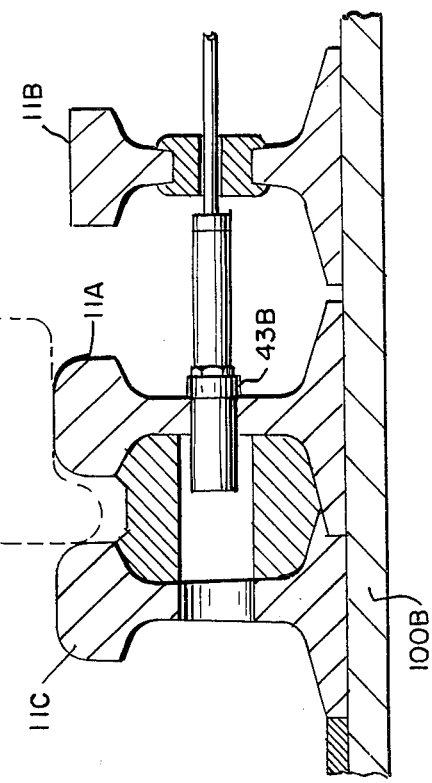
Figure 31B:
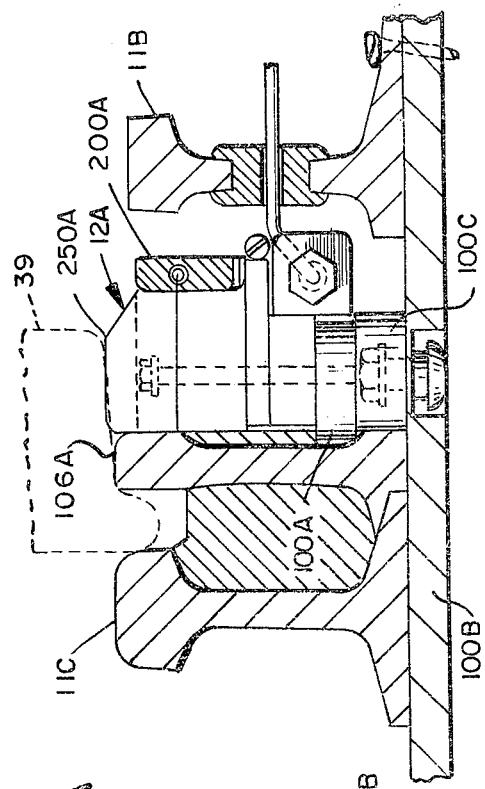
Figure 31:
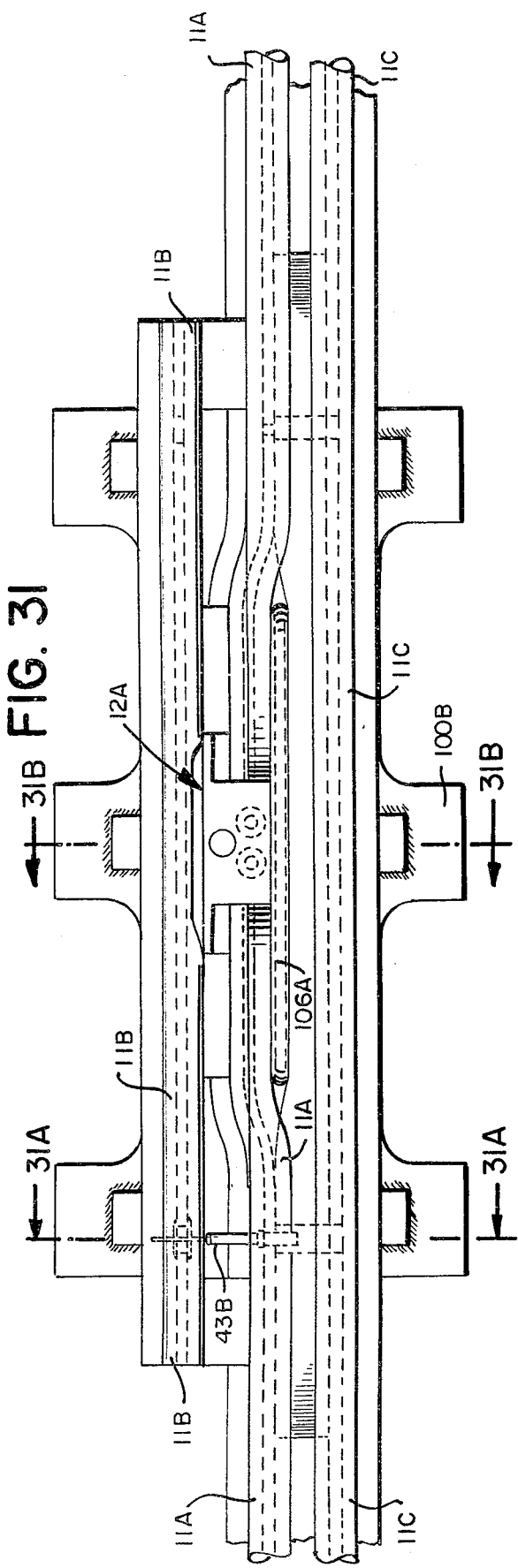

FIG. 31 is a fragmentary top plan view of a search unit assembly showing the running rails, guard rails, and field rails provided for a sturdy wheel testing installation.

FIGS. 31A and 31B are respective enlarged cross-sectional views of the rail testing assembly shown in FIG. 31 taken along the planes 31A and 31B shown therein, and respectively illustrating a wheel approach sensor and the wheel test unit itself.

Figure 32:
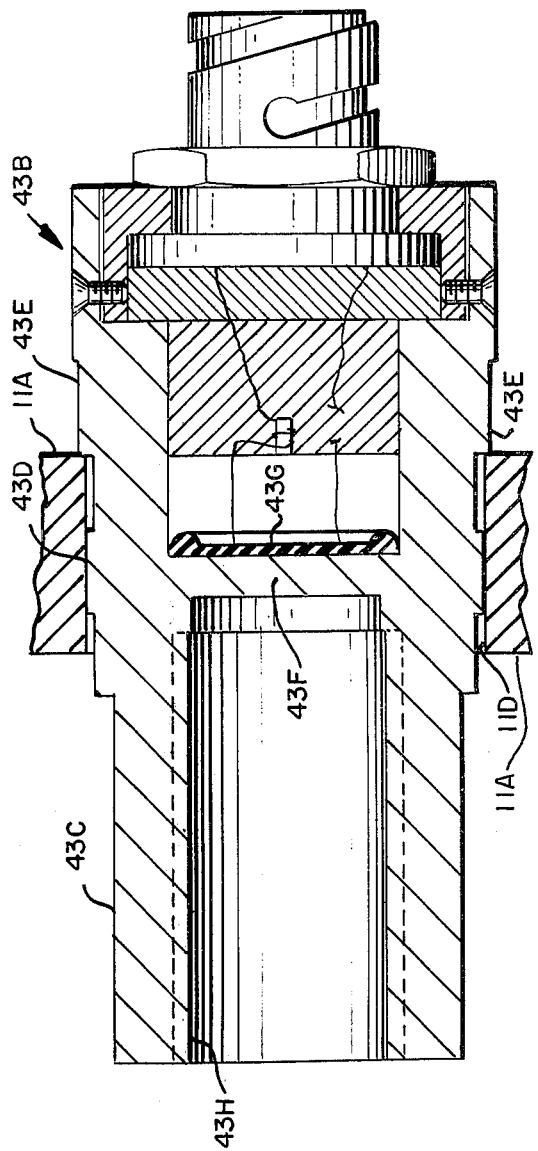
Figure 33:
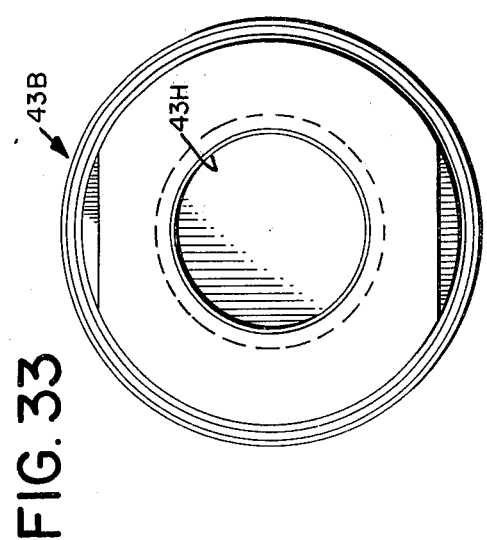

FIG. 32 is a greatly enlarged cross-sectional elevation view of the wheel approach sensor employed in a preferred embodiment of the present invention; and FIG. 33 is an end elevation view of the sensor shown in FIG. 32.

PREFERRED EMBODIMENTS

Figure 1:
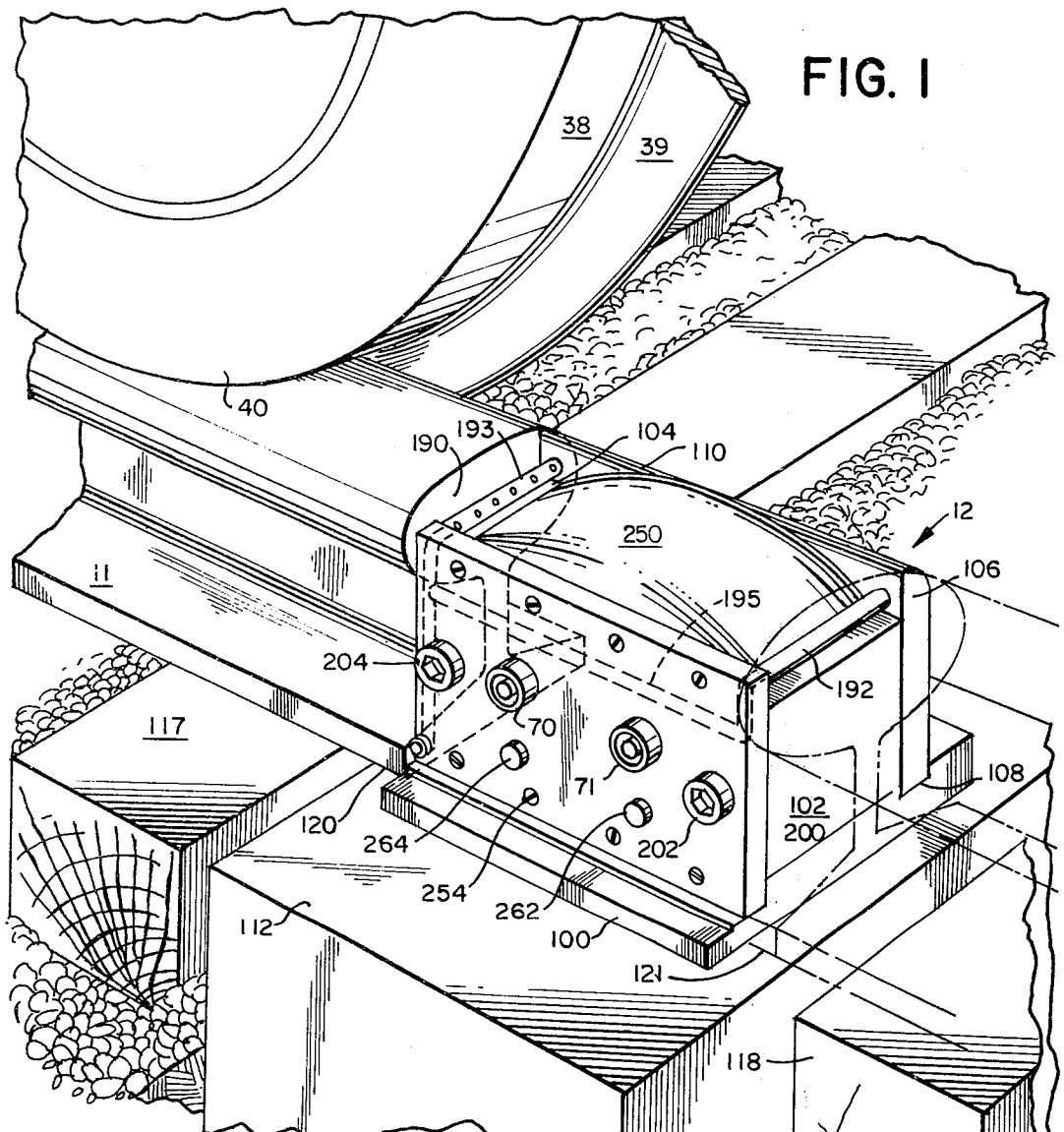
FIG. 1 is a perspective view of a search unit according to the invention mounted in a rail for testing an approaching wheel.
Figure 3:
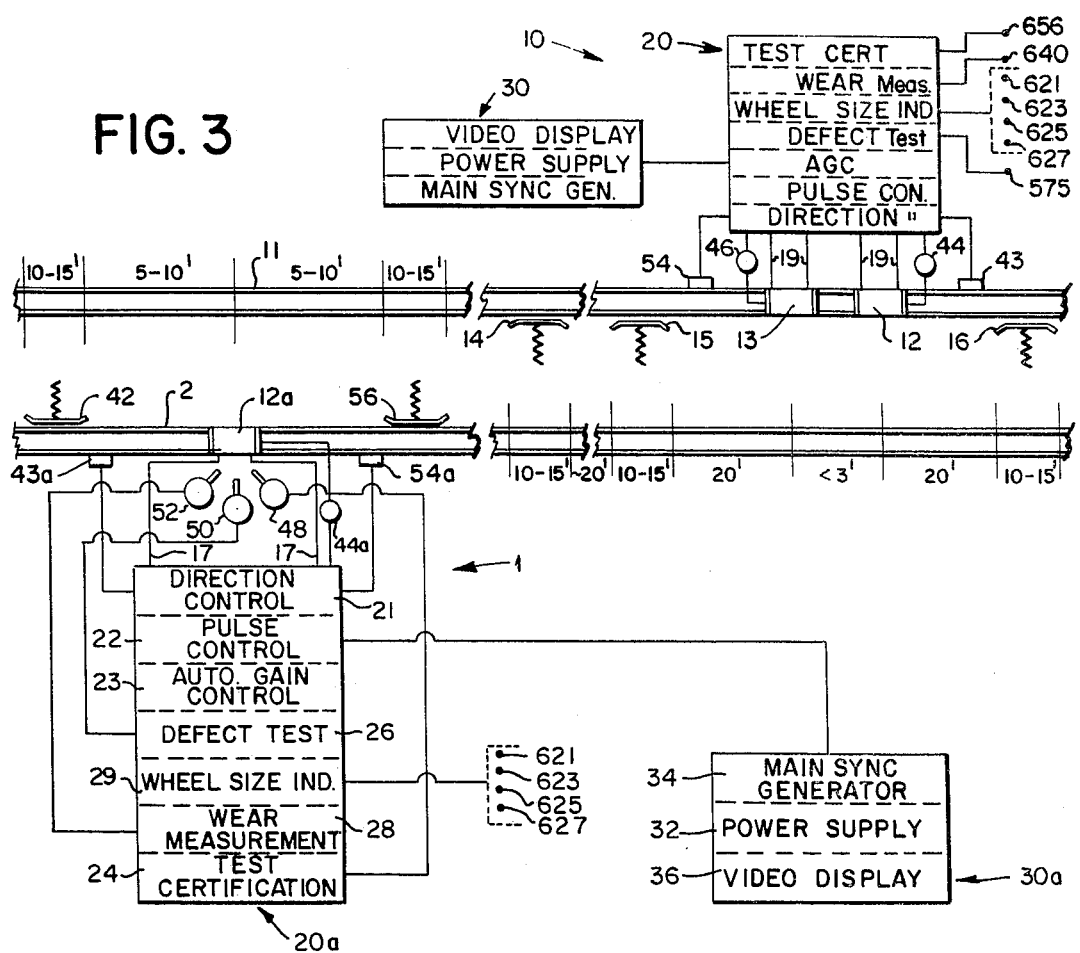
FIG. 3 is a top plan schematic view of wheel testing apparatus for both low and high speed testing.

Two wear measurement and defect detection systems adapted for testing railroad wheels on moving trains are shown in FIG. 3. A first test system generally indicated at 1, is particularly adapted for testing wheels moving at relatively low speeds of less than 30 m.p.h., and usually at speeds of 5–10 m.p.h. such as are encountered in hump yards or marshalling yards. The test system 1 generally comprises a search unit 12a positioned in-track, as shown in FIG. 1. The search unit 12a houses two ultrasonic transducers in a shielding mask which is mounted in a spring-biased parallel-axis gimbal suspension system for aligning the transducers with the running surface 38 of wheel 40, wherein the transducers can introduce an ultrasonic energy pulse into the wheel and monitor ultrasonic energy pulses returning from the wheel, as will be more fully described below.

Referring again to FIG. 3, search unit 12a is connected by coaxial cables 17 with an electronic test circuit 20a having a direction control portion 21, a pulse control portion 22, an automatic gain control portion 23, a test certification portion 24, a defect test portion 26, a wear measurement portion 28, and a wheel size indicator portion 29. Connected to the electronic test circuit 20a is a support unit 30a containing a power supply 32, a main sync generator 34, and a video display 36.

As a wheel 40 approaches search unit 12a from the left in FIG. 3, it is engaged by a gauging device 42 which consists of a C-shaped metal member approximately 10–15 feet long mounted adjacent to and spring biased toward the inside or "gauge" side of rail 2. The gauging device 42 positions the running surface 38 of wheel 40 centrally on top of rail 2 by engaging flange 39 of the wheel and urging the flange into contact with the inside of the rail. It is desirable to have the running surface positioned in this manner for testing.

After being gauged the wheel 40 next contacts a switch 43a which indicates to the electronic test circuit 20a the direction from which the wheel is approaching.

Contact with switch 43a also causes operation of a coupling fluid spray dispenser 44a.

As the wheel passes over search unit 12a it is tested. The test certification portion 24 of the electronic test circuit 20a determines if testing of the wheel has been accomplished, and triggers a pressurized certification paint spray dispenser 48 to provide a visual record thereof on the wheel.

If a defect is discovered by the test, the defect test portion 26 of the electronic test circuit triggers operation of a defect paint spray dispenser 50 to mark the defective wheel. Similarly, the wear measurement portion 28 of the electronic test circuit 20a causes an excessive wear paint spray dispenser 52 to mark the worn wheel. The wheel size indicator portion 29 of the electronic test circuit provides an output on one of terminals 621, 623, 625, or 627 wherein the size of the wheel being tested is indicated.

Referring still to FIG. 3, the wheel 40 next passes over a switch 54a indicating that the wheel has passed the search unit 12a.

If wheel 40 were approaching search unit 12a from the opposite or right hand direction, the wheel would be first gauged by a gauging device 56, and pass over switch 54a indicating to the direction control portion 21 of the electronic test circuit 20a that the wheel is approaching from the left. The coupling fluid spray dispenser 44a would also be activated.

To test wheels on the opposite side of the train, a second wheel testing system similar to system 1 described above would be positioned in the opposite rail 11. The distance between such a second test system and system 1 would preferably be in excess of 50 feet. This distance is necessary because the wheels of the train are to be gauged against the inside of rail 11, and therefore the two gauging units are working in opposition on a very heavy mass. If the test systems including the gauging devices are located too closely together, proper gauging will not occur.

A wear measurement and defect detection system 10 adapted for testing wheels of trains moving at relatively high speeds up to 60 m.p.h. is also shown in FIG. 3. The system 10 generally comprises two search units 12 and 13, each positioned in-track in rail 11, the two search units being separated by not more than 3 feet. The 3 foot limitation on separation of the search units is desirable because the axle centers on some tandem wheel cars are 6 feet or less apart, and wider separation of the search units could therefore result in confusion as to the particular wheel being tested.

Search units 12 and 13 are connected by coaxial cables 19 to a second electronic test circuit 20 and associated support circuitry 30. The electronic test circuit 20 is identical to test circuit 20a used for the low speed test system 1, except that an output terminal 656 is provided for the test certification system, an output terminal 640 is provided for the wear alarm from the wear measurement portion, and an output terminal 575 is provided for an alarm signal from the defect test portion. These output terminals may be connected to an automatic car identification system or hot box detector read-out wherein a written record of wheels tested or wheels needing replacement or repair can be provided.

The high speed test system 10 also tests wheels moving at low speeds, and paint spray dispensers could be provided to mark slowly moving wheels. However, paint spray dispensers are not practical to mark wheels moving at high speeds.

As a wheel 40 approaches search units 12 and 13 from the left in FIG. 3, it is engaged by a first gauging device 14 and subsequently by a second gauging device 15, both similar to gauging device 42 described above. The gauging devices operate to urge the flange of the wheel into contact with the inside rail 11, and two gauging devices are necessary because of the high speed of the train. the gauging devices may be separated by approximately 20 feet. The separation between gauging device 15 and the search unit 13 may also be about 20 feet.

As the wheel approaches search unit 13 it passes over a switch 54 indicating to the electronic test circuit the direction of approach of the wheel, and operation of coupling fluid spray dispensers 44 and 46 are thereby triggered. The wheel passes over search units 12 and 13 for testing, and then operates switch 43 which signals the electronic test circuit that the wheel has passed.

If the wheel 40 were approaching from the right in FIG. 3, it would similarly be gauged by a first gauging device (not shown) and a second gauging device 16, and subsequently pass over the switch 43 indicating the direction of approach and triggering operation of the coupling fluid spray units 44 and 46. Gauging device 16 may also be positioned approximately 20 feet from search unit 12.

Testing of the wheels on the opposite side of a high speed train is accomplished by providing a similar test system 10 positioned in the opposite rail. The two test systems are positioned so that there is approximately 200 feet between the opposite-acting gauging devices, thereby minimizing the problem of regauging wheel and axle sets against the opposite rail.

SEARCH UNIT

The search units 12–13 comprise the interface between the electronic test circuit 20 and the railroad wheel being tested. They also comprise a rail adapted for supporting passing wheels wherein many tests can be performed.

Referring now to FIG. 1, a portion of the rail 11 is cut away, and search unit 12 is mounted in the resulting space. The search unit 12 comprises first a flat base plate 100 having upstanding therefrom two vertical flanges 102 and 104 disposed generally transverse to rail 11. The base plate and the upstanding flanges are cast of strongly ribbed nickel alloy steel.

A thin sturdy rail 106 is seated on the base plate 100 at 108 and is further attached to the base by bolts threaded into flanges 102 and 104. The thin rail 106 has a curved top surface 110 which bridges the gap in rail 11 and provides a support adjacent to the flange of wheels passing over the search unit. thus, the running surface 38 of wheel 40 is exposed to a test zone comprising the cutaway portion of rail 11. Various test equipment could be positioned in this zone, and testing on passing wheels can be accomplished without disruption of normal railway traffic.

Because of the great weight carried by rail 106, it is preferably fabricated of air-hardened tool steel, heat treated to 54–58 Rc for maximum wear and strength characteristics, and chemically treated for minimum deterioration from corrosion. If the rail 106 is damaged or becomes worn during use, it can readily be replaced at the in-track installation in a matter of minutes.

Figure 2:
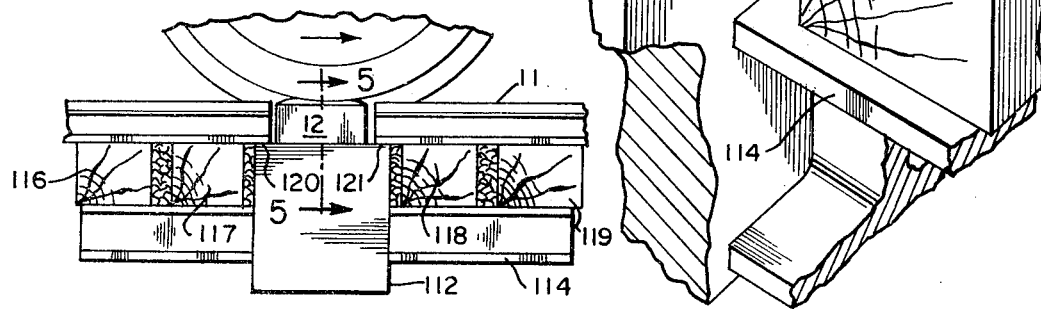
FIG. 2 is a side elevation view of the search unit of FIG. 1 and the associated supporting structure.

The base plate 100 is positioned on a concrete foundation 112 which replaces the usual railroad ties below the cutout portion of rail 11. Referring now to FIG. 2, the concrete foundation 112 is formed around a steel I-beam 114 which carries ties 116-119 supporting rail 11 adjacent to search unit 12, and the ends of rail 11 immediately adjacent to the search unit 12 rest on the concrete foundation 112 at 120 and 121. The concrete foundation 112 and the I-beam 114 therefore support each rail 11 and the thin rail plate 106 of search unit 12 together, providing a smooth running surface for wheel 40 as it approaches and travels over search unit 12.

A modified embodiment of the invention is shown in FIG. 30, 31, 31A and 31B where the upwardly protruding flexible boot 250A of a modified form of search unit 12A protrudes upwardly beside a support rail 106A into the path of advancing railroad wheel 39, all this shown in FIG. 31B. As shown in FIG. 31, a segment of standard track rail 11A is laterally offset to accommodate the support rail 106A and the field side of the upset portion rail 11A is ground away. A short field rail 11B provides a stiffening support for the assembly, and on the field side of the test unit 12A, and together with a guard rail 11C on the gauge side of the support rail 106A, the field rail is secured with the rail segments 11a to an underlying foundation plate 100B. An adaptor 100C overlying the foundation plate 100B is positioned directly below the baseplate 100A of the test unit.

A stiff, cylindrical strain gauge sensor 43B responsive to the approach of railroad wheels is mounted in the test unit assembly in force fitted interfering engagement with the web of the rail segment 11A as shown in FIG. 31 and 31A. The sensor 43B is preferably formed in the manner shown in FIGS. 32 and 33, with a stepped cylindrical sleeve configuration having a reduced entrance diameter 43C and successively larger central mounting diameter 43D several thousandths of an inch larger than a mating cylindrical hole 11D in rail segment 11A; a still larger stop shoulder 43E prevents the passage of the sensor unit 43B through aperture 11B and positions the central mounting diameter 43D substantially in alignment with the central plane with the web of rail 11A. A central transverse wall 43F extends transversely across the central portion of cylindrical sensor 43B providing a mounting surface for an electrical resistance strain gauge 43G whose resistance changes with physical deformation of the wall 43F. A threaded aperture 43A is formed in the reduced diameter entrance end of cylindrical sensor unit 43B providing threaded engagement for a drawbar employed to draw the cylindrical sensor unit 43B into force fitting interfering engagement with the aperture 11B in the web of rail 11A.

By positioning strain gauge 43G in the central plane of the web of rail 11A a few feet removed from the test unit 12A, the arrival of approaching wheel 39 above the sensor 43B as it travels along rail segment 11A produces a significant change in the resistance of strain gauge 43G signalling the close approach of the wheel to the test unit 12A and initiating the operation of the electronic circuitry hereandafter described to conduct the testing procedures upon the wheel as it passes over search unit 12A.

TRANSDUCERS AND MASK

Figure 4:
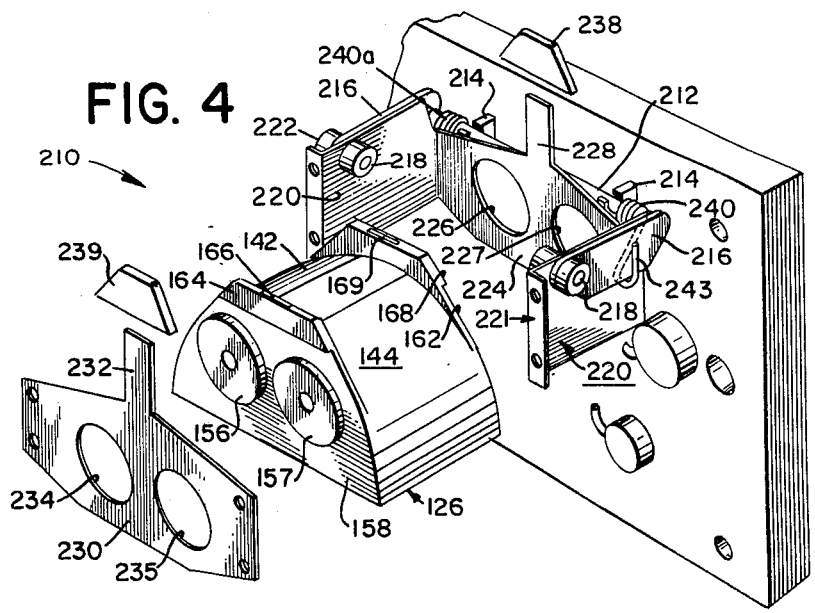
FIG. 4 is an exploded perspective view of a portion of the search unit of FIG. 1, including a spring-biased parallel-axis gimbaled suspension mounting means for a transducer-carrying mask.

The search unit 12 incorporates two rectangular transducers 122 and 124 which are mounted in a transducer mask 126, as best seen in FIGS. 4 and 8. The desired frequency for testing railroad wheels is in the range of 200 to 1000 KHz, and the preferred frequency is approximately 400KHz.

The transducers comprise rectangular lead zirconate piezo-electric crystals having a positive silver electrode plated on top surfaces 123 and 125 and a negative silver electrode plated on bottom surfaces 128 and 129. The active area of the electrodes is approximately 2 inches by 1/2 inch, and the transducers are pulsed with 20 amperes of current at 1500 volts to produce 400 KHz ultrasonic energy pulses.

The top positive silver electrode is electrically insulated by molding thereon a urethane coating 127. This coating is virtually transparent to ultrasonic energy waves in the frequency range of 200 to 1000 KHz, and therefore does not interfere with the transmitting and receiving capability of the transducer.

The directional radiating capability of the transducers 122 and 124 is enhanced by embedding their respective rear faces 128 and 129 in a tungsten-particle-filled elastomer backing 130. The backing 130 has a substantially semi-circular cross section, and extends the axial length of each transducer. It is heavy, and "damps" wave fronts emanating from the rear faces of the transducer, and also actually inhibits displacement of the rear faces. Consequently, upon pulsing the transducers the exposed front faces 123 and 125 achieve a greater displacement and thereby transmit stronger wave fronts. The receiving capabilities of transducers 122 and 124 are similarly enhanced by the casing 130.

A modified form of transducer crystal 122A shown in FIG. 29 employs a plated positive terminal electrode 128A on its front face and a negative or ground terminal electrode 129A plated on its rear face. The positive electrode 128A and its conducting lead 128B are encapsulated in a first insulating urethane coating 127A, on the outside surface of which is applied a layer 129B of metal-filled conductive lacquer joined electrically to ground electrode 129A and forming a radiation-shielding layer around crystal 122A and eliminating interference otherwise caused by arcing locomotive motors, nearby radio stations and magnetized railroad car wheels.

Tungsten-loaded backing 130A and outer urethane encapsulating layers 127B and 127C complete the transducer assembly shown in FIG. 29.

The transducer mask 126 matingly receives the two transducers 122 and 124 and their tungsten-filled elastomer casing 130 in two elongated transverse semi-circular sockets 138 and 139. The two transducers are axially aligned and their front surfaces 123 and 125 are tilted toward each other. The sonic axes 132 and 134, normal to the front faces of the transducers, are each disposed at an angle from vertical axis 136 in the range of 28° to 42° and preferably 35° as shown at 133 and 135 in FIG. 8.

The mask 126 functions to minimize unwanted interaction between the two transducers 122 and 124, and to direct pulses emanating therefrom toward wheel 40, shown directly over search unit 12. Also, the mask functions to direct ultrasonic energy pulses returned from wheel 40 to impinge on the transducer faces. Accordingly, the mask 126 comprises a central stem 140 positioned between the two sockets 138 and 139 wherein direct communication from radial mode "cross-talk" between the two transducers is minimized. The mask further comprises two wave-guide flanges 142 and 144 flanking the two transducers. Wave-guide flange 142 and the central stem 140 combine to provide a channel opening defined by planes 146 and 148 for directing ultrasonic energy pulses between transducer 122 and zone 149 on wheel 40 passing over the search unit. Similarly, wave-guide flange 144 and central stem 140 combine to form a second channel-opening defined by planes 151 and 153 extending between transducer 124 and a second zone 154 on wheel 40.

The mask is preferably fabricated of urethane filled with "micro-balloons". Micro-balloons are nitrogen filled spheres having phenolic outer casings with diameters in the range of 0.001 to 0.004 inches. The proportion of micro-balloons to urethane may be in the range of 1–5 to 18 by weight, and is preferably 1 to 6 by weight. The micro-balloon filled urethane exhibits very good attenuating characteristics for ultrasonic energy in the frequency range below 1000 KHz, and is also very light in weight.

Figure 5:
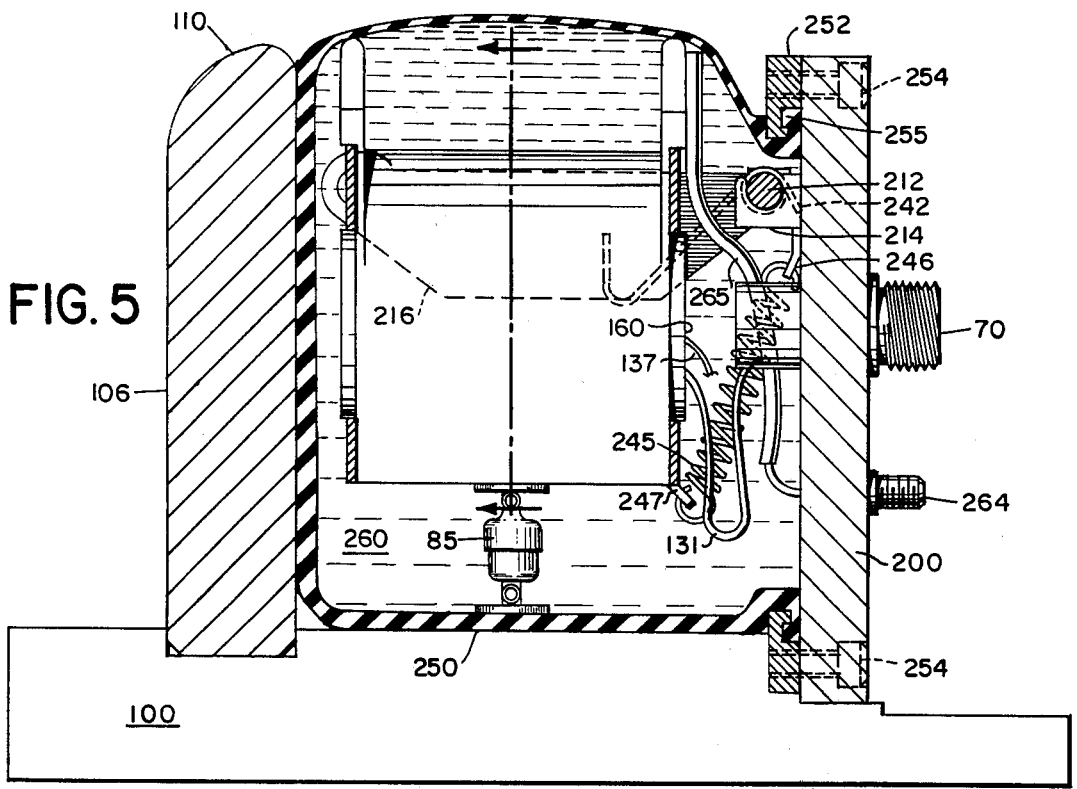
FIG. 5 is a vertical cross-sectional view of the search unit of FIG. 1, taken along the lines 5—5 of FIG. 2.

Referring now to FIGS. 4 and 5, the mask 126 has two circular bosses 156 and 157 raised from sidewall 158 and forming the ends of sockets 138 and 139. Two similar circular bosses 160 protrude from the opposing sidewall 162, and those bosses have a semi-circular central portion cut away to provide access to sockets 138 and 139 for slidingly mounting the transducers and their tungsten-filled urethane casing. The electrical leads 131 and 137 for transducers 122 and 124 also pass through the semi-circular openings, and are connected to co-axial fittings 70 and 71 on side plate 200.

Sidewall 158 extends upward from the body of mask 126 and terminates at its upper portion in a flange 164 having a vertical slot 166 formed therethrough. Sidewall 162 similarly terminates in an upper flange 168 also having a vertical slot 169 formed therethrough.

Parallel Axis-Gimbal Suspension

The search unit 12 further comprises a spring-biased, parallel-axis gimbal suspension means for positioning the two ultrasonic transducers 122 and 124 and mask 126 in proper orientation for transfer of ultrasonic energy pulses to and from the wheel being tested. Accordingly, the search unit 12 next comprises a side plate 200 which is removably secured to flanges 102 and 104 by means of bolts 202 and 204 (See FIG. 1). Referring now to FIGS. 4 and 5, a spring-biased parallel-axis gimbal suspension means 210 attached to the inside of side plate 200 carries the transducer mask 126 in which the transducers 122 and 124 are housed.

A modified embodiment of the invention incorporating a different form of resilient depressible transducer mask mounting is illustrated in FIGS. 21–28 and described in detail hereinafter.

The gimbal suspension means 210 consists of a first pivot shaft 212 carried in two C-shaped cradles 214 attached to the inside of side plate 200. At each end of pivot shaft 212 are secured arms 216 extending outward from near housing plate 200 to a second pivot axis comprised of two individual pivot shafts 218. The axis of shafts 218 is parallel to the axis of first pivot shaft 212.

The pivot shafts 218 pass through the end walls 220 of a rectangular metal housing 221 adapted to engage and carry the mask 126, and the shafts are secured thereto by flanking bushings 222. A first side wall 224 of the rectangular housing 221 joins the two end walls 220 adjacent to side plate 200 and pivot shaft 212. The side wall 224 has formed therein two round openings 226 and 227 which are adapted to engagingly receive the two circular bosses 160 on side 162 of mask 126. The sidewall 224 has an upwardly-protruding positioning arm 228 which extends through slot 169 in mask 126.

The mask 126 is mounted in the housing 221 by first inserting positioning arm 228 into slot 169, and subsequently attaching a second housing having sidewall 230 by inserting its corresponding positioning arm 232 through slot 166 in mask 126 and engaging the circular bosses 156 and 157 in the openings 234 and 235. The mask is secured in the gimbal suspension means by firmly attaching the second housing sidewall 230 to the endwalls 220 by means of screws.

The tips of positioning arms 228 and 232 are covered by caps 238 and 239. The tops of the caps are slightly arched, and the caps are fabricated of a smooth, long-wearing material such as urethane. The caps protect a urethane boot 250 from being punctured by the positioning arms.

The gimbal suspension means is biased upward to present the two positioning arms 228 and 232 to the running surface 38 of the wheel being tested. Referring to FIGS. 4–7, a coil spring 240 is coiled about pivot shaft 212. One end of the coil spring extends downwardly from the shaft 212 and seats against the side plate 200 at 242. The other end 243 of spring 240 extends outward from the pivot shaft 212 and is engaged under the arm 216. Thus the tension in coil spring 240 pivots arm 216 upward and lifts the positioning arm 232 upward against the running surface of a passing wheel. (See FIGS. 6 and 7). Another similar spring 240a may also be provided on pivot shaft 212.

A second coil spring 245 is secured to the side plate 200 at 246 and is attached to the bottom edge of the inside housing plate 224 at 247. The tension in spring 245 lifts the inside housing plate, thereby urging positioning arm 228 upward against the running surface of the passing wheel. When both positioning arms contact the running surface of the wheel, optimum alignment of the transducers and the running surface is achieved.

The parallel-axis gimbal suspension means 210 and the mask mounted therein are completely surrounded by a urethane boot 250, best seen in FIGS. 1, 5 and 8. The boot 250 is similar to a bag, having one open end which is positioned adjacent to the housing plate 200 and secured thereto by means of a retaining flange 252 which interlocks with a peripheral lip 255 of the boot. The peripheral flange 252 is secured to side plate 200 by means of recessed machine screws 254 passing through the side plate 200 into the flange 252, wherein the boot 250 may be easily changed if it becomes worn or damaged.

The boot is filled with a coupling fluid 260 which efficiently transmits ultrasonic waves. This fluid is preferably a 1:1 mixture of water and ethylene glycol, which resists freezing in cold temperatures. The boot is filled by means of a first check valve 262 (see FIG. 1) for introducing fluid through the side plate 200. A second check valve 264 is connected by tubing 165 to cap 238 on the top of positioning arm 228, whereby air may be vented from the top portions of the boot 250 as the boot is being filled.

The gimbal suspension means, the mask, and the transducers, all enclosed by boot 250, are mounted on side plate 200. Therefore, these parts can be quickly removed, and replaced as a unit, and testing can be continued with little "down time" in case of search unit failure.

Figure 6:
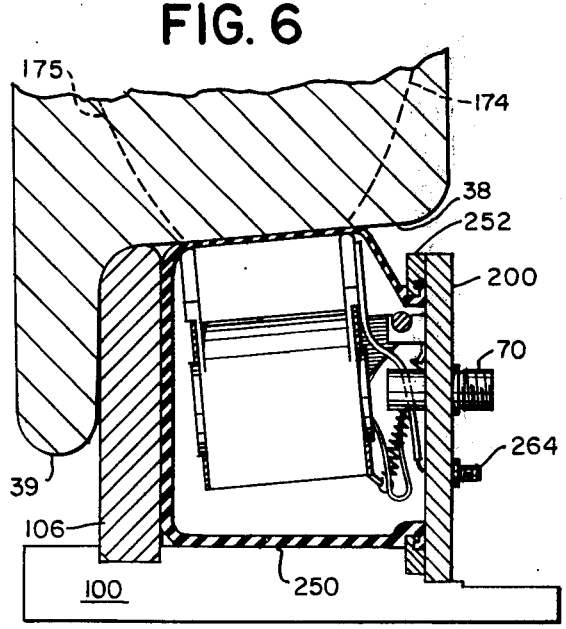
FIG. 6 is a similar vertical cross-sectional view of the search unit, showing the parallel axis gimbaled suspension conforming to a railroad wheel.

Referring now to FIG. 6, the railroad wheel 40 having an unworn running surface 8 is shown passing over the search unit 12. The wheel is supported adjacent to flange 39 on the top surface 110 of the thin rail 106, whereby most of the running surface 38 is available for coupling with boot 250 or other test equipment. The flange 39 is always closely positioned against thin rail 106 because the gauging devices such as 42 urge the flange against the inside or gauge edge of the track. The running surface of an unworn railroad wheel has a slight pitch with respect to the horizontal, the pitch being approximately one-twenty, the pitch being exaggerated in FIG. 6 for purposes of illustration.

The capped tips of positioning arms 228 and 232 are respectively urged upwardly against the running surface 38 by means of springs 240 and 245. Thus, the two positioning arms and the parallel-axis gimbal mounting means serve to hold the mask and associated transducers with the longitudinal axis of the transducers parallel to the wheel's running surface. This maximizes the exchange of ultrasonic energy pulses between the transducers and the wheels, and properly directs the waves in relation to the wheel, as will be more fully discussed below.

Also shown schematically in FIG. 6 is a shock absorber 85 mounted between bottom of boot 250 and the bottom of mask 126. The shock absorber is helpful during high speed testing when wheel-search unit contact may "bounce" the mask. The light weight micro-balloon filled urthane material produces a low-mass mask, which is also helpful in minimizing bounce.

Figure 7:
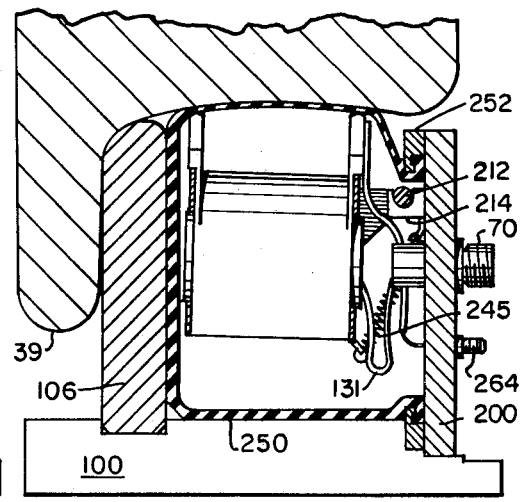
FIG. 7 is a similar vertical cross-sectional view of the search unit, showing the gimbaled suspension conforming to a worn railroad wheel.

Referring now to FIG. 7, a railroad wheel having a somewhat concave worn running surface is shown passing over the search unit. The worn running surface engages the capped tips of positioning arms 228 and 232 through boot 250, causing the transducer-mask assembly to pivot on its parallel-axis gimbal suspension means and to align the longitudinal axis of the transducers parallel to a central tangent to the worn running surface.

The fluid in the urethane boot 250 is displaced downwardly as the wheel rolls over the search unit, depressing boot 250. As the fluid is essentially incompressible, the boot is caused to closely conform to the running surface of the wheel, and, referring to FIG. 8, to cause the boot to wrap about a portion of the wheel's periphery encompassing zones 149 and 154.

The interface between the outside of boot 250 and the running surface 38 of the wheel is enhanced by means of wetting the top surface of the boot. This is accomplished by a coupling fluid spray system 44 which comprises a pressurized fluid reservoir connected to tubes 190 and 192 disposed transversely across the ends of search unit 12 (see FIG. 1). A portion of the connecting passage to tubes 190 and 192 is an internal bored passage 195 in side plate 200.

The transverse tubes 190 and 192 have a plurality of spray nozzles 193 aimed across the top surface of boot 250, and the coupling fluid spray is dispensed when the approach of the wheel is sensed by switches 43 or 54. The coupling fluid may be water, when warm temperature prevails, and an anti-freeze mixture in cold temperatures.

In the modified embodiment comprising a second preferred embodiment of the invention illustrated in FIGS. 21-28, the same first and second transducers are positioned in identical relationship to the passing wheel 39. In this modified embodiment, the support rail 106A abuts the field side of boot 250A which is shaped differently from the boot 250 shown in the previous drawings. In this embodiment, the boot 250A is a hollow shell having an open bottom 250B clamped by a clamping ring 250C similar to a hose-type clamping ring, securing the boot 250A in fluid tight relationship to a base 100A. In this embodiment the side plate 200A is U-shaped in plan and arms 200B extending alongside the ends of boot 250A as indicated in FIG. 22, and in combination with support rail 106A forming a substantially completely encircling enclosure for boot 250A, which thus protrudes upwardly a short distance from this enclosure into engagement with the passing wheel 39, as shown in FIG. 22.

Boot 250A is provided with outwardly protruding vertical ribs 250B on its front and rear sides and both ends, and these ribs are in abutting engagement with the support rail 106A and the U-shaped side plate 200A-200B substantially around the entire periphery of boot 250A. As a passing wheel 39 rolls over boot 250A resiliently depressing it downward, the boot is deformed and its angled end and front upper faces may be caused to bulge upwardly accommodating wheel 39. Ribs 250B provide a sliding contact of the sidewalls of the boot with the encircling enclosure, preserving the boot against damage to its fluid tight integrity from such abrasion.

As shown in FIG. 28, a series of fluid tight fittings 70A and 71A are provided for electrical transducer leads and for couplant fluid filling of boot 250A. A pair of heaters 70B are also provided for maintaining the couplant fluid within boot 250A within the desired temperature range, monitored by thermostat means connected through fluid tight fittings 70C all formed in base 100A which together with the side plate 200A-200B forms a bearing box assembly encircling and embracing the entire fluid filled boot except for its exposed wheel contacting upper face.

FLEXIBLE BOOT—SUSPENDED TRANSDUCER UNIT

The transducer supporting mask 126A shown in FIGS. 21-28 is generally similar in shape to the mask on 26 shown in FIGS. 4-8, but modified mask 126A is suspended directly from the flexible boot by internal depending flanges 250E best seen in FIGS. 25-27. The depending flanges 250E are provided with outwardly extending lower ledge portions securely engaging mask supporting plate 250F having reversely bent end edges engaging the outwardly extending ledges of flanges 250E. Plate 250F supportingly underlies the outer edges of the bottom of mask 126A and is provided with an enlarged central aperture. From an examination of FIG. 22, it will be evident that the approaching wheel rolling from left to right across the boot 250A will cause the boot to deform downwardly lowering first the left depending flange 250E and then the right depending flange, and thus causing mask 126A to pitch downward toward the approaching wheel, rock forward to the position shown in FIG. 22 and pitch forward following the wheel as it departs from the test unit 12A. Thus as wheel 39 rolls across the test unit, the sonic axes of transducers 122A and 124A automatically aimed toward the wheel and maintained in acoustically coupled relationship by the resilient deformation of boot 250A during the wheel's passage across the boot, thus maximizing the test time during which the system is conducting its ultrasonic testing operations upon the passing wheel.

This pitching motion of mask 126A in tracking alignment with the advancing wheel 39 is achieved by four upwardly extending alignment posts 126B having welded upper ends engaging the interior top of boot 250A as shown in FIGS. 22 and 28. In cooperation with the integral depending flanges 250E, these alignment posts or spaces 126B maintain the mask 126A in firm contact with the boot 250A and provide the automatic resilient tracking movement of the transducers utilizing the boot's own deflection, without the need for the more complex mechanisms illustrated in FIGS. 4-7. A venting passageway 126C formed in one of the alignment posts 126B is connected with a venting tubing 265A, as shown in FIG. 28, allowing entrapped air to be vented from the interior top of boot 250A and pemitting the boot to be substantially completely filled with couplant fluid.

ULTRASONIC ENERGY PULSE: SHAPE, REFRACTION, AND MIGRATION

Referring now to FIG. 8 wherein wheel 40 is positioned above the mask 126 and transducer 122 and 124 as described above, pulsing transducer 124 causes an ultrasonic energy pulse to be delivered to wheel 40. The ultrasonic energy pulse on entering wheel 40 is bent or deflected toward the left along the periphery of wheel running surface 38, travelling through a region whose boundary, in effect, is believed to have a shape substantially as outlined by dotted line 170 and the wheel running surface 38. The precise composition of the ultrasonic energy pulse in the wheel is unknown, but it is believed to have a deep surface wave component travelling through the region outlined by dotted line 172 and running surface 38, the remaining portion of the wave between dotted lines 170 and 172 comprising shear waves refracted to travel generally about the periphery of the wheel.

Through localized probe monitoring it has been found that the high energy, low frequency 400 KHz energy pulse attains very great penetration in the wheel 40, the initial depth of penetration D being 8 or more inches. Also, the pulse is dispersed throughout the width of the wheel, as indicated by dotted lines 174 and 175 in FIG. 6. The depth of penetration and dispersion are very useful in testing wheels and particularly railroad wheels, and would not be obtained by using ultrasonic energy pulses having frequencies well above 1,000 KHz as taught in the prior art. Such pulses would comprise a very shallow surface wave component if introduced into the wheel in the manner described herein.

The ultrasonic energy pulse is caused to travel about the periphery of the wheel because of refraction. The refractive index of the fluid trapped within the boot and interposed between the transducers and the wheel is approximately 1.50 and the refractive index of a steel railroad wheel is approximately 2.74. The urethane boot 250 is virtually transparent to 400 KHz pulses, and is not a factor. Therefore, the wave front of the ultrasonic energy pulse presented to the railroad wheel at an angle of approximately 35° from the vertical is generally refracted approximately tangent to the surface of the railroad wheel according to Snell's Law, which states:

$$\sin \theta = V_o/V_s$$

wherein $V_s$ is the surface wave velocity in steel and $V_o$ is the longitudinal wave velocity in the ethylene glycol-water mixture. Therefore, at least a portion of the ultrasonic energy pulse introduced into the railroad wheel is refracted to form a surface or Rayleigh wave front.

At the preferred frequencies the angle of incidence to the railroad wheel is not sharply critical, and pulses introduced at angles of 20° to 42° from the vertical will be refracted to have a surface wave component. The angle of 35° is preferred to give a strong surface wave component.

Although ultrasonic energy pulses normally display a tendency to travel in a straight line, the ultrasonic energy pulse in the wheel cannot escape at the steel running surface-air interface, and is therefore apparently "bent" to travel around the periphery of the wheel. However, the tendency of the ultrasonic energy pulse to travel in a straight line is believed to cause the portion of the ultrasonic energy pulse which has initially penetrated into the wheel to a substantial depth to gradually approach, or "migrate" toward the curved running surface, thereby increasing the strength of the surface wave immediately adjacent thereto.

The migration of the surface wave toward running surface 38 is illustrated in FIG. 8. Dotted line 178 indicates the depth of the wave after its first trip around the wheel, dotted line 179 indicates the depth after a second round trip, and dotted line 180 indicates the depth after a third round trip.

The migration phenomenon is very important for testing curved surfaces for surface defects because the gradual "concentration" or increase in the strength of the surface wave immediately adjacent to the surface from migration more than compensates for the attenuation of the surface wave by virtue of length of travel. Therefore, useful information can be obtained for as many as 5 to 10 round trips of the ultrasonic energy pulse in the wheel, whereas, considering only attenuation, useful information would only be expected for one to two round trips.

The migration phenomenon is also important for testing railroad wheels in that a portion of the ultrasonic energy pulse migrates outward to travel about the periphery of the flange of the railroad wheel, providing an opportunity for a wear measurement as will be described below.

On each round trip, a portion of the ultrasonic energy pulse is refracted out of the wheel at zone 149 to impinge on transducer 122. Because of the wide dispersion of the ultrasonic energy pulse, a portion of the pulse travelling about the flange 39 also impinges on transducer 122 on each round trip.

METHOD OF TESTING

Referring now to FIG. 3, as wheel 40 approaches search unit 12, it operates a switch signaling to the electronic test circuit both in the presence of a wheel and its direction of approach. Thereafter, the pulse control portion of the electronic test circuit repetitiously pulses the search unit transducer facing the direction of wheel approach, so that a pulse is introduced to the wheel shortly after the wheel's initial contact with the search unit. Referring now to FIG. 8, transducer 124 is regularly pulsed as wheel 40 approaches the search unit 12 from the left. The wheel first reaches the zone 154, and an ultrasonic energy pulse from transducer 124 contacts the wheel at that zone, and enters the wheel as described above.

The initial transducer pulse rate is dependent upon the types of wheels to be tested, and is particularly dependent upon the density or refractive index and the circumference thereof. For purposes of testing the wheel, it is desirable to have only one pulse in the wheel at any given time. Referring still to FIG. 8, confirmation that a pulse has entered the wheel at zone 154 occurs when the pulse has traveled completely about the periphery of the wheel returning to the wheel-boot interface, wherein a portion of the wave is refracted out of the wheel at zone 149 and impinges upon transducer 122. To assure that transducer 124 does not introduce a second pulse into the wheel, the pulsing rate of transducer 124 is set sufficiently low so that the time interval between pulses is greater than that necessary for a pulse to travel completely around the wheel. The first pulse entering the wheel at 154, traveling clockwise there around and exiting at 149, to impinge on transducer 122 produces a electrical signal which is used to inhibit further pulsing of transducer 124.

Referring now to FIG. 9, there is schematically shown wheel 40 positioned over search unit 12 having a transducer A corresponding to transducer 122 in FIG. 8 and transducer B corresponding to transducer 124 in FIG. 8. The wheel-boot interface encompassing zones 149 and 154 is designated at E. FIG. 10 is a timing diagram showing operation of transducers A and B during the test wheel 40.

Because wheel 40 is traveling from left to right, transducer B is repetitiously pulsed as indicated at 310, 311, and 312 in FIG. 10. Pulse 312 is refracted into wheel 40 and travels about the periphery thereof returning to interface E wherein a portion of the wave is refracted out of the wheel and received by transducer A as pulse 314. Referring to the scale markings, through-transmission pulse 314 is received at A prior to the next, repetitious pulsing of transducer B indicated in dotted lines at 316, which pulse is inhibited by the pulse control upon receiving the first through-transmission 314.

Through-transmission pulse 314 comprises only a portion of the pulse passing clockwise about wheel 40. On the pulse's next passage through interface zone E, an additional portion is refracted toward transducer A and received there as pulse 318. Subsequent revolutions produce pulses 320–323 at transducer A. The pulse is gradually attenuated in wheel 40, and this attenuation is apparent in the pulses received at transducer A. As noted above the attenuation is partially offset by the migration phenomenon.

The wheel 40 shown in FIG. 9 has a defect located at C. A portion of the initial clockwise traveling pulse 312 introduced into the wheel from the transducer B is reflected from the defect C back along the path C-E, wherein a portion of the reflected pulse is returned to transducer B, as indicated at 325 in FIG. 10. As pulse 312 continues to pass clockwise around wheel 40, a further portion thereof is reflected back from defect C each time the pulse is presented thereto. The subsequent defect echoes received by transducer B are indicated at 326–330.

Despite the attenuation of the initial pulse 312 as indicated by the steady decrease of the strength of the through-transmission 314 through 323, the size of the reflected return pulses from defect C increases and reaches its largest magnitude in the second and third reflection. Then, pulses 326 and 327 of FIG. 10 are the largest defect echo pulses, and pulses 329 and 330 represent a decrease in reflected pulse. This phenomenon has two possible explanations. First, it is believed that as the pulse travels about the periphery of the wheel, the strength of the pulse becomes increasingly concentrated very near the surface thereof. This is because the pulse is continually being bent in a circular path, wherein the pulse would travel in a straight line if free to do so. The greater magnitude of echo pulses 326 and 327 may then be explained because the defect C is normally of a very shallow depth, wherein a great portion of the earlier deeper pulses passing the defect would merely pass thereover. This increased strength of the echo pulses thereby provides confirmation of the migration effect described above. The position of the defect C causes the best display of this phenomenon because of the relatively short "in-steel" paths between the defect and the transducer, wherein attenuation is a lesser factor.

A second possible explanation for the increased size of the third and fourth echo pulses 327 and 328 is that the first echo pulse 325 continues to rotate counterclockwise about the wheel 40. On its second passage along the arc C-E, the echo pulse would reinforce subsequent reflections of the initial clockwise traveling pulse from defect C. This second theory is believed to be less likely.

Complete testing of the wheel comprises initiating a second initial pulse in a counterclockwise direction. The second counterclockwise rotating pulse would not be useful for test purposes until the first clockwise rotating pulse has dissipated so that no confusion between the remnants of that pulse and defect echoes can occur. Balanced against the need to wait for the first pulse to subside is the need to initiate the second pulse before the wheel passes completely over the search unit. It has been found that the initial pulse is sufficiently diminished in intensity after approximately 5 milliseconds, or time for 5 or 6 revolutions of travel about the wheel. Therefore, a second conterclockwise traveling initial pulse is introduced by means of transducer A as indicated at 332. It is convenient to synchronize pulsing of transducer A with the through-transmission pulses, wherein pulse 332 is coincident with the last through transmission of the clockwise testing period. Confusion between the remnants of the first pulse and the second pulse 332 is thereby avoided in that both pulses pass through interface E at the same time.

Defect C is positioned approximately 270° of rotation away from transducer A in a counterclockwise direction. Therefore, the first echo pulse is not received until after the first through-transmission, the first echo pulse being indicated at 334 and the first through transmission received by transducer B being indicated at 340. The echo pulses 334 through 339 have an approximately equal magnitude through 336, as compared to the normal, expected attenuation exhibited by the through-transmission pulses 340–345. This is again caused by the migration of the counterclockwise traveling pulse to the running surface wherein a greater portion is reflected. Upon the last through transmission in the test period, transducer B is again pulsed at 346, wherein the first portion of the test is repeated. A wheel moving slowly over the search unit may be tested as many as ten times. The subsequent tests are not merely redundant, as a first test may be inaccurate because of dirt, or the like trapped on the wheel and interfering with the boot wheel interface.

Referring now to FIGS. 11 and 12, there is schematically shown wheel 40 having a defect at the position D being tested as it passes over search unit 12 from the left. Referring to line B of FIG. 12, transducer B facing the direction of approach of the wheel is regularly pulsed at 350 and 351. Transducer A receives a first through-transmission pulse at 360 indicating that pulse 351 was properly refracted into the wheel. The pulse 360 inhibits further pulsing of transducer B, wherein the next pulse would have occurred at 352 indicated in dotted lines. Following the through-transmission pulse 360 are the subsequent through-transmission pulses received at transducer A for each revolution of the pulse in the wheel, the pulses 361–365 indicating useful test duration of pulse 351.

The defect D is shown approximately 225° clockwise from the interface entry and exit zone E. Thus the first echo from the defect returned to transducer B travels a radial distance E–D and D–E of 450°, producing return echo pulse 353. Subsequent echo pulses 354–357 occur regularly thereafter. These pulses also display the phenomena of increasing instead of attenuating during the initial portion of the test period, as described above.

The first through-transmission 360 initiates a testing period, wherein the pulsing mechanism for transducer A is caused to run simultaneously with the through-transmission pulses, finally pulsing transducer A as indicated at 358 coincident with the final, useful through-transmission pulse 365. Thereafter through-transmission pulses 370–374 are received at transducer B and transducer B is again pulsed at 375. The defect D reflects a portion of ultrasonic energy pulse 358, creating echo pulses 376–381. The echo pulses grow in magnitude, reaching their largest size at the second and third pulses 377 and 378.

Testing of wheels moving at high speeds is shown schematically in FIGS. 13 and 14, wherein the wheel 40 is shown approaching search units 12 and 13 from the left. The additional problem to be overcome in high speed testing comprises the short time interval that the wheel contacts the first search unit 12 which time is insufficient for both clockwise and counterclockwise testing to be accomplished It is desirable to test in both directions because a defect may be shaped such that it reflects well in only one direction.

As the wheel approaches from the left, transducer B, is repetitiously pulsed as indicated at 390 and 391, the latter being the first pulse to be introduced into the wheel when the wheel reaches PO1, resulting in a through-transmission pulse 392 at transducer A. A defect F located relatively near the interface zone E produces a first echo pulse 400, and subsequent echo pulses 401–405.

The subsequent through-transmission pulses 393–397 are generated as pulse 391 travels about the wheel. However, through transmission pulses 395–397 are not received at transducer A, because the wheel 40 has traveled to a position PO2 wherein an interface between wheel 40 and transducer A no longer exists. Therefore pulses 395–397 are shown dotted. Similarly, echo pulses 404 and 405 are not received by transducer B, and are shown dotted. The interface between transducer B and wheel 40 is lost slightly prior to the interface between transducer A and the wheel, because of the relative positions of zones 149 and 154.

Following through-transmission pulses 397 transducer A is pulsed at the normal sync rate as indicated at 410–412. Because the wheel is somewhere between seach units 12 and 13, the pulse 410 is not received as a through-transmission at transducer B. Transducer A is therefore continually pulsed as indicated at 411, 412 and 413, pulse 413 being delivered to the wheel when it arrived at postion PO3. Pulse 413 creates a through-transmission pulse for 414 received at transducer B, which pulse inhibits further pulsing of transducer A. Subsequent through-transmission pulses 415 and 416 are received at transducer B, and echo pulses 417 and 418 indicating the presence of defect F are received at transducer A. When the wheel has reached position 3, the relative position of defect F to the wheel-boot interface is altered by the rotation of the wheel, and consequently the position of defect echo pulses 417 and 418 is different than the first group of defect echo pulses 400–405.

In the system described herein, wheels moving at velocities of up to 60 miles an hour are effectively tested by passing over two closely spaced search units.

The migration of surface waves to the outermost part of the wheel is important in the method of wear testing used herein. A portion of the ultrasonic energy pulse introduced into the running surface migrates outward and travels about the larger diameter periphery of the flange, as shown schematically in FIG. 15 at 438. For the sake of clarity, the wheel 40 in FIG. 15 is shown free from defects, and approaching from the left. Pulse 425 introduced by transducer B creates through transmission pulses 426–431. Although the first group of through transmision pulses contain the necessary information for wear testing it is preferable to use them to establish the period of rotation, and to conduct the wear test during the second, clockwise phase of testing. The second phase of testing is initiated with pulse 432 deliverd into the wheel from transducer A coincident with the last through-transmission pulse 431. Pulse 432 is shown entering the running surface 39 of wheel 40 at 435, whereafter a portion 436 of the pulse travels about the running surface 38 of the wheel and is received as a first lobe 437 of through transmission pulse 445 impinging on transducer B. A second portion of the pulse 432 is shown at 438 migrating toward the flange 39 of the wheel, and running about the periphery thereof as indicated at 439. Because of the greater diameter of the flange 39, the path of the migrating portion of the pulse 438 and 439 is longer than the path of 436, and causes a second lobe 440 through transmission pulse 445 to be received at transducer B a short time interval $\Delta t$ after the lobe 437. As the running surface 38 of the wheel becomes worn, the path 436 about the periphery of the running surface becomes shorter, and a greater difference in travel time about the flange as compared to the running surface exists, causing a $\Delta t$ to become larger. A wear defect alarm is signaled when $\Delta t$ exceeds an established acceptable maximum interval.

The $\Delta t$ is not dependent on the size of the wheel under test, but only upon the difference in diameter between the running surface and the outer flange thus the same maximum acceptable $\Delta t$ may be used to signal a wear defect without the determination of the size of wheel under test.

However, it is desirable to know the size of wheel being tested so that replacement wheels may be ordered and stock piled at repair facilities. The electronic test circuit therefore measures the travel time of a pulse about the periphery of the wheel, and translates that travel time into an indication of wheel size.

ELECTRONIC TEST CIRCUIT

The circuit diagram of the electronic test circuit 20 is shown in FIG. 17. The electronic test circuit comprises generally an approach direction control sensor 21, a pulse control portion 22, an automatic gain control portion 23, a test certification portion 24, a defect test and alarm portion 26, a wear test and alarm portion 28 and a wheel size measurement portion 29. Also shown in FIG. 17 are a power supply 32, a main sync generator 34, and video display 36 comprising support circuitry 30 for the electronic test circuit 20. This circuitry 30 also comprises a "Reflectoscope," and is commercially available from Automation Industries, Inc., Model No. UM 771. Other companies make similar equipment.

DIRECTION CONTROL

There is also shown schematically in FIG. 17 the rail 11 having search units 12 and 13 positioned therein for high speed testing. Each search unit has two transducers mounted therein as described above, search unit 12 having a left transducer 122 and a right transducer 124, and search unit 13 having a left transducer 122a and a right transducer 124a. The search units 12 and 13 are respectively provided with coupling fluid spray dispensers 44 and 46, and wheel sensing switches 43 and 54 are shown deployed flanking the two search units. For purposes of illustration, it is assumed that normally-closed switch 54 was last energized, which set flip-flop 500, and flip-flop 502 was reset through a ten-microsecond delay network 501.

Wheel 40 approaching the wheel-testing apparatus from the left first rolls over and opens normally closed switch 43, thereby setting flip-flop 502 and initiating a second ten-microsecond delay network 503. Thus, flip-flops 500 and 502 are both set for an interval of 10 microseconds, i.e. until delay network 503 causes flip-flop 500 to be reset. The output of AND gate 504 is thereby positive for ten microseconds, and initiates an eighty millisecond delay network 505, the output signal of which goes through a power amplifier 506 and energizes solenoids 507 and 508, causing coupling fluid to be sprayed on to the boots of search units 12 and 13 by the coupling fluid spray dispenser units 44 and 46. The coupling fluid is applied prior to the arrival of wheel 40 at the search units 12 and 13.

During the ten-microsecond interval when both flip-flops 500 and 502 are positive, inverters 510 and 511 inhibit AND gates 512 and 513 from passing any signal. Upon expiration of the ten-microsecond interval, delay 503 causes flip-flop 500 to be reset to its normal zero condition, wherein by means of inverter 510 both inputs to AND gate 512 are positive. The resultant output of AND gate 512 is called the "RIGHT CONTROL", the "right" referring to the right-hand transducers 124 and 124a in the search units 12 and 13, which transducers will be first pulsed in testing wheel 40 as described above.

If wheel 40 approaches the search units from the right side, flip-flops 500 and 502 similarly cooperate with the other previously described circuit elements to provide a coupling fluid spray release and to raise a "LEFT CONTROL" signal wherein left transducers 122 and 122a are first pulsed. It can also be seen that after wheel 40 has passed over search units 12 and 13 it operates switch 54, setting flip-flop 500 which conditions the elements for the approach of a subsequent wheel.

PULSE CONTROL

The pulse control portion of the electronic test circuit is shown at 22 of FIG. 17. The positive signal on the right control line is presented to one input of AND gate 520, the other input of which is connected to the main sync generator 34 which is set at a pulse rate of 1.1 milliseconds. AND gate 520 therefore passes the main sync pulses to AND gates 521 and 522. AND gate 521 is enabled by a "SYNC INHIBIT No. 1" signal held positive through AND gate 523, as will be described hereinafter. AND gate 522 is not enabled at this time.

The main sync pulses passing through AND gate 521 pass through OR gate 528 and buffer amplifier 530 to reset flip-flops 531 and 532. The main sync pulses passing through OR gate 528 also comprise the "TRANSIGATE SYNC" signal and are accordingly delivered to TRANSIGATE 533, which is commercially available as Model 50E550 from Automation Industries, Inc.

The main sync pulse comprising the output of AND gate 521 initiates a twenty-five microsecond delay network 524, and the output thereof passes through an inverter 525 into right pulser-receiver 526. The right pulser-receiver pulses the two right side transducers 124 and 124a at 1.1 microsecond intervals, which trail the main sync pulses by 25 microseconds as shown on the timing diagram of FIG. 18 at 699. The right pulser-receiver 526 and its companion left pulser-receiver 527 are commercially available as Model 10W50D53 from Automation Industries, Inc.

The 25-microsecond delayed main sync pulses passing through delay 524 further pass through OR gate 534, are delayed 20 microseconds by delay 535, and set flip-flop 532 through AND gate 536 which is enabled by the SYNC INHIBIT No. 1. Noting that delay 535 has a normally high output, flip-flop 532 is set on the next positive transition. Therefore, flip-flop 532 is reset at the leading edge of the main sync pulse, and is set 45 microseconds thereafter by means of the two delay networks 524 and 535.

If the wheel 40 approaches the search units 12 and 13 from the right or opposite direction, the LEFT CONTROL signal will go positive, as described above. The LEFT CONTROL signal enables AND gate 540, and thereby passes the main sync pulses to AND gates 541 and 542, the former of which is held off by a low "SYNC INHIBIT No. 2" signal, as is AND gate 522. AND gate 542 is enabled by the "SYNC INHIBIT No. 1" signal, and passes the main sync pulses through OR gate 528 and buffer amplifier 530 to reset flip-flops 531 and 532. A transigate sync signal is also provided.

The main sync pulses from AND gate 542 also pass through a twenty-five microsecond delay 543 and an inverter 544 to the left pulser-receiver 527, wherein the left transducers 122 and 122a are pulsed at main sync rate with a twenty-five microsecond time delay. The output of the delay 543 also passes through OR gate 534, the twenty microsecond delay network 535, and AND gate 536 to set flip-flop 532. AND gate 536 is enabled by the SYNC INHIBIT No. 1 signal, which is positive. Therefore, flip-flop 532 is reset at the leading edge of the main sync pulse, and is set 45 microseconds thereafter by means of the two delay networks 543 and 535, as it was for a wheel approaching from the left.

The preceding describes the operation of the pulse control portion 22 of electronic test circuit 20 for pulsing appropriately the right or left transducers, depending on the direction of travel of a wheel approaching the search unit assemblies. It will be noted that the pulse control portion of the electronic test circuit continues to pulse the selected transducers at the main sync rate until the wheel contacts the search unit apparatus comprising search units 12 and 13, and on each pulse flip-flop 531 is reset, and thereafter set approximately 45 microseconds after the initiation of the main sync pulse.

Again assuming that the right control line is active wherein the right side transducer 124 and 124a are pulsed, there is a RIGHT VIDEO output from right pulser-receiver 526. The RIGHT VIDEO output passes through AND gate 546 which is enabled by means of the RIGHT CONTROL signal. The output of AND gate 546 is labeled VIDEO No. 1. When the LEFT CONTROL signal is high causing the left pulser-receiver 527 to pulse the left side transducers 122 and 122a, a LEFT VIDEO output is produced which passes through AND gate 547 enabled by the LEFT CONTROL signal. The output of AND gate 547 is in parallel with the output of AND gate 546, and is also labeled VIDEO No. 1. Therefore, regardless of whether the left or right side is first pulsed, a synchronous VIDEO No. 1 signal results, as shown at 700 on the timing diagram of FIG. 18.

Assuming the right pulser-receiver is pulsing transducers 124 and 124a and the wheel 40 contacts the first search unit 12, an ultrasonic energy pulse enters the wheel, travels peripherally therabout in a clockwise direction, and is received by the left side transducer 124 which transmits a pulse to the left pulser-receiver 527. This "through transmission" pulse appears as a LEFT VIDEO signal which passes through AND gate 548 enabled by the positive condition of the RIGHT CONTROL. The resultant output of AND gate 548 is designated VIDEO No. 2.

When the left pulser-receiver 527 is initially pulsing transducers 122 and 122a for a wheel approaching from the right, the first through-transmission appears as a "RIGHT VIDEO" signal from right pulser-receiver 526. The RIGHT VIDEO signal passes through AND gate 549 which is enabled by the positive condition of the LEFT CONTROL line, wherein the signal also becomes VIDEO No. 2. Therefore, regardless of whether the left or right pulser-receiver is initially being pulsed, the first through-transmission appears as VIDEO No. 2.

The VIDEO No. 2 signal is presented to an AND gate 550. The second input to AND gate 550 is the "TEST TIME No. 1" signal, which is the output of flip-flop 532. As described above, setting of flip-flop 532 is delayed by delay 535 for 20 microseconds subsequent to pulsing either left pulser-receiver 527 or right from passing through AND gate 550 because of the negative output of flip-flop 532, and lack of a TEST TIME No. 1 signal.

A through-transmission pulse appearing as a VIDEO No. 2 signal occurs approximately 0.96 milliseconds after the sending transducer was pulsed, for a 33 inches diameter railroad wheel, at which time flip-flop 532 has been set positive to enable the VIDEO No. 2 signal to pass through AND gate 550. The main sync rate (See 698 of FIG. 18) is preferably set at 1.1 milliseconds, a time greater than that for a pulse to travel around the largest railroad wheel to be tested; a through-transmission therefore always occurring prior to the next main sync pulse. The main sync rate would be set lower if testing of larger wheels was being performed.

The first through-transmission pulse appearing as a VIDEO No. 2 signal passes through AND gate 550 and bias amplifer 551, which provides a pulse output provided a sufficient input level exists. The input level in this application is set very close above noise, and a large signal such as the first through-transmission signal therefore passes through the bias amplifer 551 to become a "TX GATED DECISIONS No. 2" signal which initiates a four millisecond delay 552. The output of delay 552, labeled "TX TIME No. 1" and shown at 730 of FIG. 18B, is applied through inverter 553 to one input of AND gate 554, the output of which comprises one input to AND gate 523. AND gates 523 and 554 were initially positive wherein the SYNC INHIBIT No. 1 signal was high permitting passage of the main sync pulse through either AND gate 521 or AND gate 542. However, the delay 552 and inverter 553 cause AND gate 554 and consequently AND gate 523 to be inhibited whereby SYNC INHIBIT No. 1 goes to zero preventing further pulsing of the pulser-receiver. (See Timing diagram, FIG. 18, at 704). During this period, the ultrasonic energy pulse introduced into the wheel 40 continues to travel about the periphery thereof, as described above, and provides through-transmission pulses shown at 715 of FIG. 18A.

The "TX GATED DECISIONS No. 2" output signal of bias amplifier 551 also passes through OR gate 555, and is thereafter labeled "MAIN SYNC RESET." This signal forces the main sync generator 34 to run synchronous with the throughtransmission pulses comprising TX GATED DECISIONS No. 2. However, because AND gate 521 is inhibited, the reset main sync signal does not cause further pulsing of right pulser-receiver 526.

Following the four millisecond delay caused by delay 552, inverter 553 goes positive initiating another delay 556 one and one-half milliseconds in duration. The output of delay 556 is normally high, and the signal from inverter 553 thereby causes a one and one-half millisecond negative output from delay 556 which is applied to the center input of AND gate 554. Therefore, after the four millisecond delay inhibiting AND gate 554, AND gate 554 is inhibited for an additional one and one-half milliseconds.

The negative going output of delay 556 is also inverted by inverter 557 and goes through OR gate 558 wherein a positive "SYNC INHIBIT No. 2" signal is established (See 706, FIG. 18). The positive SYNC INHIBIT No. 2 signal sets flip-flop 560 wherein its normally high output inhibits AND gate 523. The positive SYNC INHIBIT No. 2 signal is also applied to one input of AND gate 541, one input of AND gate 522, and one input of AND gate 545. Therefore, the reset main sync pulse coming through AND gate 520 is permitted to pass through AND gate 522, is delayed 25 microseconds by delay 543, and thereafter passes through inverter 544 to left pulser-receiver 527 (See FIG. 18 at 708). The sync pulse also passes through OR gate 528 and buffer amplifier 530 to reset flip-flop 531 and provide a new TRANSIGATE sync. The output of delay 543 passes through OR gate 534, twenty microsecond delay 535, and AND gate 545 enabled by the positive SYNC INHIBIT No. 2 signal to set flip-flop 531 approximately 45 microseconds later.

The output of flip-flop 531 is a TEST TIME No. 2 signal which is applied to one input of AND gate 561. Another positive input of AND gate 561 is provided by the output of flip-flop 560 through OR gate 562. The first pulse of the left transducer 122 by left pulse receiver 527 is immediately received through the search unit 12 by the right transducer 124 and is given off as a right video output from right pulser-receiver 526. The right video output is applied to the input of AND gate 546, the other input of which is enabled by the right control line. Thus a positive VIDEO No. 1 signal is produced upon the pulsing of the left pulser receiver 527, and the positive VIDEO No. 1 signal comprises the third input to AND gate 561. However, AND gate 561 is not enabled at this time because of the 45 microsecond delay in setting flip-flop 531, during which time TEST TIME No. 2 signal remains negative.

The pulsing of left pulser-receiver 527 being the second portion of testing wherein pulses are produced for counterclockwise rotation about wheel 40. The one and one-half millisecond delay 556 permitted sufficient time to insure that the main sync generator fired the left pulser-receiver 527 at least once, and expiration thereof causes SYNC INHIBIT No. 2 to go to zero, as indicated at 706 of FIG. 18. To prevent right pulser-receiver 526 from being pulsed during the second test time, the output of delay 556 initiates a four millisecond delay 563, the output of which is inverted by inverter 564 and applied to one input of AND gate 554, thereby inhibiting AND gate 523 and keeping the SYNC INHIBIT No. 1 line negative. The output of delay 563 also passes through OR gate 562 providing an alternative high input to AND gate 561.

The first through transmission received by the right pulser receiver 526 becomes a positive VIDEO No. 1 signal as described above, and is passed through AND gate 561, now enabled by TEST TIME No. 2, and bias amplifier 565, the output of bias amplifier 565 comprising TX GATED DECISIONS No. 1. The TX GATED DECISION No. 1 signal is passed through OR gate 555 to reset the main sync generator synchronous therewith, and is passed through OR gate 566 to reset flip-flop 560. If the delay 563 has expired, for instance when the wheel 40 is between search units 12 and 13, then the first through transmission pulse resets flip-flop 560 re-initiating the four millisecond delay 563, permitting a full test time interval and maintaining the negative input on AND gate 554 wherein the right pulser receiver 526 is prevented from pulsing.

It is also convenient to note at this time that flip-flop 560 is reset through OR gate 556 when either the right or left control signal goes positive, contributing to the initial positive condition of SYNC INHIBIT No. 1 through AND gate 523, as described above.

If the wheel 40 is moving in excess of 30 miles an hour, it will cross over search unit 12 during the first test time. Therefore, when the second test time is initiated and the left pulser-receiver 527 is pulsed, no signal is delivered to the wheel and no through-transmission exists. Without a through-transmission, a positive TX GATED DECISIONS No. 1 does not occur to reset flip-flop 560. Therefore, AND gate 522 is not inhibited, and the left pulser receiver 527 continues to pulse at the sync rate. When the wheel 40 passes over search unit 13, the left transducer 122a therein delivers a pulse into the wheel, and a through-transmission is received by the right transducer 122a therein. This resets flip-flop 560, terminating SYNC INHIBIT No. 2 as indicated at 710 of FIG. 18. Thus the second test time is accomplished over the second search unit 13, which is therefore necessary for high speed testing.

After expiration of TEST TIME No. 2, wherein the wheel was tested by loading an ultrasonic energy pulse therein for opposite travel around the periphery, the electronic test unit switches over and retests the wheel in the first direction. Assuming that the right control signal is high and the right pulser-receiver 526 was first pulsed and the left pulser-receiver 527 was second pulsed, the subsequent through-transmission at right pulser-receiver 527 causes a VIDEO No. 1 signal resetting flip-flop 560, re-initiating the four millisecond delay 563 comprising TEST TIME No. 2 if necessary. At the expiration of the four millisecond delay 563, a positive signal is provided on one input of AND gate 554. The other two inputs to AND gate 554 comprise the inverted output of delay 552 and the output of normally high delay 556 or the $\overline{Q}$ output of flip-flop 560. Resetting flip-flop 560 in TEST TIME No. 2 also caused one input of AND gate 523 to be positive, the $\overline{Q}$ output of flip-flop 560 also providing a positive signal to AND gate 523, as well as to the central input of AND gate 554, thereby enabling AND gate 523 and creating a positive SYNC INHIBIT No. 1 condition (See FIG. 18 at 712). The positive SYNC INHIBIT No. 1 permits the main sync pulses to pass through AND gate 521, pulse right pulser receiver 526, and establish a second TEST TIME No. 1.

The electronic test circuit continues to test the wheel by alternatively testing in first one direction and then the other direction so long as through-transmission pulses are received. The wheel will pass and be tested by both search units. Upon expiration of the final test time during which through-transmissions were received the opposite pulser-receiver will be pulsed until the wheel passes over either switch 43 or 54, wherein the RIGHT or LEFT CONTROL SIGNAL is destroyed and further operation of the electronic test circuit is discontinued by resetting flip-flop 560.

If the wheel is crossing the search units 12 and 13 at a low speed, it will be separately tested upon passage over each search unit. However, for low speed testing only one search unit is required for testing comprising passing ultrasonic energy pulses around the wheel in both directions.

DEFECT DETECTION AND ALARM

The defect detection and alarm portion of the electronic test circuit 20 is shown at 26 of FIG. 17.

A defect in the surface of the wheel being tested causes a portion of the ultrasonic energy pulse traveling thereabout to be reflected therefrom. The reflected or echo pulse is returned to the second or pulsed transducer, as described above. The transducer produces a signal upon receipt of such an echo pulse, and the signal is relaxed to the corresponding pulser receiver 526 or 527.

Assuming that the wheel is approaching from the left and right pulser-receiver 526 was first pulsed, the first echo from a defect is received at right pulser-receiver 526 (See FIG. 18 at 713) and becomes an output on RIGHT VIDEO, which is transmitted through AND gate 546 to become VIDEO No. 1 as described above (See defect echoes 714 of FIG. 18). Video No. 1 comprises one input to AND gate 570 enabled by the positive TEST TIME No. 1 signal, which is positive during the test interval as described above. The echo pulse is transmitted through AND gate 570, OR gate 571, and a bias amplifier 572 to the TRANSIGATE 533 and an RM Chassis 573. The RM Chassis is commercially available from Automation Industries, Inc. Model No. 50C563.

The defect thereby causes an alarm signal, the output of which is used to drive a solenoid valve 574 of a paint spray dispenser 50 for low speed operation. An output terminal 575 for connection to car identification systems or the like is provided for high speed applications. The TRANSIGATE and RM Chassis have built in time delays for providing a sufficiently long alarm signal, which signal also encompasses further echo pulses past the first.

Echoes received by the left pulser receiver 527 in a RIGHT CONTROL situation comprise a VIDEO No. 2 signal, which is one input to AND gate 576 enabled by a positive TEST TIME No. 2 signal during the second test interval. The echo pulses are thereby transmitted through AND gate 576, OR gate 571, and raise the alarm signal.

If the LEFT CONTROL signal is positive and the left pulser-receiver 527 if first pulsed, defect echo pulses appear on LEFT VIDEO and are passed through AND gate 547 to become VIDEO No. 1 signals, which trigger the alarm as described above. Similarly, defect echo pulses in TEST TIME No. 2 comprise VIDEO No. 2, and are transmitted to the TRANSIGATE 533 through AND gate 576.

AUTOMATIC GAIN CONTROL

The electronic test circuit 20 is further provided with an automatic gain control portion 23. The purpose of the automatic gain control is to adjust the gain of the pulser receiver that has been pulsed, using as a guide the through-transmissions received at the opposite pulser receiver. It is useful because the echo pulses are often weak compared to through-transmission pulses, and amplification or gain adjustment of the echo pulse output is desirable. Also, the automatic gain control compensates for the varying strengths of energy pulses loaded into the wheel, wherein a less strong through-transmission is achieved. The automatic gain control also controls the output of the pulser-receiver receiving through-transmission signals, so that the through-transmission signals appear at one height on the video output and are thereby clearly distinguishable from background noise. (See VIDEO No. 2 through-transmission pulses 715 on FIG. 18).

A separate automatic gain control system is used for each channel. Again assuming that the right pulser-receiver 526 is being pulsed, its gain is adjusted for the period during which it may receive pulse echoes from a defect, and the gain of the left pulser-receiver 527 is adjusted to provide a uniform output for through-transmission pulses.

The first through-transmission received by the left pulser receiver becomes the VIDEO No. 2 signal as described above, and this signal comprises the input to a peak detector 580. The peak detector 580 provides a positive output at the highest level of an incoming peak of VIDEO No. 2. In the usual situation, the output of the peak detector 580 is set at the level corresponding to the level of the first through-transmission; however, if the first through-transmission were weak because of dirt interfering with boot-wheel coupling or the like, a subsequent higher level through-transmission pulse would raise the output of the peak detector. The output of the peak detector 580 passes through a reset amplifier inverter 581 which passes the output to a variable gain amplifier 582. The second input to the reset amplifier inverter 581 is the TEST TIME No. 2 signal, and the function of the reset amplifier inverter 581 is to cause the output of the peak detector 580 to be set at zero during the subsequent test time, during which the TEST TIME No. 2 signal is positive. Control of the right pulser-receiver 526 for reception of echo pulses is occurring during TEST TIME No. 1.

The second input to the automatic gain control network for pulser-receiver 526 comprises the TEST TIME No. 1 signal. As noted at 583, the TEST TIME No. 1 comprises a square wave positive signal for the duration of TEST TIME No. 1. This signal is the input to an integrator 584, the output of which during TEST TIME No. 1 is a linear positive going signal as indicated at 585. This signal is inverted by amplifier inverter 586, the output of which is shown at 587. The output of amplifier inverter 586 is integrated by a second integrator 588 creating an output signal as shown at 589. By virtue of the second integration, the output signal is initially relatively flat, and decreases more rapidly toward the end of the test time.

This double integrated output signal approximates the normal expected attenuation of the ultrasonic energy pulse in the wheel, and is appropriately amplified by power amplifier 590 and presented as the second input to variable gain amplifier 582.

The variable gain amplifier 582 accordingly produces an output indicated at 591 which approximates the normal decay of an ultrasonic energy pulse in the wheel, and is amplified according to the strength of the pulse as sensed by through-transmissions. This output is applied to the right pulser-receiver 526 through AND gate 592, enabled by the TEST TIME No. 1 signal, and AND gate 593, enabled by the RIGHT CONTROL signal. The high portion of the input wave 591 lowers the right video output of the right pulser-receiver 526 and the low portion of the input wave 591 causes the right output of right pulser-receiver 526 to be raised, the internal circuitry of the right pulser-receiver 526 having been designed to respond in this manner.

The output of power amplifier 590 comprising amplified wave form 589 is applied to the left pulser-receiver 527 through AND gate 594, enabled by TEST TIME No. 1, and AND gate 595, enabled by the RIGHT CONTROL signal. The left video output of left pulser receiver 527 is thereby caused to be higher as TEST TIME No. 1 proceeds, and the through-transmissions comprising the left video output are thereby held at a substantially uniform height.

Upon expiration of TEST TIME No. 1 and initiation of TEST TIME No. 2, the remaining elements of the automatic gain control perform in a similar manner to adjust the gain of left pulser-receiver 527 for the reception of echo pulses and to adjust the output of right pulser-receiver 526 to produce a uniform representation of through transmissions.

Initiation of TEST TIME No. 2 also causes the output of reset amplifier inverter 581 to return to zero.

The square wave signal comprising TEST TIME No. 2 is applied to an integrator 596, and inverter amplifier 597, a second integrator 598 and a power amplifier 599, all similar to the elements described above for TEST TIME No. 1. The output of power amplifier 599 comprises one input to a variable gain amplifier 600. The second input of variable gain amplifier 600 is derived from a peak detector 601 and a reset amplifier inverter 602 driven by the first through transmission signal on VIDEO No. 1. The output of variable gain amplifier 600 is similar to the wave form 591, and is applied to the left pulser-receiver 527 through AND gate 603 enabled by TEST TIME No. 2, and AND gate 595 enabled by the RIGHT CONTROL signal. The output of power amplifier 599 is delivered to the right pulser-receiver 526 through AND gate 604 enabled by TEST TIME No. 2 and AND gate 593 enabled by the RIGHT CONTROL signal.

If the LEFT CONTROL condition exists, indicating that the wheel is approaching the search unit from the right side, the functions of the right and left pulser-receivers 526 and 527 are reversed, although the TEST TIME No. 1 and VIDEO No. 2 signals remain the same, as described above. Therefore, the output of the automatic gain elements 580–591 would be delivered to the left pulser-receiver 527. Accordingly, the output variable gain amplifier 582 is delivered to left pulser-receiver 527 through AND gate 592, enabled by TEST TIME No. 1, and AND gate 605, enabled by the left control line. The output of power amplifier 590 is delivered to the right pulser receiver 526 through AND gate 594, enabled by TEST TIME No. 1, and AND gate 606 enabled by the LEFT CONTROL SIGNAL.

In the second test time, the output of variable gain amplifier 600 is delivered to the right pulser-receiver 526 through AND gate 603, enabled by TEST TIME No. 2, and AND gate 606, enabled by the LEFT CONTROL signal. The output of power amplifier 599 is delivered to the left pulser-receiver 527 through AND gate 604, enabled by TEST TIME No. 2, and AND gate 605, also enabled by the LEFT CONTROL signal.

WHEEL SIZE MEASUREMENT

The electronic test circuit 20 further comprises a wheel size arrangement portion 29 which indicates the size of the wheel being tested. (See also FIG. 17).

The wheel size measurement portion 29 comprises first a one and three-tenths millisecond delay network 610 having a normally high output. The input to this delay is the TX TIME No. 1 signal, which occurs as a result of TEST TIME No. 1 and VIDEO No. 2 being gated through AND gate 550, bias amplifier 551, and initiating delay 552. Thus the output of delay 610 goes negative for one and three-tenths milliseconds, beginning at the first through-transmission in TEST TIME No. 1.

The negative output of delay 610 causes a negative signal on the CLEAR input of an 8 bit shift register 611, and after expiration of the one and three-tenths millisecond delay, the output of a two millisecond delay 619 goes positive for two milliseconds. The output of delay 619 accomplishes three things: First, it starts an 8 khz. clock 612 which is gated to the shift register 611 through AND gate 613, which is enabled by the output of flip-flop 614 previously reset by the positive SYNC INHIBIT No. 1 signal. Second, operation of a 70 microsecond delay 615 having a normally positive output is initiated, wherein a 70 microsecond negative pulse is presented to the IN terminal of the 8 bit shift register 611 through OR gate 616. Third, AND gate 617 is enabled so that the next through-transmission can pass therethrough.

The effect of the above is to begin shifting a pulse up the 8 bit shift register, wherein the pulse was first presented to the shift register one and three-tenths milliseconds after the first through-transmission signal, TX TIME No. 1. At some time during the one and three-tenths millisecond delay, a second through-transmission is received. However, at this time AND gate 617 is not enabled, and the second through-transmission is not presented to the IN terminal of the shift register. The third through-transmission, occurring after the one and three-tenths millisecond delay, passes through AND gate 617 and initiates a 130-microsecond delay 618. The duration of the through transmission pulse may be only 20 to 30 microseconds and the delay therefore broadens the data pulse and presents it to the IN terminal of the shift register through OR gate 616. Thus, the third through-transmission pulse is also being shifted up the shift register by the clock 612 following the initial pulse provided by delay 615, and the amount of time between the two pulses is determined by the size of the wheel being tested. That is, the third through-transmission pulse will occur at an earlier time after the initial pulse for a small diameter wheel, and at a later time for a large diameter wheel.

The clock will continue shifting both the initial pulse and the data pulse for eight cycles. On the eighth cycle, the OUT terminal of the shift register goes negative, is inverted by inverter 620, and sets flip-flop 614 wherein AND gate 613 is turned off, thereby inhibiting the clock from further shifting the data pulse in the shift register. The data information comprising the third through-transmission is frozen on one of the bits of the shift register, the particular bit being determined by the time interval between the data bit and the initial pulse. If the data bit ends up on shift register bit 7 or 8, an output on terminal 621 is provided through OR gate 622, indicating that the wheel is in the size range of 25 inches to less than 30 inches. If the data bit ends up on bits 5 or 6, an output on terminal 623 is provided through OR gate 624 indicating that the wheel is in the size range of 30 inches to less than 33 inches. If the data bit ends up on bit 3 or 4 of the shift register, a signal on terminal 625 is provided through OR gate 626 indicating that the wheel is in the size range of 33 inches to less than 36 inches. Similarly, if the data bit ends up on bits 1 or 2 of the shift register, an output on terminal 627 is provided through OR gate 628, indicating that the wheel is in the size range of 36 inches to 40 inches.

For the purposes of the particular application herein, catagorizing the size of railroad wheels, it is sufficient to indicate a size range of the wheel. However, the technique described above can be easily adapted to more accurately measure wheel size. For instance, a faster clock rate can be used, and each bit of the shift register can comprise a single output. The number of bits in the shift register can be expanded if necessary for such a purpose.

The wheel size measurement circuitry is conditioned for a subsequent measurement when the SYNC INHIBIT No. 1 signal goes low and returns to positive, resetting flip-flop 614. The shift register is cleared by the output of delay 610.

The operation of the wheel size measurement circuitry is also apparent on the timing diagram shown in FIG. 18. The TX TIME No. 1 signal is shown at 730, going positive on the first through-transmission in TEST TIME No. 1, comprising the output of flip-flop 532. TX TIME No. 1 stays positive for 4 milliseconds, the duration of delay 552. The output of delay 610 is shown as the "Clear S.R." signal 731, followed by the seventy microsecond initial pulse input to the shift register 611 shown at 732. The clock is permitted to run at this time, as shown at 733. The clock input to the shift register is shown at the pulses 734. The timing diagram illustrates the size measurement of a small wheel, and the first data input to the shift register shown at 735, 130 microseconds in length by virtue of delay 618, is shown closely following the first clock pulses 734. At the end of eight clock pulses, the data output of the shift register as shown at 736 indicates a wheel 25 to less than 30 inches in diameter.

EXCESSIVE WEAR MEASUREMENT

The electronic test circuit 20 further comprises an excessive wear test portion 28. The excessive wear measurement is performed during TEST TIME No. 2, i.e. when the opposite direction pulse is introduced into the wheel.

The first input to the excessive wear circuitry 28 comprises the SYNC INHIBIT No. 2 signal, which is presented to a 600 microsecond delay network 630 having a normally high output. Upon expiration of the 600 microsecond delay, a second 800 microsecond delay 631 is initiated, the output of which enables AND gate 632. The second input to AND gate 632 comprises TX GATED DECISIONS No. 1, which is the through-transmissions during the second test time. Because AND gate 632 is enabled during the 800 microseconds following the first 600 microseconds of positive SYNC INHIBIT No. 2, only the first through-transmission will be passed through AND gate 632.

The first through-transmission pulse is made up of two lobes, as indicated at 633 and described above. The first lobe represents the portion of the through-transmission pulse which has traveled around the shorter running surface of the wheel being tested, and the second lobe is the portion of the pulse which has migrated to and traveled about the larger diameter flange of the wheel being tested. The time interval between the two lobes is directly dependent upon the difference in diameter between the running surface and the flange, and thus indicates the amount of wear the running surface has received.

The two-lobed TX GATED DECISIONS No. 1 pulse is presented to a present bistable flip-flop 634, having the characteristic that a first positive pulse will cause the output to go high and a subsequent positive pulse will return the output to the original low or quiescent level. The flip-flop 634 was previously set by the output of delay 619 during the TX TIME No. 1.

The output of flip-flop 634 therefore comprises a pulse, the width of which is dependent upon the separation of the lobes of the first through-transmission pulse. The square wave output of bistable flip-flop 634 starts a ramp generator 635, the output of which is a linear positive going signal, wherein the level attained by the signal is dependent upon the time the ramp generator was driven, which time is the length of the square wave pulse output of flip-flop 634. The output of the ramp generator is fed to a reset amplifier 636, which holds the attained level, and presents the attained level as an input to bias amplifier 637.

If the level of the input to the bias amplifier 637 is sufficiently high, indicating an unacceptable delay between the two lobes of the through-transmission pulse, the bias amplifier is triggered to provide an input to an 80 millisecond delay 638 the output of which is amplified by power amplifier 639 to provide an excessive wear alarm signal. The alarm signal may be sensed on terminal 640 for high speed operation, or may operate a solenoid 641 controlling the valve of an excessive wear paint spray dispenser 52.

The reset amplifier 636 is reset to its quiescent level upon initiation of a new test, and more particularly when the SYNC INHIBIT No. 1 signal has gone negative and returns to positive.

The operation of the excessive wear circuitry is also shown in the timing diagram comprising FIG. 18. The enabling of AND gate 632 for 800 microseconds is shown at 743, and the output of the bistable flip-flop 634 is shown at 744. The linear positive-going output of reset amplifier 636 is shown at 745, and is further shown exceeding an excessive wear level 746 at 747. The resultant 80 millisecond excessive wear alarm signal from delay 638 is shown at 748.

TEST CERTIFICATION

Electronic test circuit 20 further comprises a test certification portion 24. Assurance that a test has taken place could be derived at several points in the testing procedure, including the existence of a first through-transmission. However, in this preferred embodiment test certification is signaled only when both a wheel size measurement and wear measurement have been accomplished, wherein pulses have been delivered in both directions around the wheel being tested. It is preferable to test in both directions because a defect by virtue of its shape may be detected by testing in one direction, and may prove invisible by testing in the opposite direction.

The test certification circuitry first comprises a flip-flop 650 which is reset by a positive signal on the SYNC INHIBIT No. 1 line, which occurs near the beginning of the first test time. Flip-flop 650 is subsequently set when a wheel size indication has been made indicating that a test has been accomplished in one direction. Accordingly, flip-flop 650 is set by an output signal on one of terminals 621, 623, 625, or 627, whichever is positive, passing through OR gate 651 or OR gate 652.

The output of set flip-flop 650 enables one input of AND gate 653.

The other input to AND gate 653 comprises the output of bistable flip-flop 634. Therefore, AND gate 653 has an output coincident with the output of bistable flip-flop 634, which indicates that a test has been performed in the opposite direction during the second test time, and that an excessive wear measurement has resulted. The output of AND gate 653 is applied to an 80 millisecond delay 654, the output of which is amplified by power amplifier 655 to provide a test certification signal on terminal 656 for high speed operation, or to operate a solenoid 657 controlling a paint spray dispenser 48.

Referring to the timing diagram in FIG. 18 the certification output is shown as an 80 millisecond pulse 760.

The above-described system efficiently tests railroad wheels of all sizes for defects and wear, certifies that a test has been performed, and indicates the size of the wheel which has been tested. Testing is accomplished without disruption of normal train traffic, and at normal train speeds.

POTENTIALLY EXPLOSIVE "RESIDUAL STRESSED" WHEELS

The absence of a test certification signal, reflecting the failure of a first through-transmission pulse to set flip-flop 650, has been discovered to be a highly advantageous phenomenon, for it appears to be an indication of an "opaque" wheel, incapable of accepting an injected test pulse, or perhaps attenuating it so drastically that no measurable through-transmission pulse is delivered to either transducer, even with fully amplified gain of the first transducer's output.

Such opaque wheels delivering no measurable through-transmission pulse are exceedingly rare, constituting only one in every 10,000 or more wheels tested. Such unusual sonic characteristics are believed to indicate a highly atypical stress condition known as a "residual stress" condition, illustrated schematically in FIG. 19.

As fabricated, most railroad wheels have a compressive stress purposely created in their outer periphery by heat-treating and selective cooling. This characteristic has been introduced to render the running surface less sensitive to notches and cracks.

However, in service, repeated severe brake applications will elevate the running surface temperature to a point where, upon cooling, the original compressive stress condition has been reversed into a deep tensile stress situation, caused by the cooling gradient of atmospheric cooling.

As the wheel continues to roll under the same loading, surface cold working causes a thin layer of metal slowly to revert at first to a stress-relieved condition, and then to a compressive-stressed layer.

This condition may again be reconverted or worn off by subsequent brake application.

However, under certain as yet unknown circumstances, this thin compressive stress layer may be allowed to progress to significant depths. The boundary region between the thin compressive stress region and the deep underlying tensile condition is very sharp. It is believed that this boundary is the cause of the highly sound-attenuative situations encountered with certain wheels tested.

In such a wheel, should a small thermal crack develop on the outer surface, and be allowed to progress (from rolling action) to the stress boundary line, sudden failure of the wheel will occur upon the sudden release of the wheel's residual internal tension.

While such non-homogeneous stress loading is not fully understood, it seems theoretically probable that intermolecular slip planes permitting yield-stretching in the surface compression region A all terminate in a relatively narrow transition region C, between regions A and B, where unknown stress and yield phenomena occur. This region C is believed to produce unusually high acoustic attenuation, accounting for the evident opaque character of such wheels.

While experimental verification of the foregoing theory may prove difficult or impossible, the actual correlation between acoustic "opaqueness" and potentially explosive residual stress conditions have been confirmed in actual test operations. An opaque wheel of a locomotive identified by the system of this invention as it was leaving the Kansas City, Missouri yards of the Santa Fe Railroad was traced, and the locomotive was uncoupled from its train and returned to the yard for checking. As the marked opaque wheel was being forced from its axle, it suddenly cracked explosively, reflecting enormous built up residual stress.

As shown at the right hand side of FIG. 19, perhaps because of unique metallurgical constituents, crystal structure or heat treating conditions of manufacture or subsequent weather and braking incidents, continued operation of a heavily loaded wheel is believed to produce increasing values D, E, etc. of compressive stress and tensile stress in the regions A and B, producing opaque acoustic properties observable by the methods and apparatus of this invention, and eventually resulting in explosive rupture creating serious risk of derailments.

FIG. 20 is an actual photograph of an etched cut-away cross-section of a high attenuation opaque wheel identified by the systems of the present invention. In this cut-away etched wheel rim, the surface compression region A is a combination of pearlite and ferrite while the inner tension region B is a normal pearlite composition. The boundary line between these two regions is sharply delineated by a color change from the pearlite-ferrite to the pearlite, apparently corresponding to the transition stress region C shown in FIG. 19. A series of Martensite pockets F are visible around the outer periphery of the wheel rim in FIG. 20. It is believed that the original manufacturing heat treatment leaving wheels in compression is counteracted by severe braking applications during wheel operation, generating high temperatures at the wheel rim relieving the compressive stress and normalizing the steel wheels. If the wheels were not subjected to rolling stresses thereafter, they would normally cool and shrink, creating a normal inner tension region B as indicated in FIGS. 19 and 20. Rolling deformation under load is believed to cold work and stretch the tread rim of the wheel leaving an outer region tending to assume a larger diameter than the actual diameter of the wheel and thus held in compression by the integrity of the wheel itself. If cracks begin in Martensite pockets striking a switch, crossover or frog along the track, such cracks may proceed beyond the transition region C into the tension region B and may be responsible for explosive wheel failures.

The presence of a severe crack in the rim of a wheel may entirely block the normal circumperipheral through transmission pulse injected into the wheel by the systems of this invention, sent around its periphery and monitored by the opposite transducer in the normal operating mode of the device. When no through transmission pulse is received, and a wheel is known to be coupled to the test transducers, the presence of an opaque residually stressed wheel or a wheel with a major crack is indicated by a calamity alarm.

Two different automatic techniques are used to determine that a test is in progress. Back-scattered acoustic noise received by either of the transducers 122 or 124 generated by the original pulses injected into the wheel by the driving transducer serve to confirm acoustic coupling of the wheel with the transducer and clearly show that a test is in progress. Likewise, a defect return echo signal received by one of the transducers confirms acoustic coupling even in the absence of a through transmission pulse which may be entirely blocked by a severe crack.

Switching of the pulse signal between the two transducers may be initiated by a depth sounding transducer 125A shown in FIGS. 21 and 22 positioned in the mask 126A with its sonic axis directed downwardly toward internal floor 100E of the test unit assembly, and this may be used like a marine depth finder to signal the downward movement caused by the arrival of the wheel 39 over the test unit 12A. If the sonic axis of transducer 125A is substantially normal to floor 100E, contact of wheel 39 with boot 250A shortens the distance from transducer 125A to floor 100E producing a reduced depth echo pulse signal received by the transducer 125A which electrically confirms wheel coupling.

WORN WHEEL ALARM

A worn wheel or thin rim alarm is provided by a second supplemental transducer 125B mounted in the mask 126A facing upward with its sonic axis extending in a plane perpendicular to the normal path of wheel advance along support rail 106A. The sonic axis of transducer 125B is slightly tilted at an angle of between about 5° and 10° and preferably at an angle of substantially 7½° away from a radial line toward an internal rim edge of the wheel and it intersects the wheel's tread surface in a direction extending toward that internal rim edge 38A indicated in FIG. 21.

Pulsing of the transducer 125B and monitoring of the return time of echo pulses returned by corner reflection from the internal rim edge 38A permits a direct echo pulse distance measurement which may be employed to trigger an excess rim wear alarm if the echo pulse return time fails to exceed a predetermined return time corresponding to minimal allowable rim thickness.

The flexibility and versatility of the several preferred embodiments characterizing the systems of the present invention will be apparent from the foregoing description.

The system can also be readily modified for use on a variety of test objects. It can be modified for testing tires wherein a choice of coupling apparatus, medium, geometry, and transducer frequency is made to produce a deep penetrating surface wave traveling about the periphery of the tire in a manner similar to that disclosed above for railroad wheels.

The system can also be adapted to test a variety of metal test objects having curved peripheral surfaces, including gears, shafts, pipe, and the like. Test objects such as gears which have known irregularities can be tested by providing means for getting out or compensating for echo pulses from the known irregularities.

It will thus be seen that the objects set forth above, among those made apparent from the preceding description, are efficiently attained, and since certain changes may be made in carrying out the above method and in the construction set forth without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Having described our invention what we claim as new and desire to secure by Letters Patent is:

1. The method of testing the physical condition of a wheel comprising the steps of:
   A. coupling a tangent zone of the wheel with an ultrasonic energy transmitting medium having an index of refraction of ultrasonic energy substantially lower than the index of refraction of ultrasonic energy in the wheel;
   B. positioning a first ultrasonic transducer in the coupling medium with the sonic axis of the transducer inclined with respect to the tangent zone at an angle wherein low frequency ultrasonic energy delivered to the wheel along the sonic axis enters the wheel, penetrates to a substantial depth therein, and is refracted substantially tangent to the curved surface; and whereby the energy which penetrates the wheel to a substantial depth travels along a path near to and converging toward the curved surface and having a progressively increasing radius of curvature, and thereby migrates toward the curved surface thereof, as it travels along said path;
   C. coupling a second tangent zone of the wheel with an ultrasonic energy transmitting medium having an index of refraction of ultrasonic energy substantially lower than the index of refraction of ultrasonic energy in the wheel, said second tangent zone being at a known angular distance from the first tangent zone;
   D. positioning a second ultrasonic transducer in the coupling medium at the second tangent zone with the sonic axis of the second transducer inclined with respect to the tangent zone at an angle corresponding and opposite to the angle of the sonic axis of the first transducer relative to its tangent zone wherein ultrasonic energy delivered to the wheel by the first transducer and entering the tangent zone from within the wheel is refracted out of the wheel to the coupling medium to impinge upon the second transducer;
   E. pulsing the first ultrasonic transducer with a low frequency pulse to produce an ultrasonic energy pulse traveling along the sonic axis into the wheel, refracted substantially tangent to the surface thereof, and thereafter traveling about the periphery of the wheel adjacent to the surface;
   E. thereafter monitoring the second transducer for receipt of the ultrasonic energy pulse thereat; and
   G. measuring the time interval between pulsing the first transducer and receiving the ultrasonic energy pulse at the second transducer wherein the time interval is determined by the length of the circumference of the wheel within the known angular distance and therefore indicates the diameter of the wheel.

2. The method of testing a wheel as defined in claim 1 and further comprising the steps of:
   H. comparing the measured diameter of the wheel with the original diameter of the wheel; and
   I. signalling if an unacceptable deviation between the measured diameter and the original diameter exists.

3. A method for testing a wheel for both wear and residual stress conditions therein comprising the method steps defined in claim 1, and further comprising the step of:
   H. triggering a residual stress signal if a through-transmission pulse is not received at the second transducer within a predetermined time period after the pulsing of the first transducer.

4. The method of testing the physical condition of a wheel having a first wearing surface and a second concentric surface comprising the steps of:
   A. coupling a tangent zone of the wheel with an ultrasonic energy-transmission medium having an index of refraction of ultrasonic energy substantially lower than the index of refraction of ultrasonic energy of the wheel;

B. positioning a first ultrasonic transducer in the coupling medium with the sonic axis of the transducer substantially parallel to the plane of the wheel and inclined with respect to the tangent zone at an angle wherein ultrasonic energy delivered to the wheel along the sonic axis enters the wheel and is refracted substantially tangent to the wheel surface;

C. positioning a second ultrasonic transducer in the coupling medium with the sonic axis of the second transducer substantially parallel to the plane of the wheel and inclined with respect to the tangent zone at an angle corresponding and opposite to the angle of the sonic axis of the first transducer wherein ultrasonic energy entering the tangent zone from within the wheel is refracted out of the wheel through the coupling medium to impinge upon the second transducer;

D. pulsing the first ultrasonic transducer to produce an ultrasonic energy pulse which travels along the sonic axis into the wheel, is refracted substantially tangent to the surface thereof, and thereafter travels in a first direction about the periphery thereof with a portion adjacent to the first surface and a portion adjacent to the second concentric surface;

E. monitoring for through-transmission pulses received by the second transducer, the first through-transmission pulse received thereby having traveled about the smaller inner one of said two concentric surfaces, and the second through-transmission pulse having traveled about the outer one of said two concentric surfaces; and F. measuring the time interval between receiving the first through-transmission pulse and the second through-transmission pulse, the time interval corresponding to the difference in diameter between the first wear surface and the second concentric surface and thereby indicating the relative wear thereof.

5. The method of testing a wheel as defined in claim 4 and further comprising the step of:

G. marking the wheel if the relative wear is excessive.

6. The method of testing the physical conditions in a wheel comprising the steps of:

A. coupling a tangent zone of the wheel with an ultrasonic energy transmitting medium having an index of refraction of ultrasonic energy substantially lower than the index of refraction of ultrasonic energy in the wheel;

B. positioning a first ultrasonic transducer in the coupling medium with the sonic axis of the transducer inclined with respect to the tangent zone at an angle wherein low frequency ultrasonic energy delivered to the wheel along the sonic axis enters the wheel, penetrates to a substantial depth therein, and is refracted substantially tangent to the curved surface; and whereby the energy which penetrates the wheel to a substantial depth travels along a path near to and converging toward the curved surface and having a progressively increasing radius of curvature, and thereby migrates toward the curved surface thereof, as it travels along said path;

C. coupling a second tangent zone of the wheel with an ultrasonic energy transmitting medium having an index of refraction of ultrasonic energy substantially lower than the index of refraction of ultrasonic energy in the wheel, said second tangent zone being at a known angular distance from the first tangent zone;

D. positioning a second ultrasonic transducer in the coupling medium at the second tangent zone with the sonic axis of the second transducer inclined with respect to the tangent zone at an angle corresponding and opposite to the angle of sonic axis of the first transducer relative to its tangent zone wherein ultrasonic energy delivered to the wheel by the first transducer and entering the tangent zone from within the wheel is refracted out of the wheel to the coupling medium to impinge upon the second transducer;

E. pulsing the first ultrasonic transducer with a low frequency pulse to produce an ultrasonic energy pulse traveling along the sonic axis into the wheel, refracted substantially tangent to the surface thereof, and thereafter traveling about the periphery of the wheel adjacent to the surface;

F. thereafter monitoring the second transducer for receipt of the ultrasonic energy pulse thereat; and G. triggering a residual stress signal if the ultrasonic energy pulse is not received by the second transducer within a predetermined time period.

7. The method of testing for residual stress conditions in a wheel defined in claim 6, and further comprising the step of:

H. marking the wheel upon the triggering of said residual stress signal.

8. The method of testing for residual stress conditions in a wheel comprising the steps of:

A. coupling a tangent zone of the wheel with an ultrasonic energy transmitting medium having an index of refraction of ultrasonic energy substantially lower than the index of refraction of ultrasonic energy in the wheel;

B. positioning a first ultrasonic transducer in the coupling medium with the sonic axis of the transducer inclined with respect to the tangent zone at an angle wherein ultrasonic energy delivered to the wheel along the sonic axis enters the wheel, is refracted substantially tangent to the wheel surface and thereafter travels about the periphery of the wheel;

C. coupling a second tangent zone of the wheel with an ultrasonic energy transmitting medium having an index of refraction of ultrasonic energy substantially lower than the index of refraction of ultrasonic energy in the wheel, said second tangent zone being at a known angular distance from the first tangent zone;

D. positioning a second ultrasonic transducer in the coupling medium at the second tangent zone with the sonic axis of the second transducer inclined with respect to the tangent zone at an angle corresponding and opposite to the angle of sonic axis of the first transducer relative to its tangent zone wherein ultrasonic energy delivered to the wheel by the first transducer and entering the tangent zone from within the wheel is refracted out of the wheel to the coupling medium to impinge upon the second transducer;

E. pulsing the first ultrasonic transducer to produce an ultrasonic energy pulse traveling along the sonic axis into the wheel, refracted substantially tangent to the surface thereof, and thereafter traveling about the periphery of the wheel adjacent to the surface;

F. thereafter monitoring the second transducer for receipt of the ultrasonic energy pulse thereat;

G. reducing the gain of the amplified output of the first transducer as a function of the amplitude of through transmission pulses received by the second transducer; and H. triggering a residual stress signal when the amplitude of through transmission pulses received by the second transducer fails to exceed a predetermined threshold amplitude required to initiate said gain reduction.

9. Apparatus for testing railroad wheels comprising:

A. means presenting an ultrasonic energy-transmitting medium positioned in a test zone for ultrasonic coupled with the running surface of a railroad wheel, the ultrasonic energy-transmitting medium having an index of refraction substantially lower than the index of refraction of ultrasonic energy in the railroad wheel;

B. a first transducer positioned in the ultrasonic energy-transmitting medium with its sonic axis substantially parallel to the plane of the wheel and inclined with respect to a tangent to the running surface in the test zone at an angle wherein low frequency ultrasonic energy delivered to the wheel along the sonic axis enters the wheel, penetrates to a substantial depth therein, and is refracted substantially tangent to the curved surface; and whereby the energy which penetrates the wheel to a substantial depth travels along a path near to and converging toward the curved surface and having a progressively increasing radius of curvature, and thereby migrates toward the curved surface thereof, as it travels along said path;

C. a low ultrasonic frequency pulse generator connected to the first transducer for pulsing the first transducer to produce a low frequency ultrasonic energy pulse along its sonic axis;

D. a second transducer positioned in the ultrasonic energy-transmitting medium with its sonic axis substantially parallel to the plane of the wheel and inclined with respect to a tangent to the running surface in the test zone at an angle substantially equal and opposed to the angle of inclination of the sonic axis of the first transducer;

E. a through-transmission signal detector connected to the second transducer for detecting through-transmission pulses comprising a portion of the ultrasonic energy pulse produced by the first transducer, traveling about the periphery of the wheel in a first direction returning to the coupling medium, and refracted out of the wheel to impinge upon the second transducer.

10. Apparatus for testing railroad wheels comprising:

A. means presenting an ultrasonic energy-transmitting medium positioned in a test zone for ultrasonic coupling with the running surface of a railroad wheel, the ultrasonic energy-transmitting medium having an index of refraction substantially lower than the index of refraction of ultrasonic energy in the railroad wheel;

B. a first transducer positioned in the ultrasonic energy-transmitting medium with its sonic axis substantially parallel to the plane of the wheel and inclined with respect to a tangent to the running surface in the test zone at an angle wherein low frequency ultrasonic energy delivered to the wheel along the sonic axis enters the wheel and is refracted therein substantially tangent to the wheel surface, thereafter passing about the periphery of the wheel;

C. a pulse generator connected to the first transducer for pulsing the first transducer to produce a low frequency ultrasonic energy pulse along its sonic axis;

D. a second transducer positioned in the ultrasonic energy-transmitting medium with its sonic axis substantially parallel to the plane of the wheel and inclined with respect to a tangent to the running surface in the test zone at an angle substantially equal and opposed to the angle of inclination of the sonic axis of the first transducer;

E. a through-transmission signal detector connected to the second transducer for detecting through-transmission pulses comprising a portion of the ultrasonic energy pulse produced by the first transducer, traveling about the periphery of the wheel in a first direction returning to the coupling medium, and refracted out of the wheel to impinge upon the second transducer;

wherein the pulse generator is a synchronizing pulse generator set at a pulse interval greater than the time necessary for an ultrasonic energy pulse to travel about the periphery of the largest wheel to be tested, and wherein the output of the through-transmission signal detector controls the output of the synchronizing pulse generator to inhibit further pulsing upon receipt of the first through-transmission pulse, thereby permitting only one ultrasonic energy pulse to be delivered to the wheel.

11. Apparatus for testing railroad wheels comprising:

A. means presenting an ultrasonic energy-transmitting medium positioned in a test zone for ultrasonic coupling with the running surface of a railroad wheel, the ultrasonic energy-transmitting medium having an index of refraction substantially lower than the index of refraction of ultrasonic energy in the railroad wheel;

B. a first transducer positioned in the ultrasonic energy-transmitting medium with its sonic axis substantially parallel to the plane of the wheel and inclined with respect to a tangent to the running surface in the test zone at an angle wherein low frequency ultrasonic energy delivered to the wheel along the sonic axis enters the wheel and is refracted therein substantially tangent to the wheel surface, thereafter passing about the periphery of the wheel;

C. a pulse generator connected to the first transducer for pulsing the first transducer to produce a low frequency ultrasonic energy pulse along its sonic axis;

D. a second transducer positioned in the ultrasonic energy-transmitting medium with its sonic axis substantially parallel to the plane of the wheel and inclined with respect to a tangent to the running surface in the test zone at an angle substantially equal and opposed to the angle of inclination of the sonic axis of the first transducer;

E. a through-transmission signal detector connected to the second transducer for detecting through-transmission pulses comprising a portion of the ultrasonic energy pulse produced by the first transducer, traveling about the periphery of the wheel in a first direction returning to the coupling medium, and refracted out of the wheel to impinge upon the second transducer;

F. a time delay connected to the output of the through-transmission signal detector and initiated by the first through-transmission signal to provide a time interval following the first through-transmission pulse selected to permit substantial attenuation of the first ultrasonic energy pulse in the wheel to occur, and connected to provide an output signal following the time interval at a time delay output terminal;

G. a plurality of switches responsive to the output signal of the time delay and connected to:
 1. switch the output of the synchronizing pulse generator from the first transducer to the second transducer, and
 2. switch the output of the first transducer to the through-transmission signal detector, whereby the functions of the first and second transducers are reversed and the wheel is tested by passing an ultrasonic energy pulse about its periphery in a second, opposite direction; and H. a timer initiated by the arrival of an ultrasonic energy pulse at the test zone and stopped by the next through-transmission pulse thereafter, thereby timing the interval during which an ultrasonic energy pulse passes around the periphery of the wheel being tested; and I. a wheel size indicator responsive to the time interval for indicating the size of the wheel being tested.

12. Apparatus for testing railroad wheels comprising:

A. means presenting an ultrasonic energy-transmitting medium positioned in a test zone for ultrasonic coupling with the running surface of a railroad wheel, the ultrasonic energy-transmitting medium having an index of refraction substantially lower than the index of refraction of ultrasonic energy in the railroad wheel;

B. a first transducer positioned in the ultrasonic energy-transmitting medium with its sonic axis substantially parallel to the plane of the wheel and inclined with respect to a tangent to the running surface in the test zone at an angle wherein low frequency ultrasonic energy delivered to the wheel along the sonic axis enters the wheel and is refracted therein substantially tangent to the wheel surface, thereafter passing about the periphery of the wheel;

C. a pulse generator connected to the first transducer for pulsing the first transducer to produce a low frequency ultrasonic energy pulse along its sonic axis;

D. a second transducer positioned in the ultrasonic energy-transmitting medium with its sonic axis substantially parallel to the plane of the wheel and inclined with respect to a tangent to the running surface in the test zone at an angle substantially equal and opposed to the angle of inclination of the sonic axis of the first transducer;

E. a through-transmission signal detector connected to the second transducer for detecting through-transmission pulses comprising a portion of the ultrasonic energy pulse produced by the first transducer, traveling about the periphery of the wheel in a first direction returning to the coupling medium, and refracted out of the wheel to impinge upon the second transducer;

F. a time delay connected to the output of the through-transmission signal detector and initiated by the first through-transmission signal to provide a time interval following the first through-transmission pulse selected to permit substantial attenuation of the first ultrasonic energy pulse in the wheel to occur, and connected to provide an output signal following the time interval at a time delay output terminal;

G. a plurality of switches responsive to the output signal of the time delay and connected to;
 1. switch the output of the synchronizing pulse generator from the first transducer to the second transducer, and
 2. switch the output of the first transducer to the through-transmission signal detector, H. a timer initiated by a first lobe of a through-transmission pulse comprising a portion of the through-transmission pulse which has traveled about the running surface of the wheel, and stopped by a second lobe of a through-transmission pulse comprising a portion of the through-trans-mission pulse which has traveled about the larger diameter flange of the wheel, wherein the timed interval is proportional to the difference in diameter between the running surface and the flange; and I. an excessive wear indicator responsive to the time interval to produce an excessive wear output signal when the time interval exceeds a preset time interval determined by acceptable wear.

13. Apparatus for testing railroad wheels as defined in claim 12 and further comprising:

J. a second timer initiated by an ultrasonic energy pulse in the wheel at the test zone and stopped by the next through-transmission pulse thereafter, thereby timing the interval during which an ultrasonic energy pulse passes around the periphery being tested;

K. a wheel size indicator responsive to the time interval for indicating the size of the wheel being tested; and L. a test certification indicator responsive to the output of the excessive wear indicator and the wheel size indicator to produce a test certification signal in both a wheel size indication and a wear measurement.

14. Apparatus for testing railroad wheels as defined in claim 12 and further comprising:

J. a pressurized paint spray having an output nozzle directed toward the wheel being tested and a valve controlling the release of paint therefrom; and K. means for operating the valve responsive to an excessive wear alarm signal, whereby an excessively worn wheel is marked with paint.

15. Apparatus for testing railroad wheels as defined in claim 9 and further comprising;

f. a test certification indicator responsive to the output of the through-transmission signal detector to produce a test certification signal upon receipt of through transmissions about the periphery of the wheel by the through-transmission signal detector.

16. Apparatus for testing railroad wheels comprising:

A. a first rail segment comprising a portion of one rail of a railroad track;

B. a second rail segment positioned a spaced apart distance from the first rail segment and aligned therewith to comprise a second portion of the same rail of a railroad track; and C. a thin vertical support rail
 1. having a width substantially less than the width of the rail segments 2. positioned to span the longitudinal distance between the adjacent ends of the first and second rail segments
3. having its top surface aligned with the top surfaces of the rail segments whereby a railroad wheel rolling along the thin vertical support rail is exposed to a test zone adjacent to the support rail closely juxtaposed to but not intruding into the normal path of the railroad wheel; and further comprising;

D. an ultrasonic energy-transmitting medium positioned in the test zone adjacent to the thin vertical support rail for ultrasonic coupling with the running surface of a railroad wheel as it passes thereover, the ultrasonic energy-transmitting medium having an index of refraction substantially lower than the index of refraction of ultrasonic energy in the railroad wheel;

E. a first transducer positioned in the ultrasonic energy-transmitting medium with its sonic axis substantially parallel to the plane of the wheel and inclined with respect to the top surface of the thin vertical support rail at an angle wherein low frequency ultrasonic energy delivered to the wheel along the sonic axis enters the wheel and is refracted therein substantially tangent to the wheel surface, thereafter passing about the periphery of the wheel;

F. a pulse generator connected to the first transducer for pulsing the first transducer to produce a low frequency ultrasonic energy pulse along its sonic axis;

G. a defect signal detector connected to the first transducer for reception of the echo pulses comprising a portion of the ultrasonic energy pulse reflected from a defect in the wheel, returning along the periphery of the wheel to the ultrasonic energy transmitting medium, and refracted out of the wheel to impinge on the first transducer the defect signal detector producing a defect alarm signal upon receipt of a defect echo pulse;

H. a second transducer positioned in the ultrasonic energy-transmitted medium with its sonic axis substantially parallel to the plane of the wheel and inclined with respect to the top surface of the rail at an angle substantially equal and opposed to the angle of inclination of the sonic axis of the first transducer;

I. a through-transmission signal detector connected to the second transducer for detecting through-transmission pulses comprising a portion of the ultrasonic energy pulse produced by the first transducer, traveling about the periphery of the wheel in a first direction returning to the coupling medium, and refracted out of the wheel to impinge upon the second transducer;

J. a time delay connected to the output of the through-transmission signal detector and initiated by the first through-transmission signal to provide a time interval following the first through-transmission pulse selected to permit substantial attenuation of the first ultrasonic energy pulse in the wheel to occur, and connected to provide an output signal following the time interval at a time delay output terminal;

K. a plurality of switches responsive to the output signal of the time delay and connected to:

1. switch the output of the synchronizing pulse generator from the first transducer to the second transducer,
2. switch the output of the second transducer to the defect signal detector, and
3. switch the output of the first transducer to the through-transmission signal detector, whereby the functions of the first and second transducers are reversed and the wheel is tested by passing an ultrasonic energy pulse about its periphery in a second, opposite direction; and L. a timer initiated by the arrival of an ultrasonic energy pulse at the test zone and stopped by the next through-transmission pulse thereafter, thereby timing the interval during which an ultrasonic energy pulse passes around the periphery of the wheel being tested; and M. a wheel size indicator responsive to the time interval for indicating the size of the wheel being tested.

17. Apparatus for testing railroad wheels as defined in claim 16 wherein the thin support rail is aligned with the inside gauge edge of the rail segments for supporting the running surface of a railroad wheel rolling thereover adjacent to its flange.

18. The method of testing for the physical conditions in a wheel comprising the steps of:

A. coupling a tangent zone of the wheel with an ultrasonic energy transmitting medium having an index of refraction of ultrasonic energy substantially lower than the index of refraction of ultrasonic energy in the wheel;

B. positioning a first ultrasonic transducer in the coupling medium with the sonic axis of the transducer inclined with respect to the tangent zone at an angle wherein ultrasonic energy delivered to the wheel along the sonic axis enters the wheel, is refracted substantially tangent to the wheel surface and thereafter travels about the periphery of the wheel;

C. coupling a second tangent zone of the wheel with an ultrasonic energy transmitting medium having an index of refraction of ultrasonic energy substantially lower than the index of refraction of ultrasonic energy in the wheel, said second tangent zone being at a known angular distance from the first tangent zone;

D. positioning a second ultrasonic transducer in the coupling medium at the second tangent zone with the sonic axis of the second transducer inclined with respect to the tangent zone at an angle corresponding and opposite to the angle of sonic axis of the first transducer relative to its tangent zone wherein ultrasonic energy delivered to the wheel by the first transducer and entering the tangent zone from within the wheel is refracted out of the wheel to the coupling medium to impinge upon the second transducer;

E. pulsing the first ultrasonic transducer to produce an ultrasonic energy pulse traveling along the sonic axis into the wheel, refracted substantially tangent to the surface thereof, and thereafter traveling about the periphery of the wheel adjacent to the surface;

F. thereafter monitoring the second transducer for receipt of the circumperipheral through transmission ultrasonic energy pulse thereat; and G. triggering a high-risk stress condition alarm whenever no through transmission pulse is received by the second transducer during a time period when at least one of two test-in-progress conditions is occurring;
1. backscattered acoustic noise is received by one of the transducers confirming coupling of first transducer's output energy to the wheel; or
2. a defect return echo signal is received by one of the transducers.

19. The method defined in claim 18 wherein coupling of the wheel to the ultrasonic energy transmitting medium for both first and second transducers is confirmed by:
   A. enclosing both transducers in a resiliently depressible boot filled with the medium and presented for interfering contact with the tangent zones of the wheel,
   B. supporting both transducers in a carriage internally suspended within the depressible boot for free movement therewith,
   C. and positioning a third depth-sounding transducer on the carriage with its sonic axis substantially normal to a floor of the boot which is itself substantially parallel to the average tangent zones of the wheel,
   whereby wheel contact resiliently depressing the boot shortens the distance from the third transducer to the floor, producing a reduced-depth echo pulse signal received by the third transducer electrically confirming wheel contact.

20. The method of testing for physical conditions in a wheel comprising the steps of:
   A. coupling a tangent zone of the wheel with an ultrasonic energy transmitting medium having a index of refraction of ultrasonic energy substantially lower than the index of refraction of ultrasonic energy in the wheel;
   B. positioning a first ultrasonic transducer in the coupling medium with the sonic axis of the transducer inclined with respect to the tangent zone at an angle wherein ultrasonic energy delivered to the wheel along the sonic axis enters the wheel, is refracted substantially tangent to the wheel surface and thereafter travels about the periphery of the wheel;
   C. coupling a second tanget zone of the wheel with an ultrasonic energy transmitting medium having an index of refraction of ultrasonic energy substantially lower than the index of refraction of ultrasonic energy in the wheel, said second tangent zone being at a known angular distance from the first tangent zone;
   D. positioning a second ultrasonic transducer in the coupling medium at the second tangent zone with the sonic axis of the second transducer inclined with respect to the tangent zone at an angle corresponding and opposite to the angle of sonic axis of the first transducer relative to its tangent zone wherein ultrasonic energy delivered to the wheel by the first transducer and entering the tangent zone from within the wheel is refracted out of the wheel to the coupling medium to impinge upon the second transducer;
   E. pulsing the first ultrasonic transducer to produce an ultrasonic energy pulse traveling along the sonic axis into the wheel, refracted substantially tangent to the surface thereof, and thereafter traveling about the periphery of the wheel adjacent to the surface;
   F. thereafter monitoring the second transducer for receipt of the ultrasonic energy pulse thereat; and
   G. Positioning a third transducer in a resiliently depressible mounting with its sonic axis directed toward an underlying floor spaced a predetermined distance from the third transducer, with the mounting being depressible by a wheel coupled to the medium for the first and second transducers and thus reducing the predetermined distance and producing a reduced-depth echo pulse signal indicating wheel contact; and
   H. delivering this wheel contact signal to initiate the operation of switching means alternately delivering energizing electrical pulses to the first and the second transducers until a circumperipheral through transmission ultrasonic energy pulse is received by one of the first and second transducers.

21. Apparatus for testing railroad wheels as defined in claim 15 and further comprising:
   G. a pressurized paint spray having an output nozzle directed toward the wheel being tested and a valve controlling the release of paint therefrom; and
   H. means for operating the valve responsive to a test certification signal, whereby a wheel having been tested is marked with paint.

* * * * *

UNITED STATES PATENT AND TRADEMARK OFFICE
CERTIFICATE OF CORRECTION

PATENT NO. : 3,978,712

DATED : September 7, 1976

INVENTOR(S) : John Vincent Cowan, Gerald De G. Cowan, John Gerald Cowan

It is certified that error appears in the above-identified patent and that said Letters Patent are hereby corrected as shown below:

Column 3, line 13, cancel "peripheraly" and substitute therefor --periphery--.
Column 3, line 34, after first occurrence of "transducer", insert --opposed--.
Column 3, line 37, cancel "to" and substitute therefor --a--.
Column 8, line 10, after ".", cancel "the" and substitute therefor --The--.
Column 8, line 56, cancel "thus" and substitute therefor --Thus--.
Column 12, line 61, cancel "165" and substitute therefor --265--.
Column 13, line 4, cancel "8" and substitute therefor --38--.
Column 13, line 32, cancel "urthane" and substitute therefor --urethane--.
Column 15, lines 18 and 19, cancel "pemitting" and substitute therefor --permitting--.
Column 17, line 21, cancel "a" and substitute therefor --an--.
Column 17, line 68, cancel "Then" and substitute therefor --Thus--.
Column 18, line 68, cancel "redundent" and substitute therefor --redundant--.
Column 19, line 46, after "accomplished", insert --.--.
Column 20, line 8, cancel "postion" and substitute therefor --position--.
Column 20, line 11, cancel "transmision" and substitute therefor --transmission--.

UNITED STATES PATENT AND TRADEMARK OFFICE
CERTIFICATE OF CORRECTION

PATENT NO. : 3,978,712
DATED : September 7, 1976
INVENTOR(S) : John Vincent Cowan, Gerald De G. Cowan
John Gerald Cowan It is certified that error appears in the above-identified patent and that said Letters Patent are hereby corrected as shown below:

Column 20, line 38, cancel "deliverd" and substitute
    therefor --delivered--.
Column 22, line 55, cancel "transigate" and substitute
    therefor --Transigate--.
Column 23, line 32, cancel "therabout" and substitute
    therefor --thereabout--.
Column 23, line 56, after "right", insert
    -- pulser-receiver 526.  Therefore, ultrasonic
        energy transferred within the search unit
        from the pulsed transducer to the passive
        transducer and resulting in a VIDEO No. 2
        signal which is not a through-transmission
        is inhibited--.
Column 24, line 34, cancel "throughtransmission" and
    substitute therefor --through-transmission--.
Column 25, line 51, cancel "556" and substitute
    therefor --566--.
Column 26, line 54, cancel "second" and substitute
    therefor --sending--.
Column 26, line 57, cancel "relaxed" and substitute
    therefor --relayed--.
Column 29, line 40, cancel "arrangement" and substitute
    therefor --measurement--.
Column 36, line 37, cancel "E" and substitute
    therefor --F--.
Column 39, line 15, cancel "coupled" and substitute
    therefor --coupling--.

UNITED STATES PATENT AND TRADEMARK OFFICE
CERTIFICATE OF CORRECTION

PATENT NO. : 3,978,712

DATED : September 7, 1976

INVENTOR(S) : John Vincent Cowan, Gerald De G. Cowan, John Gerald Cowan

It is certified that error appears in the above-identified patent and that said Letters Patent are hereby corrected as shown below:

Column 42, line 19, cancel "through-trans-mission" and substitute therefor --through-transmission--.
Column 43, line 44, cancel "transmitted" and substitute therefor --transmitting--.
Column 45, line 34, cancel "a" and substitute therefor --an--.

Signed and Sealed this

Thirteenth Day of June 1978

[SEAL]

Attest:

RUTH C. MASON
Attesting Officer

DONALD W. BANNER
Commissioner of Patents and Trademarks